(12) United States Patent
Li et al.

(10) Patent No.: US 11,254,977 B2
(45) Date of Patent: Feb. 22, 2022

(54) UNIVERSAL REPORTER-BASED GENOTYPING METHODS AND MATERIALS

(71) Applicant: LIFE TECHNOLOGIES CORPORATION, Carlsbad, CA (US)

(72) Inventors: Kelly Li, San Jose, CA (US); Shoulian Dong, Mountain View, CA (US); Caifu Chen, Palo Alto, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 269 days.

(21) Appl. No.: 14/206,995

(22) Filed: Mar. 12, 2014

(65) Prior Publication Data

US 2014/0274774 A1 Sep. 18, 2014

Related U.S. Application Data

(60) Provisional application No. 61/777,168, filed on Mar. 12, 2013.

(51) Int. Cl.
*C12Q 1/68* (2018.01)
*C12Q 1/6858* (2018.01)

(52) U.S. Cl.
CPC .................. *C12Q 1/6858* (2013.01)

(58) Field of Classification Search
USPC ................................................. 435/6.12, 91.2
See application file for complete search history.

(56) References Cited

U.S. PATENT DOCUMENTS

| 5,866,336 | A | 2/1999 | Nazarenko et al. | |
| 6,090,552 | A | 7/2000 | Nazarenko et al. | |
| 7,033,763 | B2 * | 4/2006 | Liu | C12Q 1/6827 435/6.11 |
| 7,615,620 | B2 * | 11/2009 | Robinson | C12Q 1/6818 435/6.11 |
| 2003/0124512 | A1 * | 7/2003 | Stuyver | C07H 19/048 435/5 |
| 2003/0165859 | A1 | 9/2003 | Nazarenko et al. | |
| 2004/0009515 | A1 | 1/2004 | Liu et al. | |
| 2004/0259106 | A1 * | 12/2004 | Gunderson | C12Q 1/6827 435/6.11 |
| 2006/0177841 | A1 | 8/2006 | Wangh et al. | |
| 2010/0112565 | A1 | 5/2010 | Tobler et al. | |
| 2010/0129792 | A1 * | 5/2010 | Makrigiorgos | C12Q 1/6851 435/6.16 |

FOREIGN PATENT DOCUMENTS

| EP | 2971095 A2 | 1/2016 | | |
| WO | WO-0181631 A1 | 11/2001 | | |
| WO | WO-2011142836 A2 * | 11/2011 | ........... C12Q 1/6855 |

(Continued)

OTHER PUBLICATIONS

Myakishev et al. (Genome Research 2001, vol. 11:163-169).*

(Continued)

*Primary Examiner* — Stephanie K Mummert
(74) *Attorney, Agent, or Firm* — Workman Nydegger

(57) ABSTRACT

The present disclosure is drawn to methods for detection, quantitation and analysis of nucleotides of interest, for example SNPs, in nucleic acid sequences of interest using universal FRET-based reporter primers.

20 Claims, 29 Drawing Sheets

(56) References Cited

FOREIGN PATENT DOCUMENTS

WO    WO-2012/082753      6/2012
WO    WO-2014165210 A2    10/2014

OTHER PUBLICATIONS

Asari et al. (J Forensic Sci 2010, 55(6):1576-1581).*
Dixon et al. (Dissertation, 2006, "An Investigation Into The Use of Single Nucleotide Polymorphisms for Forensic Identification Purposes").*
Dixon et al. (Forensic Sci Int, 2005, vol. 154, 62-77).*
Cai et al. (Analytical Biochemistry 2010, 406:29-33) (Year: 2010).*
Rickert et al. (Clin Chem, 2004, vol. 50, p. 1680-1683) (Year: 2004).*
Myakishev et al. (Genome Research, 2001, 11:163-169) (Year: 2001).*
Bengra et al. (Clinical Chemistry, 2002, 48:12, p. 2131-2140) (Year: 2002).*
Asari, M. et al., "A New Method for Human ABO Genotyping Using a Universal Reporter Primer System", *Journal of Forensic Sciences*, vol. 55 (6), Nov. 1, 2010, 1576-1581.
Asari, M. et al., "Single Nucleotide polymorphism genotyping by mini-primer allele-specific amplification with universal reporter primers for identification of degraded DNA", *Analytical Biochemistry*, vol. 386 (1), Mar. 1, 2009, 85-90.
Myakishev, M. V. et al., "High-Throughput SNP Genotyping by Allele-Specific PCR with Universal Energy-Transfer-Labeled Primers", *Genome Res.*, vol. 11, 2001, 163-169.
PCT/US2014/024803, "International Search Report and Written Opinion dated Dec. 23, 2014", Dec. 23, 2014, 22 Pages.
Li X et al: "Universal Molecular Beacon-Based Tracer System For Real-time Polymerase Chain Reaction", Analytical Chemistry, American Chemical Society, US, vol. 78, No. 22, Nov. 15, 2006 (Nov. 15, 2006), pp. 7886-7890, XP008136133, ISSN: 0003-2700.
Livak, et al., "Oligonucleotides with Fluorescent Dyes at Opposite Ends Provide a Quenched Probe System Useful for Detecting PCR Product and Nucleic Acid Hybridization", PCR Methods and Applications vol. 4, No. 6, Jun. 1995, 357-362.
EP19207603.2, Partial Search Report, dated Feb. 20, 2020, 19 pages.

* cited by examiner

UNIVERSAL REPORTER-BASED GENOTYPING METHODS AND MATERIALS

CROSS REFERENCE TO RELATED APPLICATIONS

This application claims the benefit under 36 U.S.C. 119(e) of U.S. Provisional Application No. 61/777,168, filed on Mar. 12, 2013 (LT00774PRO), the contents of which is incorporated by reference in its entirety.

FIELD

This disclosure generally relates to the field of nucleic acid hybridization, and more particularly, to methods of nucleic acid amplification.

BACKGROUND

Nucleic acid analysis techniques that identify alterations or polymorphisms within known sequences are useful in many aspects of scientific, medical and forensic fields. For example, these techniques can be used in the genotyping of individuals in order to diagnose hereditary diseases or provide prognosis based on known genetic lesions. Genotypes of interest include, for example, point mutations, deletions, insertions and inversions as well as polymorphisms within nucleic acid sequences of interest. These techniques can also be used for clinical purposes such as tissue typing for histocompatability or for forensic purposes such as identity or paternity determination. Furthermore, nucleic acid analysis techniques can be used for the identification of organisms or to distinguish or identify pathogenic organisms of infectious agents. In addition, these techniques are useful in the identification and monitoring of genetically modified agricultural organisms such as crops and livestock.

Single nucleotide polymorphisms (SNPs) are an abundant form of genetic variation. These single nucleotide changes are found approximately every 500 bp in the human genome. Almost all SNPs are bi-allelic, that is, only two different alleles exist. Typically, one allele is present in the majority of the chromosomes of a population, and the alternative variant, that is, the minor allele, is present with less frequency. Only alleles that are present at a frequency greater than 1% are considered polymorphisms.

SNPs are promising tools for mapping susceptibility mutations that contribute to complex diseases. Although most SNPs are neutral and do not affect phenotype, they can be used as surrogate markers for positional cloning of genetic loci, because of the allele association, known as linkage disequilibrium, that can be shared by groups of adjacent SNPs. A need exists for alternative methods that give high performance and sequence specificity necessary to correctly identify a unique organism, disease state or clinical condition of interest that also have a simplified workflow, lower cost, and/or faster turn-around time.

SUMMARY

Provided herein are oligonucleotides, compositions, reaction mixtures, methods and kits for genotyping analysis, including, but not limited to SNP genotyping analysis. In certain embodiments, the oligonucleotides, compositions, reaction mixtures, methods and kits include universal FRET-based reporter primers and allele-specific primers.

In certain embodiments, oligonucleotides are provided that are specific for a particular allele or polymorphism. Such oligonucleotides are referred to herein as allele-specific primers or ASPs. Such allele-specific primers include an allele-specific portion and a 5'-universal tail; wherein the 5'-universal tail includes a binding site for a universal FRET-based reporter primer (herein referred to as "UFP") and the universal tail is not complementary to the target nucleic acid sequence (see FIG. 1). In certain embodiments, the 5'-universal tail includes a nucleotide sequence that is identical to the sequence of the universal FRET-based reporter primer. In certain embodiments, the 5'-universal tail includes a nucleotide sequence that is complementary to the sequence of the universal FRET-based reporter primer. In certain embodiments, the 3'-end of the allele-specific primer is extendable by a nucleic acid polymerase enzyme. In certain embodiments, the 3' end of the allele-specific primer includes a blocking agent such that the blocked end may be activated by a pyrophosphorolysis enzyme. In certain embodiments, the 3'-end of the allele-specific primer is extendable by a nucleic acid polymerase enzyme. In certain embodiments, the 3' end of the allele-specific primer includes a blocking agent such that the blocked end may be activated by a polyphosphorolysis enzyme. In certain embodiments, the blocking agent is a dideoxynucleotide (ddN). In certain embodiments, the allele-specific primer has a length of about 29 nucleotides to about 55 nucleotides. Preferably, the allele-specific primer has a length of about 35 nucleotides to about 50 nucleotides. Most preferably, the allele-specific primer has a length of about 43 nucleotides. In certain embodiments, the allele-specific portion has a $T_m$ of about 53° C. to about 65° C., preferably about 58° C. to about 62° C., most preferably about 59° C. In certain embodiments, oligonucleotides are provided that are specific for a particular locus of the target nucleic acid. Such oligonucleotides are referred to herein as locus-specific primers or LSPs. In certain embodiments, the locus-specific primer may serve as a reverse primer in the amplification and genotyping methods disclosed herein. In certain embodiments, the 3'-end of the LSP is extendable by a nucleic acid polymerase. In certain embodiments, the 3'-end of the LSP includes a blocking agent such that the blocked end may be activated by a pyrophosphorolysis enzyme. In certain embodiments, the 3'-end of the LSP includes a blocking agent such that the blocked end may be activated by a polyphosphorolysis enzyme In certain embodiments, the blocking agent is a dideoxynucleotide (ddN). In certain embodiments, the LSP may also be specific to a particular allele.

In certain embodiments, oligonucleotides are provided that may be used to detect the amplification of a target nucleic acid and/or may be used to monitor or detect the amplification of an allele or polymorphism in a target nucleic acid. Such oligonucleotides are referred to herein as universal FRET-based reporter primers (UFPs), wherein the universal FRET-based reporter primer includes at least one quencher moiety located at an internal position of the UFP and a fluorophore attached to the 5'-end of the UFP (see, FIG. 2). The fluorophore and at least one quencher may participate in FRET-based quenching. For example, when the UFP is not hybridized to the 5'-universal tail of the allele-specific primer or allele-specific primer extension product, the fluorescence of the fluorophore is quenched. However, upon hybridization of the UFP to its target sequence in the 5'-universal tail or the complement of the 5'-universal tail, the fluorescence of the fluorophore is no longer quenched and may be detected. In certain embodiments, the nucleotide sequence of the UFP is identical to the 5'-universal tail of the allele-specific primer. In certain embodiments, the nucleotide sequence of the UFP is complementary to the 5'-universal tail of the allele-specific primer. In certain embodiments, UFPs may be used to detect specific alleles (e.g., a first and second allele) or polymorphisms in a target nucleic acid, wherein a first allele-specific primer, which is specific for a first allele, includes a first 5'-universal tail which includes a binding site for a first UFP, wherein the first UFP includes a first fluorophore and at least one quencher moiety; and a second allele-specific primer which is specific for a second allele, includes a second 5'-universal tail which includes a binding site for a second UFP, wherein the second UFP includes a second fluorophore and at least one quencher moiety; wherein the first and second fluorophore are different and the at least one quencher moiety may be the same or different. In certain embodiments, a detectable signal is generated upon extension of the 3'-end of the UFP by a nucleic acid polymerase.

In various embodiments, the UFP has a fluorophore, "F" or "V," attached to the 5' end of the UFP, wherein the fluorophore may not be directly excitable by excitation light, and further where the UFP does not include a quencher moiety attached to the UFP. In these embodiments, a double-stranded nucleic acid intercalator dye is provided in the assay; where the double-stranded nucleic acid intercalator dye is directly excited by the excitation light and its fluorescence excites the fluorophore in the UFP. After hybridization of the UFP to the tail of the ASP, the UFP is polymerized (e.g. extended) and the double-stranded nucleic acid intercalator dye binds to the extended duplex. The intercalator dye is configured to be directly excited by excitation light, and its fluorescence excites the fluorophore of the UFP to fluoresce thereby providing a detectable signal.

In some embodiments, the 3'-end of the UFP comprises a blocking agent such that the blocked end is configured to be activated by pyrophosphorolysis or polyphosphorolysis. In various embodiments, the blocking agent is a dideoxynucleotide (ddN).

In certain embodiments, the UFP has a length from about 10 nucleotides to about 35 nucleotides. In some embodiments, the UFP has a length of about 15 nucleotides to about 35 nucleotides. In other embodiments, the UFP has a length of about 25 nucleotides. In certain embodiments, the UFP has a $T_m$ of about 50° C. to about 75° C., preferably about 60° C. to about 70° C., most preferably about 58° C. In certain embodiments, the distance between the internal quencher moiety and the fluorophore at the 5'-end of the UFP is about 8 nucleotides to about 25 nucleotides. Preferably, the distance between the internal quencher moiety and the 5'-fluorophore is about 12 nucleotides to about 18 nucleotides, most preferably about 15 nucleotides. In certain embodiments, the UFP includes one or more quencher moieties attached to one or more internal nucleotides. In certain embodiments, the UFP includes at least two quencher moieties attached to at least two internal nucleotides. In certain embodiments, the UFP includes two or more quencher moieties attached to two or more internal nucleotides. In certain embodiments, the UFP includes a linear conformation (e.g., a linear UFP). In certain embodiments, the UFP includes a stem-loop or hairpin conformation (e.g., a stem-loop UFP). In certain embodiments, the one or more internal quencher moieties are attached to one or more nucleotides located in one or more loop portions of the stem-loop UFP. In certain embodiments, the one or more internal quencher moieties are attached to one or more stem portions of the stem-loop UFP. In certain embodiments, the one or more internal quencher moieties are attached to one or more stem portions and one or more loop portions of the stem-loop UFP. In certain embodiments, the $T_m$ of UFP may be lower than the $T_m$ of the ASP. In certain embodiments, the $T_m$ of the UFP may be lower than the $T_m$ of the LSP. In certain embodiments, the $T_m$ of the UFP may be lower than the $T_m$ of both the ASP and the LSP.

In certain embodiments, oligonucleotides are provided that may be used to detect the amplification of a target nucleic acid and/or may be used to monitor or detect the amplification of an allele or polymorphism in a target nucleic acid. Such oligonucleotides are referred to herein as "universal FRET-based detector probes" wherein the universal FRET-based probe includes at least one quencher moiety at the 3'-end of the probe or at an internal position of the probe and a fluorophore attached to the 5'-end of the probe. The fluorophore and at least one quencher may participate in FRET-based quenching. For example, when the universal FRET-based detector probe is not hybridized to the 5'-universal tail of the allele-specific primer or allele-specific primer extension product, the fluorescence of the fluorophore is quenched. However, upon hybridization of the universal FRET-based probe to its target sequence in the 5'-universal tail or the complement of the 5'-universal tail, the quenching of the fluorescence of the fluorophore is reduced and the fluorophore may be detected. The fluorescence may be further increased when the probe is digested by 5'-nuclease activity of polymerase.

In certain embodiments, methods are provided for determining the genotype of a target nucleic acid molecule, the method includes: (1) providing one or more target nucleic acid molecules and a first allele-specific primer, which is specific for a first allele, including a first 5'-universal tail which includes a binding site for a first UFP, wherein the first UFP includes a first fluorophore and at least a first quencher moiety; and a second allele-specific primer which is specific for a second allele, including a second 5'-universal tail which includes a binding site for a second UFP, wherein the second UFP includes a second fluorophore and at least a second quencher moiety; wherein the first and second fluorophore are different and the at least first quencher moiety and the at least second quencher moiety may be the same or different; (2) providing a locus specific primer; (3) amplifying the target nucleic acids; (4) measuring the intensities of the first and the second fluorophore; (5) analyzing nucleic acid genotypes based on the intensities of the first and second fluorophores. In certain embodiments, the first fluorophore and the second fluorophore may be located at the 5'-end of the first and the second UFP respectively, and the at least first quencher moiety and the at least second quencher moiety may be each located at an internal nucleotide of the first UFP and the second UFP respectively. In certain embodiments, the UFPs may be in a linear conformation. In certain embodiments, the UFPs may be in a stem-loop conformation. In certain embodiments, one UFP may be in a stem-loop conformation and the other UFP may be in a linear conformation.

In certain embodiments, the 3'-end of at least one of the allele-specific primers and/or locus-specific primer includes a blocking agent such that the blocked end may be activated by pyrophosphorolysis. In various embodiments, the 3'-end of at least one of the allele-specific primers and/or locus-specific primer includes a blocking agent such that the blocked end may be activated by polyphosphorolysis. In certain embodiments, the blocking agent is a dideoxynucleotide (ddN). In certain embodiments, the LSP concentration is higher than that of the ASP.

In certain embodiments, the 3'-end of at least one of the first or second UFPs includes a blocking agent such that the blocked end may be activated by pyrophosphorolysis. In various embodiments, the 3'-end of at least one of t the first or second UFPs includes a blocking agent such that the blocked end may be activated by polyphosphorolysis. In some embodiments, both of the first and second UFPs include a blocking agent such that the blocked end may be activated by pyrophosphorolysis or polyphosphorolysis. In certain embodiments, the blocking agent is a dideoxynucleotide (ddN).

In certain embodiments, one or more of the UFPs are replaced with one or more universal FRET-based detector probes wherein one end of the universal FRET-based detector probe includes at least one quencher and the other end of the universal FRET-based detector probe includes a fluorophore. In certain embodiments, at least two universal FRET-based detector probes are used, wherein the first UFP is replaced by a first universal FRET-based detector probe includes at least a first quencher moiety and a first fluorophore; and the second UFP is replaced with a second universal FRET-based detector probe, wherein the second universal FRET-based detector probes includes at least a second quencher moiety and a second fluorophore; wherein the first and second fluorophores are different, and the at least first quencher moiety and the at least second quencher moiety may be the same or different. In certain embodiments, the 3'-end of at least one of the first or second universal FRET-based detector probes includes a blocking agent such that the blocked end is configured to be activated by pyrophosphorolysis or polyphosphorolysis. In some embodiments, the 3'-end of both of the first and second universal FRET-based detector probes includes a blocking agent such that the blocked end is configured to be activated by pyrophosphorolysis or polyphosphorolysis. In various embodiments, the blocking agent is a dideoxynucleotide (ddN). In certain embodiments, the 3'-end of at least one of the first or second universal FRET-based detector probes is configured to not be extendable under amplification conditions. In certain embodiments, the 3'-end of both the first and second universal FRET-based detector probes is configured to not be extendable under amplification conditions.

In certain embodiments, the UFP has a length of about 10 nucleotides to about 35 nucleotides. Preferably, the UFP has a length of about 15 nucleotides to about 35 nucleotides. Most preferably, the UFP has a length of about 25 nucleotides. In certain embodiments, the UFP has a $T_m$ of about 50° C. to about 75° C., preferably about 60° C. to about 70° C., most preferably about 58° C. In certain embodiments, the distance between the internal quencher moiety and the fluorophore at the 5'-end of the UFP is about 8 nucleotides to about 25 nucleotides. Preferably, the distance between the internal quencher moiety and the 5'-fluorophore is about 12 nucleotides to about 18 nucleotides, most preferably about 15 nucleotides. In certain embodiments, the UFP includes one or more quencher moieties attached to one or more internal nucleotides. In certain embodiments, the UFP includes at least two quencher moieties attached to at least two internal nucleotides. In certain embodiments, the UFP includes two or more quencher moieties attached to two or more internal nucleotides. In certain embodiments, the UFP includes a linear conformation (e.g., a linear UFP). In certain embodiments, the UFP includes a stem-loop or hairpin conformation (e.g., a stem-loop UFP). In certain embodiments, the one or more internal quencher moieties are attached to one or more nucleotides located in one or more loop portions of the stem-loop UFP. In certain embodiments, the one or more internal quencher moieties are attached to one or more stem portions of the stem-loop UFP. In certain embodiments, the one or more internal quencher moieties are attached to one or more stem portions and one or more loop portions of the stem-loop UFP. In certain embodiments, the $T_m$ of UFP may be lower than the $T_m$ of the ASP. In certain embodiments, the $T_m$ of the UFP may be lower than the $T_m$ of the LSP. In certain embodiments, the $T_m$ of the UFP may be lower than the $T_m$ of both the ASP and the LSP.

In certain embodiments, methods are provided for determining the genotype of a target nucleic acid molecule, the method including: (1) providing one or more target nucleic acid molecules and a first allele-specific primer, which is specific for a first allele, including a first 5'-universal tail which includes a binding site for a first UFP, wherein the first UFP includes a first fluorophore; and a second allele-specific primer which is specific for a second allele, comprising a second 5'-universal tail which includes a binding site for a second UFP, wherein the second UFP includes a second fluorophore; wherein the first and second fluorophore are different and may not be directly excited by excitation light; (2) providing a locus specific primer; (3) providing a double-stranded nucleic acid intercalator dye; wherein the double-stranded nucleic acid intercalator dye is directly excited by the excitation light and its fluorescence excites the fluorophores in the UFPs; (4) amplifying the target nucleic acids; (5) measuring the intensities of the first and the second fluorophore; (6) analyzing nucleic acid genotypes based on the intensities of the first and second fluorophores (see, FIG. 12). In various embodiments, the first fluorophore and the second fluorophore may be located at the 5'-end of the first UFP and second UFP respectively. In certain embodiments, the UFPs may be in a linear conformation. In certain embodiments, the UFPs may be in a stem-loop conformation. In certain embodiments, one UFP may be in a stem-loop conformation and the other UFP may be in a linear conformation.

In certain embodiments, the 3'-end of at least one of the allele-specific primers and/or locus-specific primer includes a blocking agent such that the blocked end may be activated by pyrophosphorolysis. In various embodiments, the 3'-end of at least one of the allele-specific primers and/or locus-specific primer includes a blocking agent such that the blocked end may be activated by polyphosphorolysis. In certain embodiments, the blocking agent is a dideoxynucleotide (ddN). In certain embodiments, the LSP concentration is higher than that of the ASP.

In certain embodiments, one or more of the UFPs are replaced with one or more universal FRET-based detector probes wherein one end of the universal FRET-based detector probe includes at least one quencher and the other end of the universal FRET-based detector probe includes a fluorophore. In certain embodiments, at least two universal FRET-based detector probes are used, wherein the first UFP is replaced by a first universal FRET-based detector probe includes at least a first quencher moiety and a first fluorophore; and the second UFP is replaced with a second universal FRET-based detector probe, wherein the second universal FRET-based detector probe includes at least a second quencher moiety and a second fluorophore; wherein the first and second fluorophores are different, and the at least first quencher moiety and the at least second quencher moiety may be the same or different.

In certain embodiments, compositions and/or reaction mixtures are provided for analyzing, quantitating or detecting one or more alleles or polymorphisms in a target nucleic acid, wherein the composition and/or reaction mixture includes one or more target nucleic acid molecules and a first allele-specific primer, which is specific for a first allele, including a first 5'-universal tail which includes a binding site for a first UFP, wherein the first UFP includes a first fluorophore and at least a first quencher moiety; and a second allele-specific primer which is specific for a second allele, including a second 5'-universal tail which includes a binding site for a second UFP, wherein the second UFP includes a second fluorophore and at least a second quencher moiety; wherein the first and second fluorophore are different and the at least first quencher moiety and the at least second quencher moiety may be the same or different. In various embodiments of the compositions and/or reaction mixtures, the first fluorophore and the second fluorophore are located at the 5'-end of the first UFP and the second UFP respectively, and the at least first quencher moiety and the at least second quencher moiety are located at an internal nucleotide of the first UFP and the second UFP respectively. In certain embodiments, the UFPs may be in a linear conformation. In certain embodiments, the UFPs may be in a stem-loop conformation. In certain embodiments, one UFP may be in a stem-loop conformation and the other UFP may be in a linear conformation. In various embodiments, the first UFP is replaced with a first universal FRET-based detector probe, where the first universal FRET-based detector probe includes at least a first quencher moiety and a first fluorophore; and the second UFP is replaced with a second universal FRET-based detector probe, wherein the second universal FRET-based detector probe includes at least a second quencher moiety and a second fluorophore; wherein the first and second fluorophores are different, and the at least first quencher moiety and the at least second quencher moiety are the same or different. In certain embodiments, the composition and/or reaction mixture further includes a locus specific primer. In various embodiments, the 3'-end of at least one of the first allele-specific primer, second allele-specific primers, first UFP, second UFP, or locus-specific primer includes a blocking agent such that the blocked end is configured to be activated by pyrophosphorolysis or polyphosphorolysis. In various embodiments, the 3'-end of at least one of the first or second universal FRET-based detector probes includes a blocking agent such that the blocked end is configured to be activated by pyrophosphorolysis or polyphosphorolysis. In various embodiments, the 3'-end of at least one of the first allele-specific primer, second allele-specific primers, first universal FRET-based detector probe, second universal FRET-based detector probe, or locus-specific primer includes a blocking agent such that the blocked end is configured to be activated by pyrophosphorolysis or polyphosphorolysis. In some embodiments, any combination of the first allele-specific primer, second allele-specific primers, first UFP, second UFP, or locus-specific primer includes a blocking agent such that the blocked end is configured to be activated by pyrophosphorolysis or polyphosphorolysis. In some embodiments, the blocking agent is a dideoxynucleotide (ddN). In some embodiments, any combination of the first allele-specific primer, second allele-specific primers, first universal FRET-based detector probe, second universal FRET-based detector probe, or locus-specific primer includes blocking agent such that the blocked end is configured to be activated by pyrophosphorolysis or polyphosphorolysis. In some embodiments, the blocking agent is a dideoxynucleotide (ddN). In various embodiments, the composition and/or reaction mixture further includes one or more polyphosphorolyzing agents.

In certain embodiments, the composition or reaction mixture further includes one or more nucleic acid polymerase, such as a thermostable polymerase; one or more reverse transcriptases, or any other DNA or RNA polymerase. In certain embodiments, the composition and/or reaction mixture includes one or more pyrophosphorolysis enzyme. In certain embodiments, the compositions and/or reaction mixtures include one or more polyphosphorolysis enzymes. In some embodiments, the compositions and/or reaction mixtures include one or more polyphosphorolyzing agents. In certain embodiments, the reaction mixture and/or composition further includes a universal FRET-based detector probe. In certain embodiments, the reaction mixture and/or composition further includes one or more buffers or buffering salts; one or more nucleotides; one or more dideoxynucleotides (ddN); one or more target/template molecules (which may also be used for determining reaction performance, i.e., control reactions); and other reagents for analysis or further manipulation of the products or intermediates produced by the methods described herein.

In certain embodiments, kits are provided that may be used to carry out hybridization, extension and amplification reactions using the oligonucleotides provided herein. Preferred kits may include one or more containers, such as vials, tubes and the like, configured to contain the reagents used in the methods described herein and optionally may contain instructions or protocols for using such reagents. The kits described herein may include one or more components selected from the group consisting of one or more oligonucleotides described herein, including but not limited to, one or more allele-specific primer, one or more universal FRET-based reporter primer, and one or more locus specific primer; one or more nucleic acid polymerase, such as a thermostable polymerase; one or more reverse transcriptases, or any other DNA or RNA polymerase. In some embodiments, the kit includes a first allele-specific primer, which is specific for a first allele, including a first 5'-universal tail which comprises a binding site for a first universal FRET-based reporter primer (UFP), where the first UFP includes a first fluorophore and at least a first quencher moiety; and a second allele-specific primer which is specific for a second allele, including a second 5'-universal tail which includes a binding site for a second UFP, where the second UFP includes a second fluorophore and at least a second quencher moiety; and where the first and second fluorophore may be the same or different. In some embodiments, the first fluorophore of the first UFP and the second fluorophore of the second UFP are located at the 5'-end of the first UFP and the second UFP respectively, and the at least first quencher moiety and the at least second quencher moiety are located at an internal nucleotide of the first UFP and the second UFP respectively. In certain embodiments, the kits described herein include one or more pyrophosphorolysis enzymes. In certain embodiments, the kits described herein include one or more polyphosphorolysis enzymes. In various embodiments, the kit includes one or more polyphosphorolyzing agents. In various embodiments, the 3'-end of at least one of the first or second allele-specific primers or locus-specific primer includes a blocking agent where the blocked end is configured to be activated by pyrophosphorolysis or polyphosphorolysis. In various embodiments, the 3'-end of at least one of the first or second UFPs includes a blocking agent such that the blocked end is configured to be activated by pyrophosphorolysis or polyphosphorolysis. In certain embodiments, the blocking agent is a dideoxynucleotide (ddN). In some embodiments, the first and second UFPs are in a linear conformation. In other embodiments, the first and second UFPs are in a stem-loop conformation. In yet other embodiments, the first UFP is in a stem-loop conformation and the second UFP is in a linear conformation. In certain embodiments, the kits described herein further include a universal FRET-based detector probe. In certain embodiments, the kits described herein further include one or more buffers or buffering salts; one or more nucleotides; one or more dideoxynucleotides (ddN); one or more target/template molecules (which may also be used for determining reaction performance, i.e., control reactions); and other reagents for analysis or further manipulation of the products or intermediates produced by the methods described herein. Such additional components may include components used for cloning and/or sequencing and components or equipment needed for the detection or quantification of the nucleic acid molecule of interest.

In certain embodiments, kits are further provided for use in the synthesis of a nucleic acid molecule, said kit including one or more oligonucleotides disclosed herein, including one or more universal FRET-based reporter primers and/or one or more allele-specific primers. In certain embodiments, kits are provided for use in amplification of a nucleic acid molecule, said kit including one or more oligonucleotides disclosed herein, including one or more universal FRET-based reporter primers and/or one or more allele-specific primers. In certain embodiments, kits are provided for the detection or measurement of nucleic acid synthesis or amplification products including said kit including one or more oligonucleotides disclosed herein, including one or more universal FRET-based reporter primers and/or one or more allele-specific primers.

These and other features of the present teachings are provided herein.

BRIEF DESCRIPTION OF THE DRAWINGS

FIG. 3A shows the results as a function of Cq and FIG. 3B shows the results as a function of delta Cq (DCq).

FIG. 4A: Analysis of detectable signal vs. distance between the fluorophore and quencher using "version 3" and "version 4" UFPs. FIG. 4B: Analysis of background signal vs. distance between the fluorophore and quencher using "version 3" and "version 4" UFPs.

FIG. 5A: Analysis of detectable signal and background for different linear UFP designs. FIG. 5B: Comparison on signal-to-noise ratio (S/N) of various stem-loop UFP designs.

DETAILED DESCRIPTION

Figure 1:
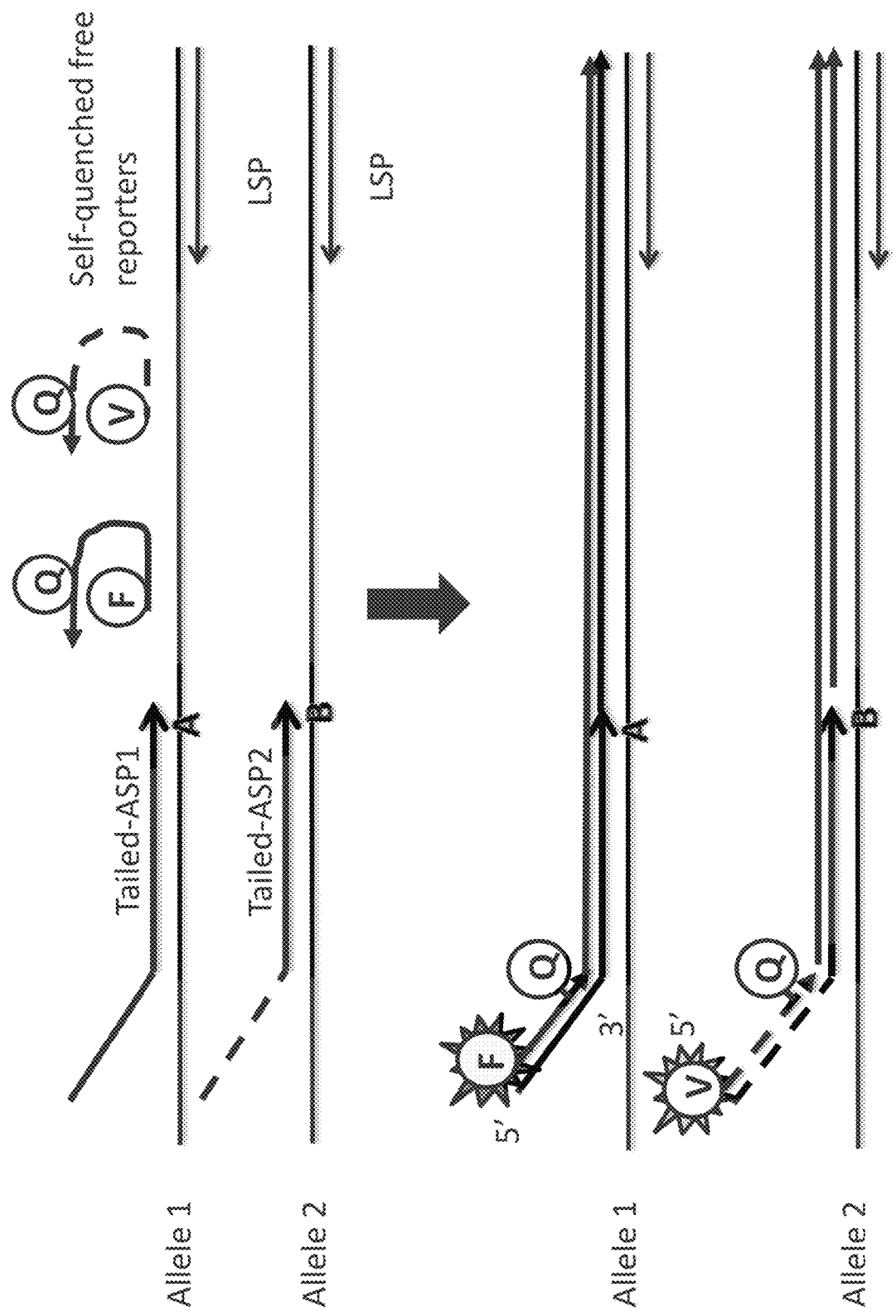
FIG. 1: A schematic for a UFP-based SNP genotyping assay according to certain embodiments of the present teachings. An assay consists of a pair of allele-specific primers each including a universal tail (ASP1 and ASP2), a shared locus-specific reverse primer (LSP), and a pair of universal FRET-based reporter primers (UFPs) for each of the two alleles, each of which includes a fluorophore ("F" or "V") and a quencher ("Q"). The UFPs may have a linear or stem-loop conformation.

Provided herein are oligonucleotides, compositions, reaction mixtures, methods and kits for genotyping analysis. In certain embodiments, the oligonucleotides, compositions, reaction mixtures, methods and kits include universal FRET-based reporter primers and allele-specific primers.

The present teachings combine the simplicity of universal FRET-based reporter primers (UFPs) with the high specificity of allele-specific primers. As described in the examples herein, primer-based allele discrimination provides high specificity between on- and off-target nucleic acid sequences. Both linear and stem-loop configurations of UFPs were analyzed and the distance between the internal quencher moiety and 5'-fluorophore was analyzed.

To more clearly and concisely describe and point out the subject matter of the present disclosure, the following definitions are provided for specific terms, which are used in the following description and the appended claims. Throughout the specification, exemplification of specific terms should be considered as non-limiting examples.

As used in this specification, the words "a" or "an" mean at least one, unless specifically stated otherwise. In this specification, the use of the singular includes the plural unless specifically stated otherwise. For example, but not as a limitation, "a target nucleic acid" means that more than one target nucleic acid can be present; for example, one or more copies of a particular target nucleic acid species, as well as two or more different species of target nucleic acid. The term "and/or" means that the terms before and after the slash can be taken together or separately. For illustration purposes, but not as a limitation, "X and/or Y" can mean "X" or "Y" or "X" and "Y".

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The section headings used herein are for organizational purposes only and are not to be construed as limiting the desired subject matter in any way. All literature cited in the specification, including but not limited to, patents, patent applications, articles, books and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

As used herein, the terms "amplification", "nucleic acid amplification", or "amplifying" refer to the production of multiple copies of a nucleic acid template, or the production of multiple nucleic acid sequence copies that are complementary to the nucleic acid template. The terms (including the term "polymerizing") may also refer to extending a nucleic acid template (e.g., by polymerization). The amplification reaction may be a polymerase-mediated extension reaction such as, for example, a polymerase chain reaction (PCR). However, any of the known amplification reactions may be suitable for use as described herein. The term "amplifying" that typically refers to an "exponential" increase in target nucleic acid may be used herein to describe both linear and exponential increases in the numbers of a select target sequence of nucleic acid.

The term "amplification reaction mixture" and/or "master mix" may refer to an aqueous solution including the various (some or all) reagents used to amplify a target nucleic acid. Such reactions may also be performed using solid supports (e.g., an array). The reactions may also be performed in single or multiplex format as desired by the user. These reactions typically include enzymes, aqueous buffers, salts, amplification primers, target nucleic acid, and nucleoside triphosphates. Depending upon the context, the mixture may be either a complete or incomplete amplification reaction mixture. The method used to amplify the target nucleic acid may be any available to one of skill in the art. Any in vitro means for multiplying the copies of a target sequence of nucleic acid may be utilized. These include linear, logarithmic, and/or any other amplification method. While this disclosure may generally discuss PCR as the nucleic acid amplification reaction, it is expected that the oligonucleotides, reaction mixtures and/or compositions described herein should be effective in other types of nucleic acid amplification reactions, including polymerase-mediated amplification reactions (such as helicase-dependent amplification (HDA), recombinase-polymerase amplification (RPA), and rolling circle amplification (RCA)), as well as ligase-mediated amplification reactions (such as ligase detection reaction (LDR), ligase chain reaction (LCR), and gap-versions of each), and combinations of nucleic acid amplification reactions such as LDR and PCR (see, for example, U.S. Pat. No. 6,797,470). For example, the oligonucleotides, reaction mixtures and/or compositions disclosed herein may be used in, for example, various ligation-mediated reactions, where for example ligation probes are employed as opposed to PCR primers. Additional exemplary methods include polymerase chain reaction (PCR; see, e.g., U.S. Pat. Nos. 4,683,202; 4,683,195; 4,965,188; and/or 5,035,996), isothermal procedures (using one or more RNA polymerases (see, e.g., PCT Publication No. WO 2006/081222), strand displacement (see, e.g., U.S. Pat. No. RE39007E), partial destruction of primer molecules (see, e.g., PCT Publication No. WO 2006/087574)), ligase chain reaction (LCR) (see, e.g., Wu, et al., *Genomics* 4: 560-569 (1990)), and/or Barany, et al. *Proc. Natl. Acad. Sci. USA* 88:189-193 (1991)), Qβ RNA replicase systems (see, e.g., PCT Publication No. WO 1994/016108), RNA transcription-based systems (e.g., TAS, 3SR), rolling circle amplification (RCA) (see, e.g., U.S. Pat. No. 5,854,033; U.S. Patent Application Publication No. 2004/265897; Lizardi et al. *Nat. Genet.* 19: 225-232 (1998); and/or Banér et al. *Nucleic Acid Res.*, 26: 5073-5078 (1998)), and strand displacement amplification (SDA) (Little, et al. *Clin. Chem.* 45:777-784 (1999)), among others. These systems, along with the many other systems available to the skilled artisan, may be suitable for use in polymerizing and/or amplifying target nucleic acids for use as described herein.

"Amplification efficiency" may refer to any product that may be quantified to determine copy number (e.g., the term may refer to a PCR amplicon, an LCR ligation product, and/or similar product). The amplification and/or polymerization efficiency may be determined by various methods known in the art, including, but not limited to, determination of calibration dilution curves and slope calculation, determination using qBase software as described in Hellemans et al., *Genome Biology* 8:R19 (2007), determination using the delta delta Cq (ΔΔCq) calculation as described by Livak and Schmittgen, *Methods* 25:402 (2001), or by the method as described by Pfaffl, *Nucl. Acids Res.* 29:e45 (2001), all of which are herein incorporated by reference in their entirety.

In certain embodiments, amplification techniques comprise at least one cycle of amplification, for example, but not limited to, the steps of: denaturing a double-stranded nucleic acid to separate the component strands; hybridizing a primer to a target flanking sequence or a primer-binding site of an amplicon (or complements of either, as appropriate); and synthesizing a strand of nucleotides in a template-dependent manner using a DNA polymerase. The cycle may or may not be repeated. In certain embodiments, a cycle of amplification comprises a multiplicity of amplification cycles, for example, but not limited to 20 cycles, 25 cycles, 30 cycles, 35 cycles, 40 cycles, 45 cycles or more than 45 cycles of amplification.

In some embodiments, amplifying comprises thermocycling using an instrument, for example, but not limited to, a GeneAmp® PCR System 9700, 9600, 2700 or 2400 thermocycler, an Applied Biosystems® ViiA™ 7 Real-Time PCR System, an Applied Biosystems® 7500 Fast Real-Time PCR System, a 7900HT Fast Real-Time PCR System, and the like (all available from Life Technologies Corp., Carlsbad, Calif.). In certain embodiments, single-stranded amplicons are generated in an amplification reaction, for example, but not limited to asymmetric PCR or A-PCR (see, for example, Gyllensten and Erlich, *Proc. Natl. Acad. Sci. USA* 85:7652-7657 (1988) and U.S. Pat. No. 5,066,584), or asynchronous thermal cycling (see, for example, U.S. Pat. No. 6,87,664).

In some embodiments, amplification comprises a two-step reaction including without limitation, a pre-amplification step wherein a limited number of cycles of amplification occur (for example, but not limited to, 2, 3, 4, or 5 cycles of amplification), then the resulting amplicon is generally diluted and portions of the diluted amplicon are subjected to additional cycles of amplification in a subsequent amplification step (see, e.g., U.S. Pat. No. 6,605,451 and U.S. Patent Application Publication No. 2004/0175733).

In certain embodiments, an amplification reaction comprises multiplex amplification, in which a multiplicity of different target nucleic acids and/or a multiplicity of different amplification product species are simultaneously amplified using a multiplicity of different primer sets. In certain embodiments, a multiplex amplification reaction and a single-plex amplification reaction, including a multiplicity of single-plex or lower-plexy reactions (for example, but not limited to a two-plex, a three-plex, a four-plex, a five-plex or a six-plex reaction) are performed in parallel.

The terms "amplicon" and "amplification product" as used herein generally refer to the product of an amplification reaction. An amplicon may be double-stranded or single-stranded, and may include the separated component strands obtained by denaturing a double-stranded amplification product. In certain embodiments, the amplicon of one amplification cycle can serve as a template in a subsequent amplification cycle.

The terms "annealing" and "hybridizing", including, without limitation, variations of the root words "hybridize" and "anneal", are used interchangeably and mean the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers and probes anneal to complementary sequences are well known in the art, e.g., as described in *Nucleic Acid Hybridization, A Practical Approach*, Hames and Higgins, eds., IRL Press, Washington, D.C. (1985) and Wetmur and Davidson, *Mol. Biol.* 31:349 (1968).

In general, whether such annealing takes place is influenced by, among other things, the length of the complementary portions of the primers and their corresponding binding sites in the target flanking sequences and/or amplicons, or the corresponding complementary portions of a reporter probe or a detection probe and its binding site; the pH; the temperature; the presence of mono- and divalent cations; the proportion of G and C nucleotides in the hybridizing region; the viscosity of the medium; and the presence of denaturants. Such variables influence the time required for hybridization. Thus, the preferred annealing conditions will depend upon the particular application. Such conditions, however, can be routinely determined by persons of ordinary skill in the art, without undue experimentation. Preferably, annealing conditions are selected to allow the primers and/or probes to selectively hybridize with a complementary sequence in the corresponding target flanking sequence or amplicon, but not hybridize to any significant degree to different target nucleic acids or non-target sequences in the reaction composition at the second reaction temperature.

The term "selectively hybridize" and variations thereof, means that, under appropriate stringency conditions, a given sequence (for example, but not limited to, a primer or probe) anneals with a second sequence comprising a complementary string of nucleotides (for example, but not limited to, a target flanking sequence or primer binding site of an amplicon), but does not anneal to undesired sequences, such as non-target nucleic acids, probes, or other primers. Typically, as the reaction temperature increases toward the melting temperature of a particular double-stranded sequence, the relative amount of selective hybridization generally increases and mis-priming generally decreases. In this specification, a statement that one sequence hybridizes or selectively hybridizes with another sequence encompasses situations where the entirety of both of the sequences hybridize or selectively hybridize to one another, and situations where only a portion of one or both of the sequences hybridizes or selectively hybridizes to the entire other sequence or to a portion of the other sequence.

As used herein, the term "stringency" is used to define the temperature and solvent composition existing during hybridization and the subsequent processing steps at which a hybrid comprised of two complementary nucleotide sequences will form. Stringency also defines the amount of homology, the conditions necessary, and the stability of hybrids formed between two nucleotide sequences. As the stringency conditions increase, selective hybridization is favored and non-specific cross-hybridization is disfavored. Increased stringency conditions typically correspond to higher incubation temperature, lower salt concentrations, and/or higher pH, relative to lower stringency conditions at which mis-priming is more likely to occur. Those in the art understand that appropriate stringency conditions to enable the selective hybridization of a primer or primer pair to a corresponding target flanking sequence and/or amplicon can be routinely determined using well known techniques and without undue experimentation (see, e.g., *PCR: The Basics from Background to Bench*, McPherson and Moller, Bios Scientific Publishers, 2000).

The terms "denaturing" and "denaturation" as used herein refer to any process in which a double-stranded polynucleotide, including without limitation, a genomic DNA (gDNA) fragment comprising at least one target nucleic acid, a double-stranded amplicon, or a polynucleotide comprising at least one double-stranded segment is converted to two single-stranded polynucleotides or to a single-stranded or substantially single-stranded polynucleotide, as appropriate. Denaturing a double-stranded polynucleotide includes, without limitation, a variety of thermal and chemical techniques which render a double-stranded nucleic acid single-stranded or substantially single-stranded, for example but not limited to, releasing the two individual single-stranded components of a double-stranded polynucleotide or a duplex comprising two oligonucleotides. Those in the art will appreciate that the denaturing technique employed is generally not limiting unless it substantially interferes with a subsequent annealing or enzymatic step of an amplification reaction, or in certain methods, the detection of a fluorescent signal.

As used herein, the term "genomic DNA" or "gDNA" refers to the total DNA from an organism, that is, the whole complement of an organism's DNA. Typically, this includes both the intron and exon sequences and the non-coding regulatory sequences, such as the promoter and enhancer sequences.

The terms "nucleic acid polymerase" and "DNA polymerase" are used herein in a broad sense and refers to any polypeptide that can catalyze the 5'-to-3' extension of a hybridized primer by the addition of deoxyribonucleotides and/or certain nucleotide analogs in a template-dependent manner. For example, but not limited to, the sequential addition of deoxyribonucleotides to the 3'-end of a primer that is annealed to a nucleic acid template during a primer extension reaction. Non-limiting examples of DNA polymerases include RNA-dependent DNA polymerases, including without limitation, reverse transcriptases, and DNA-dependent DNA polymerases. It is to be appreciated that certain DNA polymerases (for example, but not limited to certain eubacterial Type A DNA polymerases and Taq DNA polymerase) may further comprise a structure-specific nuclease activity and that when an amplification reaction comprises an invasive cleavage reaction.

As used herein, the term "$T_m$" is used in reference to melting temperature. The melting temperature is the temperature at which a population of double-stranded nucleic acid molecules becomes half dissociated into single strands.

The term "minor groove binder" as used herein refers to a small molecule that fits into the minor groove of double-stranded DNA, sometimes in a sequence specific manner Generally, minor groove binders are long, flat molecules that can adopt a crescent-like shape and thus, fit snugly into the minor groove of a double helix, often displacing water. Minor groove binding molecules typically comprise several aromatic rings connected by bonds with torsional freedom, for example, but not limited to, furan, benzene, or pyrrole rings.

The term "end-point" measurement refers to a method where data collection occurs only once the reaction has been stopped.

The terms "real-time" and "real-time continuous" are interchangeable and refer to a method where data collection occurs through periodic monitoring during the course of the polymerization reaction. Thus, the methods combine amplification and detection into a single step.

As used herein, the term "quantitative PCR" or "qPCR" refers to the use of the polymerase chain reaction (PCR) to quantify gene expression.

As used herein the terms "$C_t$" and "cycle threshold" refer to the time at which fluorescence intensity is greater than background fluorescence. They are characterized by the point in time (or PCR cycle) where the target amplification is first detected. Consequently, the greater the quantity of target DNA in the starting material, the faster a significant increase in fluorescent signal will appear, yielding a lower $C_t$.

As used herein, the term "high resolution melt" or "HRM" refers to a technique for determining a sequence variation in a nucleic acid by analyzing a melting curve of the nucleic acid. The nucleic acid can be double-stranded or single-stranded. In certain embodiments, a signal representing a double-stranded nucleic acid may be measured in real time.

In certain embodiments, real time measurement ($C_t$) of the PCR may be used as a quality control value for melt analysis such as HRM analysis. In certain embodiments, end point analysis may be employed. In certain embodiments, single-stranded nucleic acids may be analyzed, for example, single-stranded nucleic acids can fold to form duplexes or other higher ordered structures that can then be analyzed. Herein, the term "high resolution melt" or "HRM" can also refer to a technique for determining sequence variations between two different nucleic acids by analyzing the shape of the melting curve, including the melting temperature and the slope.

As used herein, the term "primer" refers to a synthetically or biologically produced single-stranded oligonucleotide that is extended by covalent bonding of nucleotide monomers during amplification or polymerization of a nucleic acid molecule. Nucleic acid amplification often is based on nucleic acid synthesis by a nucleic acid polymerase or reverse transcriptase. Many such nucleic acid polymerases or reverse transcriptases require the presence of a primer that may be extended to initiate such nucleic acid synthesis. As will be appreciated by those skilled in the art, the oligonucleotides disclosed herein may be used as one or more primers in various extension, synthesis, or amplification reactions. According to certain embodiments, the amplification of nucleic acid sequences may involve the use of locus-specific, group-specific, and/or allele-specific primers. Locus-specific primers (LSPs) may be used to amplify all alleles encoded at a given locus, but not all alleles encoded by other loci. Allele-specific primers (ASPs) amplify families of alleles that share a common polymorphism. Allele-specific primers may be used to amplify a single allele and may be capable of differentiating between two sequences that differ by only a single base difference of change. According to certain embodiments, amplification methods may comprise combinations of locus-specific primers to amplify and analyze both alleles in a heterozygous sample, followed by allele-specific amplification to isolate one of the two alleles for further characterization. In certain embodiments, two locus-specific primers may be used in a preamplification reaction before a genotyping reaction is carried out.

As used herein, the term "allele-specific primer" or "ASP" refers to a primer that binds to a specific sequence on a region of a nucleic acid to be amplified. These types of primers may be used to amplify and discriminate between two or more alleles of a gene, for example, simultaneously. The difference between the two alleles may be a SNP, an insertion, or a deletion. One or each allele-specific primer may independently comprise a nucleotide sequence comprising a 5'-universal tail, wherein the 5'-universal tail is not complementary to the target nucleic acid. In some embodiments, at least one of the allele-specific primers contains a 5'-universal tail. For example, at least one SNP allele-hybridizable sequence and at least one nucleotide alteration may be provided in one or more of the allele-specific primers. In certain embodiments, the 3'-end of the allele-specific primer is extendable by a nucleic acid polymerase. In certain embodiments, the 3'-end of the allele-specific primer may be blocked by techniques known in the art such that the blocked end may be activated by a pyrophosphorolysis enzyme or similar type of enzyme. In various embodiments, the 3'-end of the allele-specific primer may be blocked by techniques known in the art such that the blocked end may be activated by a polyphosphorolysis enzyme or similar type of enzyme.

As used herein, the term "locus-specific primer" or "LSP" refers to a primer that binds to a particular region of a nucleic acid to be amplified. Generally, an allele-specific primer and a locus-specific primer are utilized to perform PCR on leading and lagging strands of a DNA or template strand and complement. In certain embodiments, the 3'-end of the LSP may be extended by a nucleic acid polymerase. In certain embodiments, the 3'-end of the locus-specific primer may be blocked by techniques known in the art. The blocked end may be activated by a pyrophosphorolysis enzyme or similar type of enzyme. The blocked end may be activated by a polyphosphorolysis enzyme or similar type of enzyme. In certain embodiments, a locus-specific primer may already be hybridized to a nucleic acid before the hybridized nucleic acid is amplified, such that a method is provided that does not require a step of hybridizing a locus-specific primer.

The terms "complementarity" and "complementary" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementarity refers to the situation in which each nucleotide unit of one polynucleotide strand or region can hydrogen bond with each nucleotide unit of a second polynucleotide strand or region. "Less than perfect complementarity" refers to the situation in which some, but not all, nucleotide units of two strands or two units can hydrogen bond with each other.

As used herein, the term "reverse complement" refers to a sequence that will anneal/base pair or substantially anneal/base pair to a second oligonucleotide according to the rules defined by Watson-Crick base pairing and the antiparallel nature of the DNA-DNA, RNA-RNA, and RNA-DNA double helices. Thus, as an example, the reverse complement of the RNA sequence 5'-AAUUUGC would be 5'-GCAAAUU. Alternative base pairing schemes, including but not limited to G-U pairing, can also be included in reverse complements.

As used herein, the term "probe" refers to synthetic or biologically produced nucleic acids (DNA or RNA) which, by design or selection, contain specific nucleotide sequences that allow them to hybridize, under defined stringencies, specifically (i.e., preferentially) to target nucleic acid sequences. In the present teachings, probes may be labeled, e.g., with a fluorescent dye, or a pair of labels comprising a fluorophore reporter dye and a quencher to enable detection.

As used herein, "substantially less extendable" is used to characterize an oligonucleotide that is inefficiently extended or not extended in an extension and/or amplification reaction when the 3' most nucleotide of the oligonucleotide is not complementary to the corresponding base of a target/template nucleic acid.

As used herein, the term "template" is interchangeable with "target molecule" or "target nucleic acid" and refers to a double-stranded or single-stranded nucleic acid molecule which is to be amplified, copied or extended, synthesized, or sequenced. In the case of a double-stranded DNA molecule, denaturation of its strands to form a first and a second strand is performed to amplify, sequence, or synthesize these molecules. A primer, complementary to a portion of a template is hybridized under appropriate conditions and the polymerase (DNA polymerase or reverse transcriptase) may then synthesize a nucleic acid molecule complementary to said template or a portion thereof. The newly synthesized molecule, according to the present disclosure, may be equal or shorter in length than the original template. Mismatch incorporation during the synthesis or extension of the newly synthesized molecule may result in one or a number of mismatched base pairs. Thus, the synthesized molecule need not be exactly complementary to the template. The template may be an RNA molecule, a DNA molecule, or a DNA/RNA hybrid molecule. A newly synthesized molecule may serve as a template for subsequent nucleic acid synthesis or amplification.

The target nucleic acid may be obtained from any source, and may comprise any number of different compositional components. For example, the target may be a nucleic acid (e.g., DNA or RNA), cDNA, transfer RNA (tRNA), small interfering RNA (siRNA), microRNA (miRNA), or other mature small RNA, and may comprise nucleic acid analogs or other nucleic acid mimics. The target may be methylated, non-methylated, or both. The target may be bisulfite-treated and non-methylated cytosines converted to uracil. Further, it will be appreciated that "target nucleic acid" may refer to the target nucleic acid itself, as well as surrogates thereof, for example, amplification products and native sequences. The target molecules of the present teachings may be derived from any number of sources, including without limitation, viruses, archae, protists, prokaryotes and eukaryotes, for example, but not limited to, plants, fungi, and animals. These sources may include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil), research samples generally, purified samples generally, cultured cells and lysed cells. It will be appreciated that target nucleic acids may be isolated from samples using any of a variety of procedures known in the art, for example, the Applied Biosystems ABI Prism® 6100 Nucleic Acid Prep-Station (Life Technologies Corp., Carlsbad, Calif.) and the ABI Prism® 6700 Automated Nucleic Acid Workstation (Life Technologies Corp.), Ambion® mirVana™ RNA isolation kit (Life Technologies Corp.), and the like. It will be appreciated that target nucleic acids may be cut or sheared prior to analysis, including the use of such procedures as mechanical force, sonication, restriction endonuclease cleavage, or any method known in the art. In general, the target nucleic acids of the present teachings will be single-stranded, though in some embodiments the target nucleic acids may be double-stranded, and a single-strand may result from denaturation.

As used herein, the terms "hairpin" and "stem-loop" are interchangeable and are used to indicate the structure of an oligonucleotide in which one or more portions of the oligonucleotide form base pairs with one or more other portions of the oligonucleotide. When the two portions are base paired to form a double-stranded portion of the oligonucleotide, the double-stranded portion may be referred to as a stem. Thus, depending on the number of complementary portions used, a number of stems (preferably about 1 to about 10) may be formed.

The terms "nucleic acid binding dye" or "double-stranded nucleic acid intercalating dye" as used herein refer to a fluorescent molecule that is specific for a double-stranded polynucleotide or that at least shows a substantially greater fluorescent enhancement when associated with double-stranded polynucleotides than with a single stranded polynucleotide. Typically, nucleic acid binding dye molecules associate with double-stranded segments of polynucleotides by intercalating between the base pairs of the double-stranded segment, but binding in the major or minor grooves of the double-stranded segment, or both. Non-limiting examples of nucleic acid binding dyes include ethidium bromide, DAPI, Hoechst derivatives including without limitation Hoechst 33258 and Hoechst 33342, intercalators comprising a lanthanide chelate (for example, but not limited to, a naphthalene diimide derivative carrying two fluorescent tetradentate β-diketone-$Eu^{3+}$ chelates (NDI-$(BHHCT-Eu^{3+})_2$), see e.g., Nojima et al., *Nucl. Acids Res. Suppl. No.* 1 105 (2001), and certain unsymmetrical cyanine dyes such as SYBR® Green, SYBR® GreenER™ and PicoGreen® and their derivatives.

As used herein, the terms "polynucleotide", "oligonucleotide," and "nucleic acid" are used interchangeably and refer to single-stranded and double-stranded polymers of nucleotide monomers, including without limitation, 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof and may include nucleotide analogs. The nucleotide monomer units may comprise any of the nucleotides described herein, including, but not limited to, nucleotides and/or nucleotide analogs. Polynucleotides typically range in size from a few monomeric units, e.g., 5-40 when they are sometimes referred to in the art as oligonucleotides, to several thousands of monomeric nucleotide units. Unless denoted otherwise, whenever a polynucleotide sequence is represented, it will be understood that the nucleotides are in the 5'-to-3' order from left to right and that "A" denotes deoxyadenosine, "C" denotes deoxycytosine, "G" denotes deoxyguanosine, "T" denotes deoxythymidine, and "U" denotes deoxyuridine, unless otherwise noted.

The term "nucleotide" refers to a phosphate ester of a nucleoside, e.g., triphosphate esters, wherein the most common site of esterification is the hydroxyl group attached at the C-5 position of the pentose.

The term "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms. When the nucleoside base is purine or 7-deazapurine, the pentose is attached to the nucleobase at the 9-position of the purine or deazapurine, and when the nucleobase is pyrimidine, the pentose is attached to the nucleobase at the 1-position of the pyrimidine.

The term "analog" includes synthetic analogs having modified base moieties, modified sugar moieties, and/or modified phosphate ester moieties. Phosphate analogs generally comprise analogs of phosphate wherein the phosphorous atom is in the +5 oxidation state and one or more of the oxygen atoms is replaced with a non-oxygen moiety, e.g. sulfur. Exemplary phosphate analogs include: phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$. Exemplary base analogs include: 2,6-diaminopurine, hypoxanthine, pseudouridine, C-5-propyne, isocytosine, isoguanine, 2-thiopyrimidine. Exemplary sugar analogs include: 2'-or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, and bromo.

As used herein, the term "single nucleotide polymorphism" (SNP) refers to a DNA sequence variation occurring when a single nucleotide, e.g., A, T, C, or G, in the genome (or other shared sequence) differs between members of a species (or between paired chromosomes in an individual). For example, two sequenced DNA fragments from different individuals, AAGCCTA to AAGCTTA contain a difference in a single nucleotide. In this case, it is to be understood that there are two alleles: C and T. Almost all common SNPs have only two alleles.

As used herein, the term "reaction vessel" generally refers to any container, chamber, device, or assembly, in which a reaction can occur in accordance with the present teachings. In some embodiments, a reaction vessel may be a microtube, for example, but not limited to, a 0.2 mL or a 0.5 mL reaction tube such as a MicroAmp® Optical tube (Life Technologies Corp., Carlsbad, Calif.) or a micro-centrifuge tube, or other containers of the sort in common practice in molecular biology laboratories. In some embodiments, a reaction vessel comprises a well of a multi-well plate, a spot on a glass slide, or a channel or chamber of a microfluidics device, including without limitation a TaqMan® Low Density Array or a TaqMan® Open Array Real-Time PCR plate (both from Life Technologies Corp.). For example, but not as a limitation, a plurality of reaction vessels can reside on the same support. In some embodiments, lab-on-a-chip-like devices available, for example, from Caliper, Fluidigm and Life Technologies Corp., including the Ion 316TH and Ion 318TH Chip, may serve as reaction vessels in the disclosed methods. It will be recognized that a variety of reaction vessels are commercially available or can be designed for use in the context of the present teachings.

The term "reporter group" is used in a broad sense herein and refers to any identifiable tag, label, or moiety.

The term "polyphosphorolysis" refers to the removal of a non-extendable nucleotide from a nucleic acid (e.g. an oligonucleotide) in the presence of one or more polyphosphorylyzing agents and an enzyme that exhibits polyphosphorolyzing activity.

The term "polyphosphorolysis enzyme" is a DNA polymerase that catalyzes polymerization of nucleoside triphosphates and polyphosphorolysis of duplexes of DNA in the presence of one or more polyphosphorolyzing agents as described herein. Exemplary DNA polymerases having polyphosphorolysis activity include but are not limited to thermostable Tfl, Taq, and/or genetically engineered DNA polymerases (e.g., AMPLITAQFS, THERMOSEQUENASE), those having the active site mutation F667Y or the equivalent of F667Y (e.g., in Tth) which shows improved affinity for dideoxynucleotide as incoming nucleotide (e.g., smaller $K_m$ for ddNTP)), RQ1 as described in U.S. Pat. No. 7,422,872 and mutants thereof (e.g., RQY in which 669 is substituted by tyrosine, which may provide for reverse transcription and/or direct sequencing of RNA), THERMINATOR I (NEB), THERMINATOR II, THERMINATOR III, and/or THERMINATOR GAMMA (all available from NEB), among others. These and other potentially suitable DNA polymerases may be described in, for example, U.S. Pub. 2008/0254525A1, U.S. Pub. 2007/0020622A1, U.S. Pub. 2007/0009924A1, U.S. Pat. Nos. 4,889,818, 4,965,188, 5,047,342, 5,079,352, 5,270,179, 5,374,553, 5,436,149, 5,512,462, 5,614,365, and/or 6,228,628B1. It has been found that the use of such genetically engineered DNA polymerases may improve the efficiency of the removal of the non-extendable nucleotide from the nucleic acid, and can be followed by polymerization (extension) of the now-extendable oligonucleotide. The process of terminal nonextendable nucleotide removal by a polyphosphorolysis enzyme in the presence of one or more polyphosphorylyzing agents, followed by polymerization of the now extendable oligonucleotide may be referred to as Activation by Polyphosphorolysis (APP) reaction.

In some embodiments using APP, the one or more polyphosphorolyzing agents may be represented by Formula I:

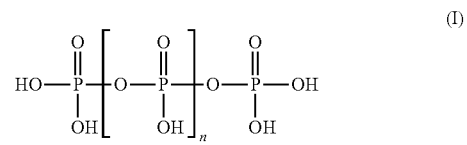

wherein n is, for example, 1, 2, 3, 4, 5, 6, 7, 8, 9, or 10, or more. In some embodiments, the one or more polyphosphorolyzing agents may be represented by Formula II:

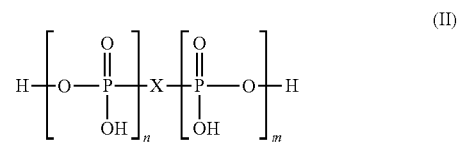

In some embodiments representing compounds of Formula II, n and/or m may be the same or different. And n and/or m may be, for example, 0, 1, 2, 3, 4, 5, 6, 7, 8, 9, or 10 with the proviso that n or m, but not both, may be 0. Thus, if n is 0, then m may be 1, 2, 3, 4, 5, 6, 7, 8, 9, or 10. If m is 0, then n may be 1, 2, 3, 4, 5, 6, 7, 8, 9, or 10. In some embodiments, n and m are both greater than or equal to 1. In some embodiments, n and m are both 1. In some embodiments, the sum of n+m is greater than or equal to 2 (e.g., n≥1 and m≥1, n≥2 and m≥0, n≥0 and m≥2). In some embodiments, such as where (but not limited to) the sum of n+m is greater than or equal to 2, X may be, for example,

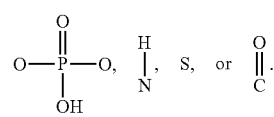

In some embodiments wherein the one or more polyphosphorolyzing agents are represented by Formula II, such as where (but not limited to) n or m=0, X may be, for example,

for example:

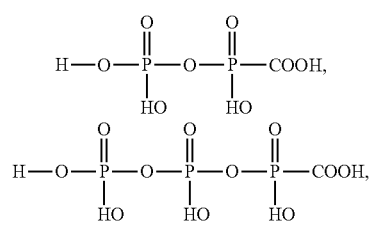

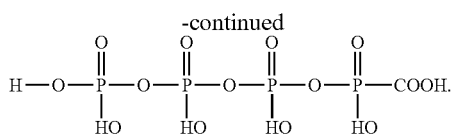

In some embodiments, the one or more polyphosphorolyzing agents may be:

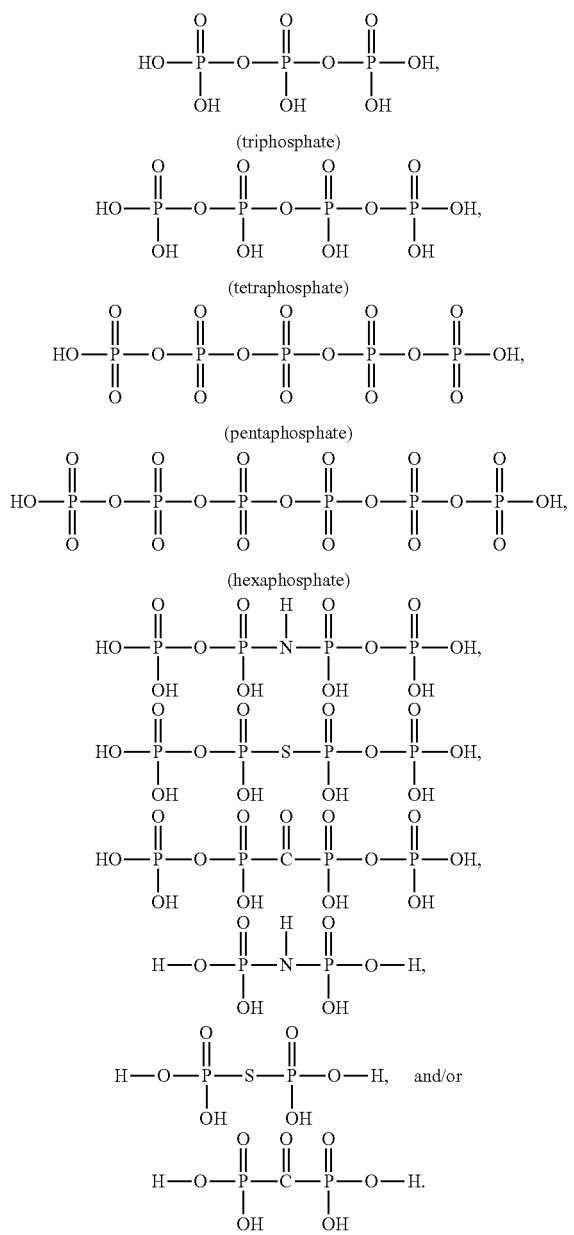

Any of the polyphosphorolyzing agents described herein may be combined with any other polyphosphorolyzing agents. In some embodiments, the one or more polyphosphorolyzing agents may be pyrophosphate ($PP_i$) in combination with at least one or more other polyphosphorolyzing agents. Any of the one or more polyphosphorolyzing agents may be used in the form of a salt (e.g., sodium). Typically, the APP reactions described herein further include one or more biocatalysts (e.g., enzyme(s)) having polyphosphorolysis activity to generate one or more nucleoside triphosphates. As shown above, for example, imidodiphosphate (IDP) links the phosphate moieties using nitrogen; similar diphosphate compounds may substitute sulfur for nitrogen. In some embodiments, a polyphosphate may be any phosphate ester having two or more phosphate moieties. In some embodiments, a polyphosphate may be any phosphate esters having three or more phosphate moieties.

The term "pyrophosphorolysis-activated polymerization" refers to a reaction that works in a reverse reaction to DNA polymerization and results in the removal of the 3'-terminal nucleotide of an annealed oligonucleotide. The removal of the 3'-terminal nucleotide is accomplished with a pyrophosphorolysis enzyme in the presence of pyrophosphate ($PP_i$), and is followed by polymerizing (extending) the now-extendable annealed oligonucleotide by a polymerase. It may also be referred to as "PAP".

As used herein, the term "pyrophosphorolysis enzyme" refers to any enzyme that can perform pyrophosphorolysis-activated polymerization reactions (for example, pyrophosphorolysis-activated polymerization chain reaction). The pyrophosphorolysis-activated polymerization method may be used to amplify either RNA or DNA. When used to amplify DNA, the activatable oligonucleotide may comprise a 2'-deoxyoligonucleotide (dN) and the non-extendible 3' terminus may comprise, for example, a 2',3'-didoxynucleotide (ddN) or an acyclonucleotide or other blockers as known in the art. The four nucleoside triphosphates may comprise 2'-deoxynucleoside triphosphates (dNTPs) or their analogs, and the nucleic acid polymerase may comprise a DNA polymerase. In certain embodiments, the DNA polymerase used may also have pyrophosphorolysis activity. Some DNA polymerases having pyrophosphorolysis activity are thermostable Tfl, Taq, and genetically engineered DNA polymerases, such as AMPLITAQFST™, available from Life Technologies (Carlsbad, Calif.) and THERMOSEQUENASE™, available from GE Healthcare Bio-Sciences Corp., (Piscataway, N.J.). These genetically engineered DNA polymerases have the mutation F667Y or an equivalent mutation in their active sites. The use of genetically engineered DNA polymerases, such as AMPLITAQFS™ and THERMOSEQUENASE™, can greatly improve the efficiency of pyrophosphorolysis-activated polymerization. These Family I DNA polymerases may be used according to certain embodiments of the methods disclosed herein when the activatable oligonucleotide comprises a dideoxynucleotide at the 3'-end or an acyclonucleotide at the 3'-end. When the activatable oligonucleotide is an acyclonucleotide, Family II archaeon DNA polymerases may be used. Examples of such polymerases include, but are not limited to, Vent (exo⁻) and Pfu (exo⁻). These polymerases efficiently amplify 3'-acyclonucleotide-blocked activatable oligonucleotides. In certain embodiments, two or more nucleic acid polymerases may also be used in one reaction. If the template is RNA, the nucleic acid polymerase may comprise RNA polymerase, reverse transcriptase, their variants, or a combination thereof. The activatable oligonucleotide may comprise a ribonucleotide or a 2'-deoxynucleotide. The non-extendible 3'-terminus of the oligonucleotide may comprise a dideoxyribonucleotide or an acyclonucleotide. The four nucleotide triphosphates may comprise ribonucleoside triphosphate, 2'-deoxynucleoside triphosphates, or their analogs. For convenience, the description that follows uses DNA as a template. Processing RNA however, is also well within the scope of the present teachings. Further details, uses and methods regarding these enzymes can be found in U.S. Pat. No. 7,033,763, which is incorporated herein by reference in its entirety.

The term "thermostable" when used in reference to an enzyme, refers to an enzyme (such as a polypeptide having nucleic acid polymerase activity) that is resistant to inactivation by heat. A "thermostable" enzyme or polymerase is in contrast to a "thermolabile" enzyme or polymerase, which can be inactivated by heat treatment. Thermolabile proteins can be inactivated at physiological temperatures, and can be categorized as mesothermostable (inactivation at about 45° C. to about 65° C.), and thermostable (inactivation at greater than about 65° C.). For example, the activities of the thermolabile T5 and T7 DNA polymerases can be totally inactivated by exposing the enzymes to a temperature of about 90° C. for about 30 seconds. A thermostable polymerase activity is more resistant to heat inactivation than a thermolabile polymerase. However, a thermostable polymerase does not mean to refer to an enzyme that is totally resistant to heat inactivation; thus heat treatment may reduce the polymerase activity to some extent. A thermostable polymerase typically will also have a higher optimum temperature than thermolabile DNA polymerases.

The term "working concentration" refers to the concentration of a reagent that is at or near the optimal concentration used in a solution to perform a particular function (such as amplification or digestion of a nucleic acid molecule). The working concentration of a reagent is also described equivalently as a "1× concentration" or a "1× solution" (if the reagent is in solution) of the reagent. Accordingly, higher concentrations of the reagent may also be described based on the working concentration; for example, a "2× concentration" or a "2× solution" of a reagent is defined as a concentration or solution that is twice as high as the working concentration of the reagent; a "5× concentration" or a "5× solution" is five times as high as the working concentration, and so on.

Oligonucleotides and Compositions/Reaction Mixtures:

In certain embodiments, oligonucleotides are provided that are specific for a particular allele or polymorphism. Such oligonucleotides are referred to herein as allele-specific primers or ASPs. Such allele-specific primers comprise an allele-specific portion and a 5'-universal tail; wherein the 5'-universal tail comprises a binding site for a universal FRET-based reporter primer (herein referred to as "UFP") and the universal tail is not complementary to the target nucleic acid sequence (see FIG. 1). In certain embodiments, the 5'-universal tail comprises a nucleotide sequence that is identical to the sequence of the universal FRET-based reporter primer. In certain embodiments, the 5'-universal tail comprises a nucleotide sequence that is complementary to the sequence of the universal FRET-based reporter primer. In certain embodiments, the 3'-end of the allele-specific primer is extendable by a nucleic acid polymerase enzyme. In certain embodiments, the 3' end of the allele-specific primer comprises a blocking agent such that the blocked end may be activated by a pyrophosphorolysis enzyme or a polyphosphorolysis enzyme. In certain embodiments, the blocking agent is a dideoxynucleotide (ddN). In certain embodiments, the allele-specific primer has a length of about 29 nucleotides to about 55 nucleotides. Preferably, the allele-specific primer has a length of about 35 nucleotides to about 50 nucleotides. Most preferably, the allele-specific primer has a length of about 43 nucleotides. In certain embodiments, the allele-specific portion has a $T_m$ of about 53° C. to about 65° C., preferably about 58° C. to about 62° C., most preferably about 59° C.

In certain embodiments, oligonucleotides are provided that is specific for a particular locus of the target nucleic acid. Such oligonucleotides are referred to herein as locus-specific primers or LSPs. In certain embodiments, the locus-specific primer may serve as a reverse primer in the amplification and genotyping methods disclosed herein. In certain embodiments, the 3'-end of the LSP comprises a blocking agent such that the blocked end may be activated by a polyphosphorolysis enzyme or a pyrophosphorolysis enzyme. In certain embodiments, the blocking agent is a dideoxynucleotide (ddN). In certain embodiments, the LSP may also be specific for a particular allele.

Figure 2:
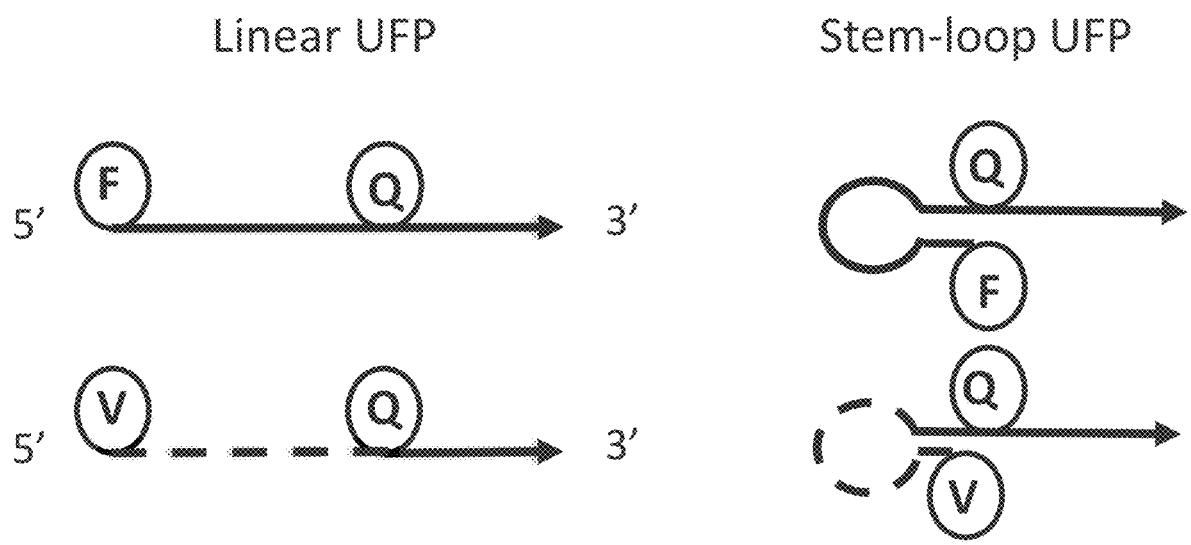
FIG. 2: A schematic representation of linear and stem-loop UFPs according to certain embodiments of the present teachings.

In certain embodiments, oligonucleotides are provided that may be used to detect the amplification of a target nucleic acid and/or may be used to monitor or detect the amplification of an allele or polymorphism in a target nucleic acid. Such oligonucleotides are referred to herein as universal FRET-based reporter primers (UFPs), wherein the universal FRET-based reporter primer comprises at least one quencher moiety located at an internal position of the UFP and a fluorophore attached to the 5'-end of the UFP (see FIG. 2). The fluorophore and at least one quencher may participate in FRET-based quenching. For example, when the UFP is not hybridized to the 5'-universal tail of the allele-specific primer or allele-specific primer extension product, the fluorescence of the fluorophore is quenched. However, upon hybridization of the UFP to its target sequence in the 5'-universal tail or the complement of the 5'-universal tail, the fluorescence of the fluorophore is no longer quenched and may be detected. In certain embodiments, the nucleotide sequence of the UFP is identical to the 5'-universal tail of the allele-specific primer. In certain embodiments, the nucleotide sequence of the UFP is complementary to the 5'-universal tail of the allele-specific primer. In certain embodiments, UFPs may be used to detect specific alleles (e.g., a first and second allele) or polymorphisms in a target nucleic acid, wherein a first allele-specific primer, which is specific for a first allele, comprises a first 5'-universal tail which comprises a binding site for a first UFP, wherein the first UFP comprises a first fluorophore and at least one quencher moiety; and a second allele-specific primer which is specific for a second allele, comprises a second 5'-universal tail which comprises a binding site for a second UFP, wherein the second UFP comprises a second fluorophore and at least one quencher moiety; wherein the first and second fluorophore are different and the at least one quencher moiety may be the same or different. In certain embodiments, a detectable signal is generated upon extension of the 3'-end of the UFP by a nucleic acid polymerase.

In certain embodiments, the UFP has a length of about 10 nucleotides to about 35 nucleotides. Preferably, the UFP has a length of about 15 nucleotides to about 35 nucleotides. Most preferably, the UFP has a length of about 25 nucleotides. In certain embodiments, the UFP has a $T_m$ of about 50° C. to about 75° C., preferably about 60° C. to about 70° C., most preferably about 58° C. In certain embodiments, the distance between the internal quencher moiety and the fluorophore at the 5'-end of the UFP is about 8 nucleotides to about 25 nucleotides. Preferably, the distance between the internal quencher moiety and the 5'-fluorophore is about 12 nucleotides to about 18 nucleotides, most preferably about 15 nucleotides. In certain embodiments, the UFP comprises one or more quencher moieties attached to one or more internal nucleotides. In certain embodiments, the UFP comprises at least two quencher moieties attached to at least two internal nucleotides. In certain embodiments, the UFP comprises two or more quencher moieties attached to two or more internal nucleotides. In certain embodiments, the UFP comprises a linear conformation (e.g., a linear UFP) (See FIG. 2). In certain embodiments, the UFP comprises a stem-loop or hairpin conformation (e.g., a stem-loop UFP) (See FIG. 2). In certain embodiments, the one or more internal quencher moieties are attached to one or more nucleotides located in one or more loop portions of the stem-loop UFP. In certain embodiments, the one or more internal quencher moieties are attached to one or more stem portions of the stem-loop UFP. In certain embodiments, the one or more internal quencher moieties are attached to one or more stem portions and one or more loop portions of the stem-loop UFP. In certain embodiments, the $T_m$ of the UFP may be lower than the $T_m$ of the ASP. In certain embodiments, the $T_m$ of the UFP may be lower than the $T_m$ of the LSP. In certain embodiments, the $T_m$ of the UFP may be lower than the $T_m$ of both the ASP and the LSP.

In certain embodiments, the 3'-end of the UFP comprises a blocking agent such that the blocked end may be activated by a polyphosphorolysis enzyme or a pyrophosphorolysis enzyme. In certain embodiments, the blocking agent is a dideoxynucleotide (ddN).

In certain embodiments, oligonucleotides are provided that may be used to detect the amplification of a target nucleic acid and/or may be used to monitor or detect the amplification of an allele or polymorphism in a target nucleic acid. Such oligonucleotides are referred to herein as "universal FRET-based detector probes", wherein the universal FRET-based detector probe comprises at least one quencher moiety at the 3'-end of the probe or at an internal position of the probe and a fluorophore attached to the 5'-end of the probe. In some embodiments, the at least one quencher moiety is attached to a nucleotide that is less than 10 nucleotides from the 5' end of the probe. In yet other embodiments the at least one quencher moiety is attached to a nucleotide that is less than 5 nucleotides from the 5' end of the probe. The fluorophore and at least one quencher may participate in FRET-based quenching. For example, when the universal FRET-based detector probe is not hybridized to the 5'-universal tail of the allele-specific primer or allele-specific primer extension product, the fluorescence of the fluorophore is quenched. However, upon hybridization of the UFP to its target sequence in the 5'-universal tail or the complement of the 5'-universal tail, the fluorescence of the fluorophore is no longer quenched and may be detected. The fluorescence may be further increased when the probe is digested by 5'-nuclease activity of polymerase.

The fluorophore and at least one quencher may participate in FRET-based quenching. For example, when the universal FRET-based detector probe is not hybridized to the 5'-universal tail of the allele-specific primer or allele-specific primer extension product, the fluorescence of the fluorophore is quenched. However, upon hybridization of the universal FRET-based detector probe to its target sequence in the 5'-universal tail or the complement of the 5'-universal tail, the fluorescence of the fluorophore is no longer quenched and may be detected. In certain embodiments, the nucleotide sequence of the universal FRET-based detector probe is identical to the 5'-universal tail of the allele-specific primer. In certain embodiments, the nucleotide sequence of the universal FRET-based detector probe is complementary to the 5'-universal tail of the allele-specific primer. In certain embodiments, universal FRET-based detector probe s may be used to detect specific alleles (e.g., a first and second allele) or polymorphisms in a target nucleic acid, wherein a first allele-specific primer, which is specific for a first allele, comprises a first 5'-universal tail which comprises a binding site for a first universal FRET-based detector probe, wherein the first universal FRET-based detector probe comprises a first fluorophore and at least a first quencher moiety; and a second allele-specific primer which is specific for a second allele, comprises a second 5'-universal tail which comprises a binding site for a second universal FRET-based detector probe, wherein the second universal FRET-based detector probe comprises a second fluorophore and at least a second quencher moiety; wherein the first and second fluorophore are different and the at least first quencher moiety and the at least second quencher moiety may be the same or different.

In certain embodiments, the universal FRET-based detector probe has a length of about 10 nucleotides to about 35 nucleotides. In some embodiments, the universal FRET-based detector probe has a length of about 15 nucleotides to about 35 nucleotides. In other embodiments, the universal FRET-based detector probe has a length of about 25 nucleotides. In certain embodiments, the universal FRET-based detector probe has a $T_m$ of about 50° C. to about 75° C., preferably about 60° C. to about 70° C., most preferably about 58° C. In certain embodiments, the distance between the quencher moiety and the fluorophore at the 5'-end of the universal FRET-based detector probe is about 8 nucleotides to about 25 nucleotides. Preferably, the distance between the quencher moiety and the 5'-fluorophore is about 12 nucleotides to about 18 nucleotides, most preferably about 15 nucleotides. In certain embodiments, the universal FRET-based detector probe comprises one or more quencher moieties attached to one or more nucleotides, some of which may be located internal to the 3' terminus of the universal FRET-based detector probe. In certain embodiments, the universal FRET-based detector probe comprises at least two quencher moieties attached to at least two internal nucleotides. In certain embodiments, the universal FRET-based detector probe comprises two or more quencher moieties attached to two or more internal nucleotides. In certain embodiments, the universal FRET-based detector probe comprises a linear conformation (e.g., a linear universal FRET-based detector probe). In certain embodiments, the universal FRET-based detector probe comprises a stem-loop or hairpin conformation (e.g., a stem-loop universal FRET-based detector probe). In certain embodiments, the one or more internal quencher moieties are attached to one or more nucleotides located in one or more loop portions of the stem-loop universal FRET-based detector probe. In certain embodiments, the one or more internal quencher moieties are attached to one or more stem portions of the stem-loop universal FRET-based detector probe. In certain embodiments, the one or more internal quencher moieties are attached to one or more stem portions and one or more loop portions of the stem-loop universal FRET-based detector probe. In certain embodiments, the $T_m$ of the universal FRET-based detector probe may be lower than the $T_m$ of the ASP. In certain embodiments, the $T_m$ of the universal FRET-based detector probe may be lower than the $T_m$ of the LSP. In certain embodiments, the $T_m$ of the universal FRET-based detector probe may be lower than the $T_m$ of both the ASP and the LSP.

Figure 9:
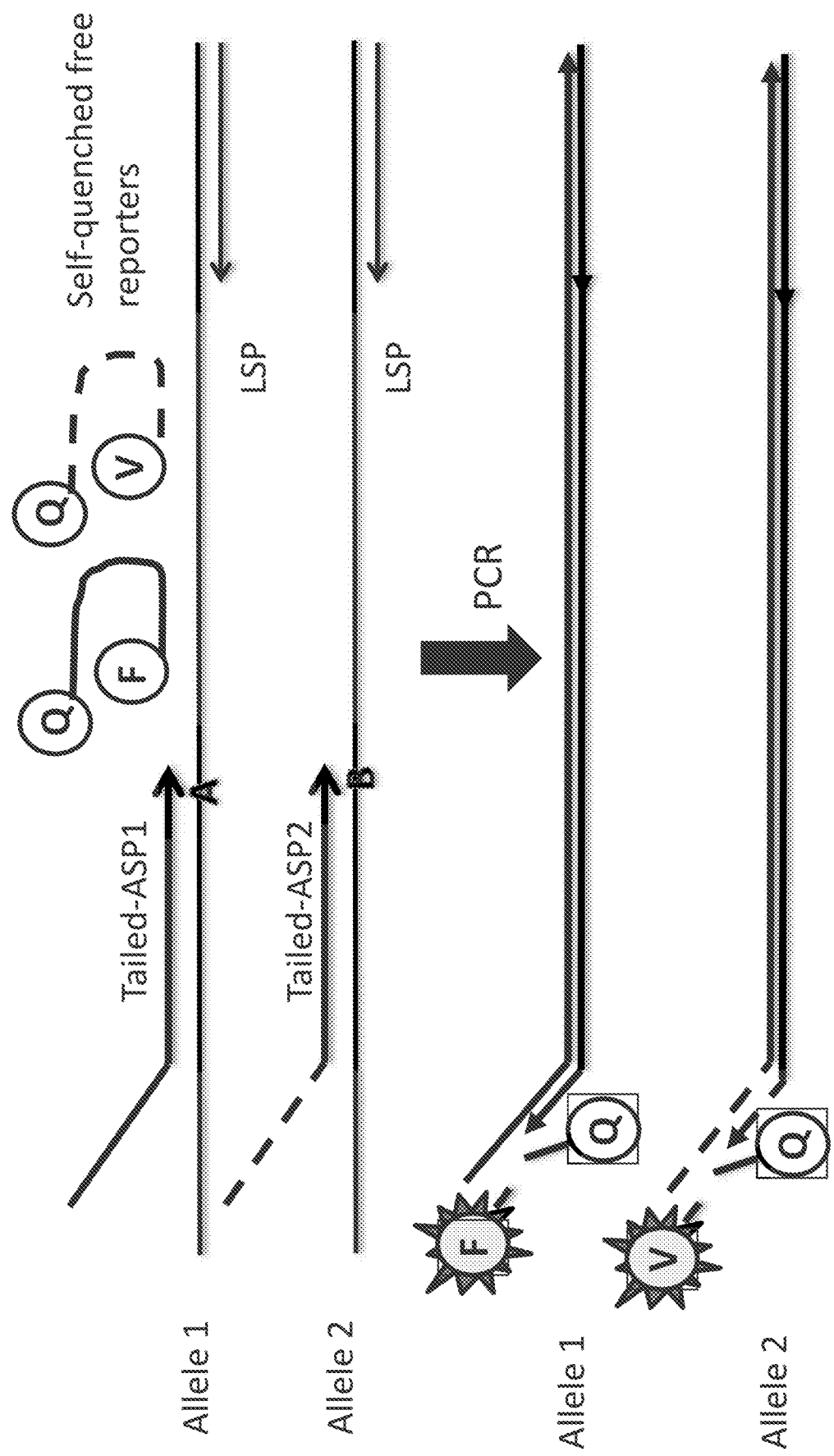
FIG. 9: A schematic for a universal FRET-based detector probe-based SNP assay, where the universal FRET-based detector probe replaces the UFP in the SNP assay, is shown including a universal detector probe, according to certain embodiments of the present teachings. An assay consists of a pair of allele-specific primers each including a universal tail (ASP1 and ASP2), a shared locus-specific reverse primer (LSP), and a pair of universal detector probes for each of the two alleles, each of which includes a fluorophore ("F" or "V") and a quencher ("Q"). The universal detector probe may have a linear or stem-loop conformation. In this embodiment, the universal detector probes are not extendable, but are digested during amplification. The universal FRET-based detector probe in the schematic lacks an arrow designation, and therefore is indicated as being not extendable.

An exemplary SNP assay where at least one universal FRET-based detector probe replaces the UFP is shown in FIG. 9. An assay may include a pair of allele-specific primers where each allele specific includes a universal tail (ASP1 and ASP2), a shared locus-specific reverse primer (LSP), and a pair of universal detector probes for each of the two alleles, each of which includes a fluorophore ("F" or "V") and a quencher ("Q"). The fluorophores "F" and "V" may be spectrally distinct. The at least one quencher moiety of the first and second universal detector probe may be the same or different. The universal tail of ASP 1 and ASP2 may differ from each other. The universal detector probe may have a linear or stem-loop conformation. In this embodiment, the universal detector probes are not extendable, but are digested during amplification. The presence and/or the amount of each of the alleles may be detected by detecting the distinct fluorescent signal of "F" and/or "V".

In certain embodiments, compositions and/or reaction mixtures are provided for analyzing, quantitating or detecting one or more alleles or polymorphisms in a target nucleic acid, wherein the composition and/or reaction mixture comprises one or more target nucleic acid molecules and a first allele-specific primer, which is specific for a first allele, comprising a first 5'-universal tail which comprises a binding site for a first UFP, wherein the first UFP comprises a first fluorophore and at least one quencher moiety; and a second allele-specific primer which is specific for a second allele, comprising a second 5'-universal tail which comprises a binding site for a second UFP, wherein the second UFP comprises a second fluorophore and at least one quencher moiety; wherein the first and second fluorophore are different and the at least one quencher moiety may be the same or different. In certain embodiments, the UFPs may be in a linear conformation. In certain embodiments, the UFPs may be in a stem-loop conformation. In certain embodiments, one UFP may be in a stem-loop conformation and the other UFP may be in a linear conformation. In certain embodiments, the composition and/or reaction mixture further comprises a locus specific primer. In certain embodiments, the composition and/or reaction mixture further comprises one or more nucleic acid polymerase, such as a thermostable polymerase; one or more reverse transcriptases, or any other DNA or RNA polymerase. In certain embodiments, the composition and/or reaction mixture comprises one or more pyrophosphorolysis enzyme. In certain embodiments, the composition and/or reaction mixture comprises one or more polyphosphorolysis enzyme and one or more polyphosphorolyzing agents. In certain embodiments, the reaction mixture and/or composition further comprises a universal FRET-based detector probe. In certain embodiments, the reaction mixture and/or composition further comprises one or more buffers or buffering salts; one or more nucleotides; one or more dideoxynucleotides (ddN); one or more target/template molecules (which may also be used for determining reaction performance, i.e., control reactions); and other reagents for analysis or further manipulation of the products or intermediates produced by the methods described herein.

Methods of Use:

In certain embodiments, methods are provided for determining the genotype of a target nucleic acid molecule comprising a SNP, the method comprising: (1) providing one or more target nucleic acid molecules and a first allele-specific primer, which is specific for a first allele, comprising a first 5'-universal tail which comprises a binding site for a first UFP, wherein the first UFP comprises a first fluorophore and at least one quencher moiety; and a second allele-specific primer which is specific for a second allele, comprising a second 5'-universal tail which comprises a binding site for a second UFP, wherein the second UFP comprises a second fluorophore and at least one quencher moiety; wherein the first and second fluorophore are different and the at least one quencher moiety may be the same or different; (2) providing a locus specific primer; (3) amplifying the target nucleic acids; (4) measuring the intensities of the first and the second fluorophore; (5) analyzing nucleic acid genotypes based on the intensities of the first and second fluorophores. In certain embodiments, the UFPs may be in a linear conformation. In certain embodiments, the UFPs may be in a stem-loop conformation. In certain embodiments, one UFP may be in a stem-loop conformation and the other UFP may be in a linear conformation.

In certain embodiments, the 3'-end of at least one of the allele-specific primers and/or locus-specific primer comprises a blocking agent such that the blocked end may be activated by pyrophosphorolysis or polyphosphorolysis. In certain embodiments, the blocking agent is a dideoxynucleotide (ddN). In certain embodiments, the LSP concentration is higher than that of the ASP. (See FIG. 10.)

In certain embodiments, one or more of the UFPs are replaced with one or more universal FRET-based detector probes wherein one end of the universal FRET-based detector probe comprises at least one quencher and the other end of the universal FRET-based detector probe comprises a fluorophore. The one or more universal FRET-based detector probes may be non-extendable. In certain embodiments, at least two universal FRET-based detector probes are used, wherein the first UFP is replaced by a first universal detector probe comprises at least one quencher moiety and a first fluorophore; and the second UFP is replaced with a second universal detector probe, wherein the universal detector probe comprises at least one quencher moiety and a second fluorophore; wherein the first and second fluorophores are different, and the at least one quencher moiety of the first and second universal detector probe may be the same or different. In some embodiments, the LSP concentrations are higher than that of the ASP.

Figure 10:
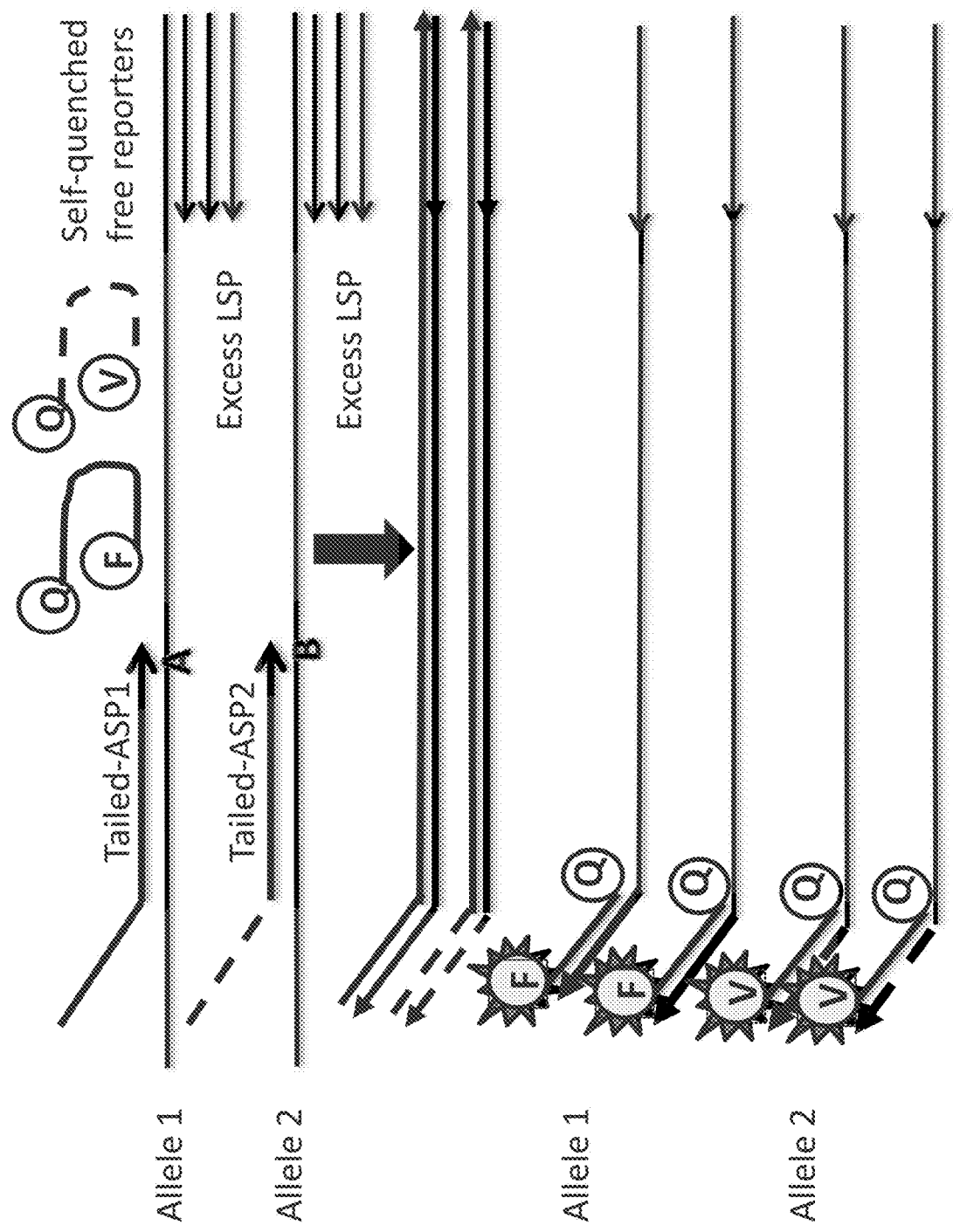
FIG. 10: A schematic for a universal FRET-based detector probe-based SNP assay, where the universal FRET-based detector probe replaces the UFP in the SNP assay, is shown including A-PCR according to certain embodiments of the present teachings. An assay consists of a pair of allele-specific primers each including a universal tail (ASP 1 and ASP2), an excess of the shared locus-specific reverse primer (LSP), and a pair of universal FRET-based detector probes for each of the two alleles, each of which includes a fluorophore ("F" or "V") and a quencher ("Q"). The universal FRET-based detector probes may have a linear or stem-loop conformation. The universal FRET-based detector probe in the schematic lacks an arrow designation, and therefore is indicated as being not extendable.

An exemplary scheme for an assay using two different universal FRET-based detector probes is shown in FIG. 10. An assay may include a pair of allele-specific primers each comprising a universal tail (ASP 1 and ASP2), an excess of the shared locus-specific reverse primer (LSP), and a pair of universal FRET-based detector probes, one each for each of the two alleles. The pair of universal FRET-based detector probes is not extendable, as shown in FIG. 10. The fluorophores "F" and "V" may be spectrally distinct. The at least one quencher moiety of the first and second universal detector probe may be the same or different. The universal FRET-based detector probe includes a fluorophore ("F" or "V") and a quencher ("Q"). The universal FRET-based detector probe may have a linear or stem-loop conformation. The presence and/or amount of the universal FRET-based detector probes are detected by detecting the fluorescence of "F" and/or "V", upon hybridization of the universal FRET-based detector probe(s) to the complementary tail of ASP1 and ASP2, respectively, which reduces the quenching effect of "Q".

Figure 11:
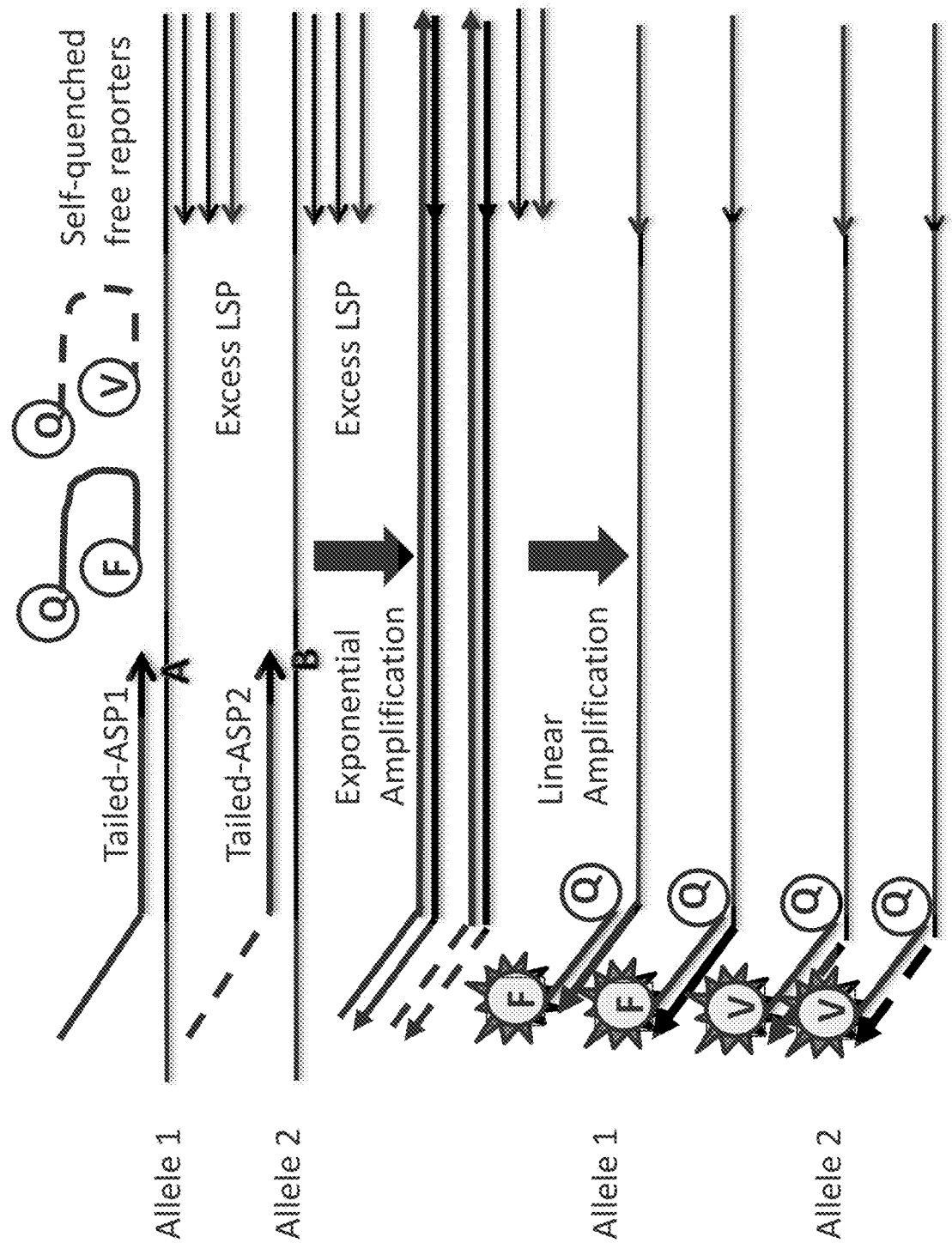
FIG. 11: A schematic for a universal reporter-based SNP assay, where the universal FRET-based detector probe replaces the UFP in the SNP assay, is shown including LATE-PCR according to certain embodiments of the present teachings. An assay consists of a pair of allele-specific primers each including a universal tail (ASP1 and ASP2), an excess of the shared locus-specific reverse primer (LSP), and a pair of universal FRET-based reporter probes for each of the two alleles, each of which includes a fluorophore ("F" or "V") and a quencher ("Q"). In the initial rounds of amplification, the amplification of the target nucleic acid is exponential. Subsequent amplification is linear. The universal FRET-based detector probes may have a linear or stem-loop conformation. The universal FRET-based detector probe in the schematic lacks an arrow designation, and therefore is indicated as being not extendable.

Another exemplary assay is represented in FIG. 11, which includes LATE-PCR. An assay may include a pair of allele-specific primers each comprising a universal tail (ASP 1 and ASP2), an excess of the shared locus-specific reverse primer (LSP), and a pair of universal FRET-based detector probes, one each for each of the two alleles. After exponential amplification with excess LSP, linear amplification is performed in the presence of the pair of universal FRET-based detector probes. The pair of universal FRET-based detector probes is not extendable, as shown in FIG. 11. The universal FRET-based detector probe includes a fluorophore ("F" or "V") and a quencher ("Q"). The fluorophores "F" and "V" may be spectrally distinct. The at least first quencher moiety of the first and the at least second quencher of the second universal detector probe may be the same or different. The universal FRET-based detector probe may have a linear or stem-loop conformation. The presence and/or amount of the universal FRET-based detector probes are detected by detecting the fluorescence of "F" and/or "V", upon hybridization of the universal FRET-based detector probe(s) to the complementary tail of ASP1 and ASP2, respectively, which reduces the quenching effect of "Q".

Figure 12:
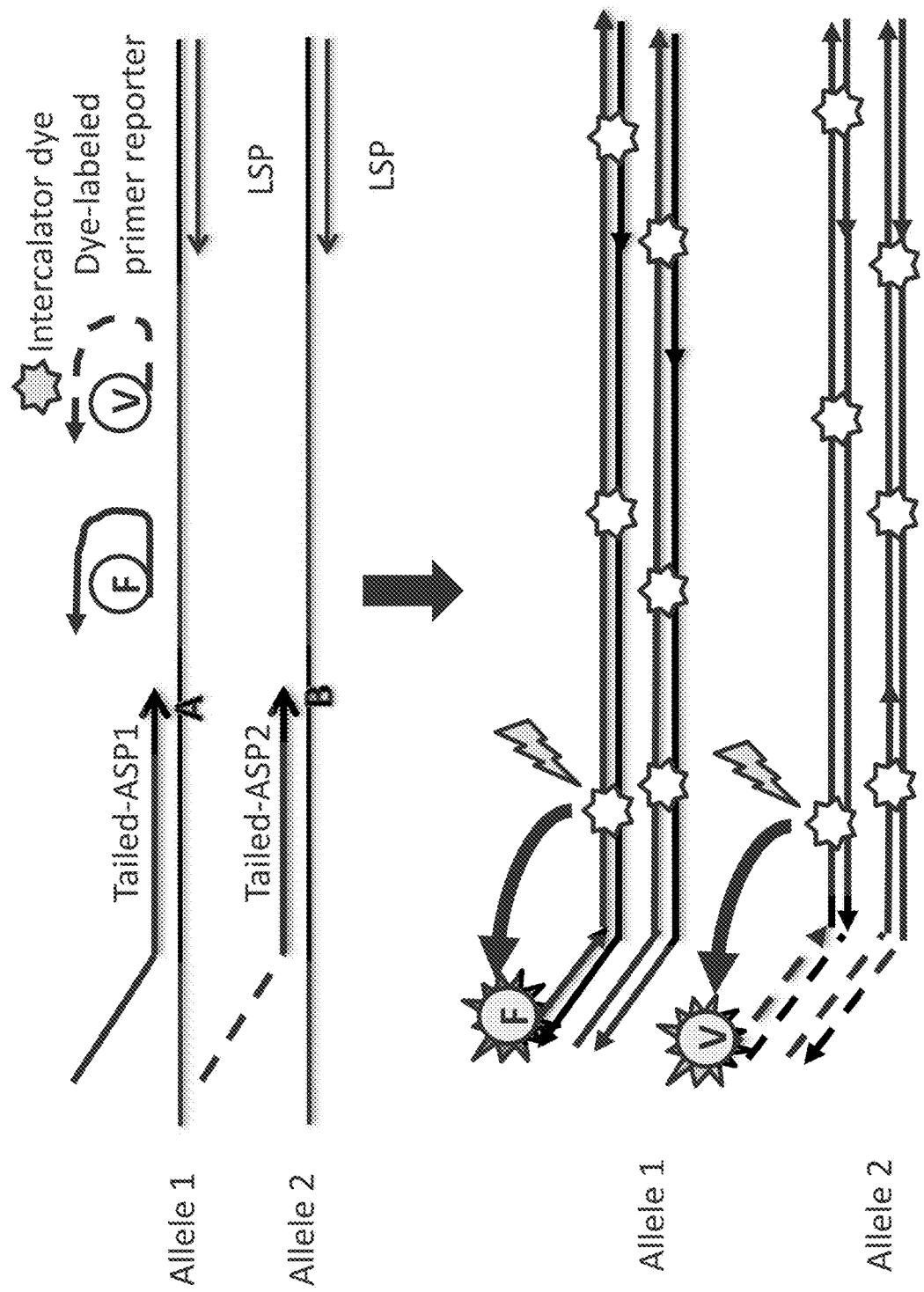
FIG. 12: A schematic for a UFP-based SNP assay including a double-stranded nucleic acid intercalator dye and a universal dye-labeled reporter primer according to certain embodiments of the present teachings. An assay consists of a pair of allele-specific primers each including a universal tail (ASP1 and ASP2), a shared locus-specific reverse primer (LSP), a double-stranded nucleic acid intercalator dye, and a pair of universal FRET-based reporter primers (herein denoted "dye-labeled reporter primer") for each of the two alleles, each of which includes a fluorophore ("F" or "V"). The universal dye-labeled reporter primers may have a linear or stem-loop conformation. As amplification proceeds, the intercalator dye is bound to the double-stranded amplification product and the dye-labeled reporter primer is incorporated into the amplification product. Upon excitation of the intercalator dye by an illumination source, the emitted light from the intercalator dye is used to excite the fluorophore of the dye-labeled reporter primer.

In certain embodiments, methods are provided for determining the genotype of a target nucleic acid molecule comprising a SNP, the method comprising: (1) providing one or more target nucleic acid molecules and a first allele-specific primer, which is specific for a first allele, comprising a first 5'-universal tail which comprises a binding site for a first UFP, wherein the first UFP comprises a first fluorophore; and a second allele-specific primer which is specific for a second allele, comprising a second 5'-universal tail which comprises a binding site for a second UFP, wherein the second UFP comprises a second fluorophore; wherein the first and second fluorophore are different and may not be directly excited by excitation light; (2) providing a locus specific primer; (3) providing a double-stranded nucleic acid intercalator dye; wherein the double-stranded nucleic acid intercalator dye is directly excited by the excitation light and its fluorescence excites the fluorophores in the UFPs; (4) amplifying the target nucleic acids; (5) measuring the intensities of the first and the second fluorophore; (6) analyzing nucleic acid genotypes based on the intensities of the first and second fluorophores (see, FIG. 12). In certain embodiments, the UFPs may be in a linear conformation. In certain embodiments, the UFPs may be in a stem-loop conformation. In certain embodiments, one UFP may be in a stem-loop conformation and the other UFP may be in a linear conformation. As amplification proceeds, the intercalator dye is bound to the double-stranded amplification product and the dye-labeled reporter primer is incorporated into the amplification product. Upon excitation of the intercalator dye by an illumination source, the emitted light from the intercalator dye is used to excite the fluorophore of the dye-labeled reporter primer.

Exemplary methods for polymerizing and/or amplifying nucleic acids include, for example, polymerase-mediated extension reactions. For instance, the polymerase-mediated extension reaction may be the polymerase chain reaction (PCR). In other embodiments, the nucleic acid amplification reaction may be a multiplex reaction. For instance, exemplary methods for polymerizing and/or amplifying and detecting nucleic acids suitable for use as described herein are commercially available as TaqMan® assays (see, e.g., U.S. Pat. Nos. 4,889,818; 5,079,352; 5,210,015; 5,436,134; 5,487,972; 5,658,751; 5,210,015; 5,487,972; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and/or 7,445,900, all of which are hereby incorporated herein by reference in their entirety). TaqMan® assays are typically carried out by performing nucleic acid amplification on a target polynucleotide using a nucleic acid polymerase having 5'-to-3' nuclease activity, a primer capable of hybridizing to the target polynucleotide, and an oligonucleotide probe capable of hybridizing to said target polynucleotide 3' relative to the primer. The oligonucleotide probe typically includes a detectable label (e.g., a fluorescent reporter molecule) and a quencher molecule capable of quenching the fluorescence of the reporter molecule. Typically, the detectable label and quencher molecule are part of a single probe. As amplification proceeds, the polymerase digests the probe to separate the detectable label from the quencher molecule. The detectable label (e.g., fluorescence) is monitored during the reaction, where detection of the label corresponds to the occurrence of nucleic acid amplification (e.g., the higher the signal the greater the amount of amplification). Variations of TaqMan® assays (e.g., LNA™ spiked TaqMan® assay) are known in the art and would be suitable for use in the methods described herein.

As used herein, the term "detector probe" refers to a molecule used in an amplification reaction, typically for quantitative or real-time PCR analysis, as well as end-point analysis. Such detector probes may be used to monitor the amplification of the target polynucleotide. In some embodiments, detector probes present in an amplification reaction are suitable for monitoring the amount of amplicon(s) produced as a function of time. Such detector probes include, but are not limited to, the 5'-exonuclease assay (TaqMan® probes described herein (see also U.S. Pat. No. 5,538,848) various stem-loop molecular beacons (see e.g., U.S. Pat. Nos. 6,103,476 and 5,925,517 and Tyagi and Kramer, *Nature Biotechnology* 14:303-308 (1996)), stemless or linear beacons (see, e.g., PCT Publication No. WO 99/21881), PNA Molecular Beacons™ (see, e.g., U.S. Pat. Nos. 6,355,421 and 6,593,091), linear PNA beacons (see, e.g., Kubista et al., *SPIE* 4264:53-58 (2001)), non-FRET probes (see, e.g., U.S. Pat. No. 6,150,097), Sunrise/Amplifluor® probes (U.S. Pat. No. 6,548,250), stem-loop and duplex Scorpion™ probes (Solinas et al., *Nucleic Acids Research* 29:E96 (2001) and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., *Methods* 25:463-471 (2001); Whitcombe et al., *Nature Biotechnology*, 17:804-807 (1999); Isacsson et al., *Molecular Cell Probes*, 14:321-328 (2000); Svanvik et al., *Anal Biochem*. 281:26-35 (2000); Wolffs et al., *Biotechniques* 766:769-771 (2001); Tsourkas et al., *Nucleic Acids Research*, 30:4208-4215 (2002,); Riccelli et al., *Nucleic Acids Research* 30:4088-4093 (2002); Zhang et al., *Shanghai*. 34:329-332 (2002); Maxwell et al., *J. Am. Chem. Soc*. 124:9606-9612 (2002); Broude et al., *Trends Biotechnol*. 20:249-56 (2002); Huang et al., *Chem. Res. Toxicol*. 15:118-126 (2002); and Yu et al., *J. Am. Chem. Soc* 14:11155-11161 (2001). Detector probes may also comprise quenchers, including without limitation black hole quenchers (Biosearch), Iowa Black (IDT), QSY quencher (Molecular Probes), and Dabsyl and Dabcel sulfonate/carboxylate Quenchers (Epoch). Detector probes may also comprise two probes, wherein for example a fluor is on one probe, and a quencher is on the other probe, wherein hybridization of the two probes together on a target quenches the signal, or wherein hybridization on the target alters the signal signature via a change in fluorescence. Detector probes may also comprise sulfonate derivatives of fluorescein dyes with $SO_3$ instead of the carboxylate group, phosphoramidite forms of fluorescein, phosphoramidite forms of Cy5 (commercially available for example from GE Healthcare). In some embodiments, intercalating labels are used such as ethidium bromide, SYBR® Green I, SYBR® GreenER™, and PicoGreen® (Life Technologies Corp., Carlsbad, Calif.), thereby allowing visualization in real-time, or end point, of an amplification product in the absence of a detector probe. In some embodiments, real-time visualization may comprise both an intercalating detector probe and a sequence-based detector probe. In some embodiments, the detector probe is at least partially quenched when not hybridized to a complementary sequence in the amplification reaction, and is at least partially unquenched when hybridized to a complementary sequence in the amplification reaction. In some embodiments, the detector probes of the present teachings have a $T_m$ of about 63° C. to about 69° C., though it will be appreciated that guided by the present teachings routine experimentation can result in detector probes with other $T_m$s. In some embodiments, probes may further comprise various modifications such as a minor groove binder (see for example U.S. Pat. No. 6,486,308) to further provide desirable thermodynamic characteristics.

Another exemplary system suitable for use as described herein utilizes double-stranded probes in displacement hybridization methods (see, e.g., Morrison et al. *Anal. Biochem.*, 18:231-244 (1989); and/or Li, et al. *Nucleic Acids Res.*, 30(2,e5) (2002)). In such methods, the probe typically includes two complementary oligonucleotides of different lengths where one includes a detectable label and the other includes a quencher molecule. When not bound to a target nucleic acid, the quencher suppresses the signal from the detectable label. The probe becomes detectable upon displacement hybridization with a target nucleic acid. Multiple probes may be used, each containing different detectable labels, such that multiple target nucleic acids may be queried in a single reaction.

Additional exemplary methods for polymerizing and/or amplifying and detecting target nucleic acids suitable for use as described herein involve "molecular beacons", which are single-stranded hairpin-shaped oligonucleotide probes. In the presence of the target sequence, the probe unfolds, binds and emits a signal (e.g., fluoresces). A molecular beacon typically includes at least four components: 1) the "loop", an 18-30 nucleotide region which is complementary to the target sequence; 2) two 5-7 nucleotide "stems" found on either end of the loop and being complementary to one another; 3) at the 5' end, a detectable label; and 4) at the 3' end, a quencher moiety that prevents the detectable label from emitting a single when the probe is in the closed loop shape (e.g., not bound to a target nucleic acid). Thus, in the presence of a complementary target, the "stem" portion of the beacon separates out resulting in the probe hybridizing to the target. Other types of molecular beacons are also known and may be suitable for use in the methods described herein. Molecular beacons may be used in a variety of assay systems. One such system is nucleic acid sequence-based amplification (NASBA®), a single step isothermal process for polymerizing and/or amplifying RNA to double stranded DNA without temperature cycling. A NASBA reaction typically requires avian myeloblastosis virus (AMV), reverse transcriptase (RT), T7 RNA polymerase, RNase H, and two oligonucleotide primers. After amplification, the amplified target nucleic acid may be detected using a molecular beacon. Other uses for molecular beacons are known in the art and would be suitable for use in the methods described herein.

The Scorpions™ system is another exemplary assay format that may be used in the methods described herein. Scorpions™ primers are bi-functional molecules in which a primer is covalently linked to the probe, along with a detectable label (e.g., a fluorophore) and a non-detectable quencher moiety that quenches the fluorescence of the detectable label. In the presence of a target nucleic acid, the detectable label and the quencher separate which leads to an increase in signal emitted from the detectable label. Typically, a primer used in the amplification reaction includes a probe element at the 5' end along with a "PCR blocker" element (e.g., a hexaethylene glycol (HEG) monomer (Whitcombe, et al. *Nat. Biotech.* 17: 804-807 (1999)) at the start of the hairpin loop. The probe typically includes a self-complementary stem sequence with a detectable label at one end and a quencher at the other. In the initial amplification cycles (e.g., PCR), the primer hybridizes to the target and extension occurs due to the action of polymerase. The Scorpions™ system may be used to examine and identify point mutations using multiple probes that may be differently tagged to distinguish between the probes. Using PCR as an example, after one extension cycle is complete, the newly synthesized target region will be attached to the same strand as the probe. Following the second cycle of denaturation and annealing, the probe and the target hybridize. The hairpin sequence then hybridizes to a part of the newly produced PCR product. This results in the separation of the detectable label from the quencher and causes emission of the signal. Other uses for such labeled probes are known in the art and would be suitable for use in the methods described herein.

In certain embodiments, a melting curve analysis is performed on double-stranded DNA samples resulting from real-time PCR in a target DNA region in which a mutation or SNP of interest lies. The analysis may comprise an HRM analysis. A warming of the amplicon DNA from around 50° C. to around 95° C. causes the two strands of DNA to melt and the dissociation may be characteristically measured. In practice, the melting process is monitored at high resolution and in real-time. In certain embodiments, a fluorescent dye may be used as an indicator of the dissociation. In certain embodiments, in a measurement of the melt of a double-stranded DNA, an intercalating dye may be used that binds specifically to double-stranded DNA and fluoresces at a characteristic and measurable level as long as binding to the double-stranded DNA is maintained. At the melting temperature for a particular double-stranded entity, the fluorescence changes. For example, a high level of fluorescence indicates a population of double-stranded entities in the sample, as the temperature rises the two strands of the double-stranded DNA separate and the fluorescence changes accordingly. High resolution detection of the melting event yields a melting curve and a melting temperature ($T_m$) that shows the change in fluorescence as a function of temperature. According to certain embodiments, the detection may be used to reveal differences in sequence variants, for example, to determine if a sample is homozygous for a first allele of a gene, homozygous for a second allele of the gene, or heterozygous.

In certain embodiments, methods for amplifying allele-specific target nucleic acids include activation by polyphosphorolysis (APP) reactions to provide highly-specific amplification of the target RNA or cDNA thereof. In certain embodiments, the polyphosphorolysis-activatable oligonucleotide (APP oligonucleotide) is an allele-specific oligonucleotide with a dideoxynucleotide at the 3' terminus. The 3' terminal dideoxynucleotide inhibits direct extension by polymerase but can be removed by polyphosphorolysis in the presence of a polyphosphorolyzing agent and the complementary strand of the target. Generally, the dideoxynucleotide is not removed if there is a mismatch between the APP oligonucleotide and its hybridization partner. Typically, the APP oligonucleotide is designed to have a nucleotide which distinguishes one target from another, for example, a major allelic DNA target sequence from a minor allelic DNA target sequence, near the 3' end. APP may be used to polymerize and/or amplify nucleic acid molecules, including but not limited to ribonucleic acid (e.g., RNA) and/or deoxyribonucleic acid (e.g., DNA), or hybrids thereof. APP reactions and such uses thereof are described in U.S. Ser. No. 13/324,676, filed Dec. 13, 2011 and published as U.S. Pat. Pub. No. 2012/0196329, herein incorporated by reference in its entirety.

APP provides for the extension of oligonucleotides by converting a non-extendable oligonucleotide into an extendable oligonucleotide, extending the oligonucleotide to produce a desired nucleic acid strand (e.g., a complementary copy of a target nucleic acid), and optionally amplifying and detecting the desired nucleic acid strand. A non-extendable nucleotide refers to a nucleotide, which upon incorporation into a nucleic acid prevents further extension of the nucleic acid, e.g., by at least one biocatalyst (e.g., enzyme). A nucleotide may be extendable by one enzyme, but non-extendable by another enzyme. A non-extendable nucleotide to one enzyme could become extendable or partially extendable under different conditions. An extendable nucleotide may refer to a nucleotide to which at least one other nucleotide can be added or covalently bonded at a 3'-position of the sugar moiety of the extendable nucleotide by a biocatalyst (e.g., enzyme) present in the reaction. Extension may also start from 2'-OH of a nucleotide which may or may not have an extendable 3'-OH. Extending a nucleic acid refers to the addition of or incorporation of one or more nucleotides to or into a given nucleic acid. An extended oligonucleotide is typically an oligonucleotide (e.g., a primer nucleic acid) to which one or more additional nucleotides have been added or otherwise incorporated (e.g., covalently bonded to). APP is typically carried out using the steps of: (a) annealing to a nucleic acid a first oligonucleotide which has a non-extendable 3' end ("P*") that is removable by polyphosphorolysis (i.e., activatable); (b) removing that 3' non-extendable terminus using a polyphosphorolyzing agent and an enzyme (i.e., a DNA polymerase) having polyphosphorolysis activity to produce an unblocked oligonucleotide; and, (c) extending the unblocked oligonucleotide to produce a desired nucleic acid strand. Further steps of detecting the desired nucleic acid strand may also be included as described below.

The one or more polyphosphorolyzing agents may be included in the reaction mixture at any suitable concentration. For instance, a suitable concentration may be approximately 1-500 µM. Other suitable polyphosphorolyzing agent concentrations ranges may include but are not limited to approximately 1-10 µM, 10-20 µM, 20-30 µM, 30-40 µM, 40-50 µM, up to 50 µM, 50-60 M, 60-70 µM, 70-80 µM, 90-100 µM, up to 100 µM, 100-150 µM, 150-200 µM, up to 200 µM, 200-250 µM, 250-300 µM, up to 300 µM, 300-350 µM, 350-400 µM, up to 400 µM, 400-450 µM, 450-500 µM. Additionally suitable polyphosphorolyzing agent concentrations include but are not limited to 1 µM, 5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 125 µM, 150 µM, 175 µM, 200 µM, 225 µM, 250 µM, 275 µM, 300 µM, 325 µM, 350 µM, 375 µM, 400 µM, 425 µM, 450 µM, 475 µM, and 500 µM. Particularly suitable concentrations of polyphosphorolyzing agent(s) may include but are not limited to approximately 25 µM, 40 µM, 50 µM, and 100 µM, 150 µM, 200 µM and 250 µM. Other suitable concentrations of polyphosphorolyzing agent may also be suitable as would be understood by one of skill in the art, and are also contemplated to be part of this description.

The methods using APP described herein may be carried out in any of several different forms. In some embodiments, the method comprises the following steps carried out serially:

(a) Annealing to the template strand a complementary activatable oligonucleotide "P*". This activatable oligonucleotide has a non-extendable nucleotide at its 3' terminus. It has no nucleotides at or near its 3' terminus that mismatch the corresponding nucleotides on the template strand. Therefore, the terminal nucleotide is hybridized to the template strand when the oligonucleotide P* is annealed.

(b) Polyphosphorolyzing the annealed activatable oligonucleotide P* with at least one polyphosphorolyzing agent described herein and an enzyme that has polyphosphorolysis activity. This activates the oligonucleotide P* by removal of the hybridized terminal nucleotide.

(c) Polymerizing by extending the activated oligonucleotide P* on the template strand in presence of four nucleoside triphosphates and a nucleic acid polymerase to synthesize the desired nucleic acid strand.

The APP method may also be used to amplify a desired nucleic acid strand by, for example, adding the following additional steps: (d) separating the desired nucleic acid strand of step (c) from the template strand, and (e) repeating steps (a)-(d) until a desired level of amplification of the desired nucleic acid strand is achieved. Steps (a) to (c) of APP can be conducted sequentially as two or more temperature stages on a thermocycler, or they can be conducted as one temperature stage on a thermocycler.

As described above, APP may be used to amplify nucleic acid molecules, including but not limited to ribonucleic acid (e.g., RNA) and/or deoxyribonucleic acid (e.g., DNA). When used to amplify DNA, the non-extendable, activatable oligonucleotide P* is typically a 2'-deoxyoligonucleotide, the terminal deoxynucleotide may be a 2',3'-dideoxynucleotide, the four nucleoside triphosphates are 2'-deoxynucleoside triphosphates, and the nucleic acid polymerase is a DNA polymerase. The DNA polymerase used in step (c) can also be the enzyme having polyphosphorolysis activity used in step (b). Amplification by APP may be linear or exponential. Linear amplification is obtained when the activatable oligonucleotide P* is the only complementary oligonucleotide used. Exponential amplification is obtained when a second oligonucleotide is present that is complementary to the desired nucleic acid strand (e.g., as in PCR). The second oligonucleotide can either be an extendable or an activatable non-extendable oligonucleotide. The activatable oligonucleotide P* and the second oligonucleotide flank the region that is targeted for amplification. In step (a), the second oligonucleotide anneals to the separated desired nucleic acid strand product of step (d). In step (c), polymerization extends the second oligonucleotide on the desired nucleic acid strand to synthesize a copy of the nucleic acid template strand. In step (d), the synthesized nucleic acid template strand is separated from the desired nucleic acid strand. Steps (a) through (d) may then be repeated until the desired level exponential amplification has been achieved.

In certain embodiments, the APP method is used to amplify allele-specific target nucleic acid, which may be a DNA sequence. The activatable (e.g., non-extendable) oligonucleotide P* has no mismatches near the 3' terminus of the target allele specific-DNA sequence and has at least one nucleotide at or near its 3' terminus that mismatches the corresponding nucleotide of the non-target alternative allele specific DNA sequence. Because of the mismatch, in step (a) of the APP method the terminal non-extendable nucleotide of oligonucleotide P* is not hybridized to the non-target allele-specific DNA. In step (b), polyphosphorolysis does not substantially remove the non-hybridized terminal or near terminal nucleotide from the activatable oligonucleotide P* annealed to the non-target DNA. In step (c), therefore, the oligonucleotide P* is not substantially extended by polymerization on the non-target DNA. As a result, the desired nucleic acid strand of the target allele-specific DNA synthesized on the template strand is amplified preferentially over any nucleic acid strand synthesized on the non-target allele-specific DNA. In one embodiment, the APP method is used for exponential amplification of a specific (target) DNA species in a mixture containing one or more other (non-target) DNA species.

In certain embodiments, the provided methods to amplify allele-specific target nucleic acid comprise the step of target nucleic acid amplification using activation by polyphosphorolysis (APP) in the presence of at least one polyphosphorolyzing agent. In certain embodiments, the at least one polyphosphorolyzing agent is a diphosphate, a triphosphate, a tetraphosphate, a pentaphosphate or a hexaphosphate. In certain embodiments of the provided methods, the polyphosphorolyzing agent is triphosphate. In certain embodiments of the provided methods, the polyphosphorolyzing agent is hexaphosphate.

In certain embodiments, methods for amplifying target nucleic acids use activation by pyrophosphorolysis-activated polymerization (PAP) reactions. PAP may be used to polymerize and/or amplify nucleic acid molecules, including but not limited to ribonucleic acid (e.g., RNA) and/or deoxyribonucleic acid (e.g., DNA), or hybrids thereof. PAP reactions and uses thereof in polymerization and amplification reactions is described, for example, in U.S. Pat. No. 7,033,763, herein incorporated by reference in its entirety. In PAP, the annealed activatable oligonucleotide P* is pyrophosphorolyzed with pyrophosphate and an enzyme that exhibits pyrophosphorolyzing activity. This activates the oligonucleotide P* by removal of the hybridized non-extendible 3' terminus. Accordingly, in certain embodiments, amplification of the target miRNA cDNA uses PAP and pyrophosphate as the pyrophosphorolyzing agent.

In certain embodiments, for target nucleic acid amplification reactions using APP or PAP, one or more of a first allele specific primer (ASP1), a second allele-specific primer (ASP2), a locus-specific primer (LSP), a first universal FRET-based reporter primer (URP), a second universal FRET-based reporter primer (URP), one or more universal FRET-based detector probes may include a non-extendable nucleotide at the 3' terminus, which is activatable upon using APP or PAP. In certain embodiments, for target nucleic acid amplification reactions using APP or PAP, both a first universal FRET-based reporter primer (URP), a second universal FRET-based reporter primer (URP) comprises a non-extendable nucleotide at the 3' terminus, which is activatable upon using APP or PAP. In certain embodiments, for target nucleic acid amplification reactions using APP or PAP, both a first universal FRET-based detector probe that is selectively hybridizable to the tail of the first allele specific primer (ASP1) and a second universal FRET-based detector probe that is selectively hybridizable to the tail of the second allele-specific primer (ASP2) may include a non-extendable nucleotide at the 3' terminus, which is activatable upon using APP or PAP.

Figure 8:
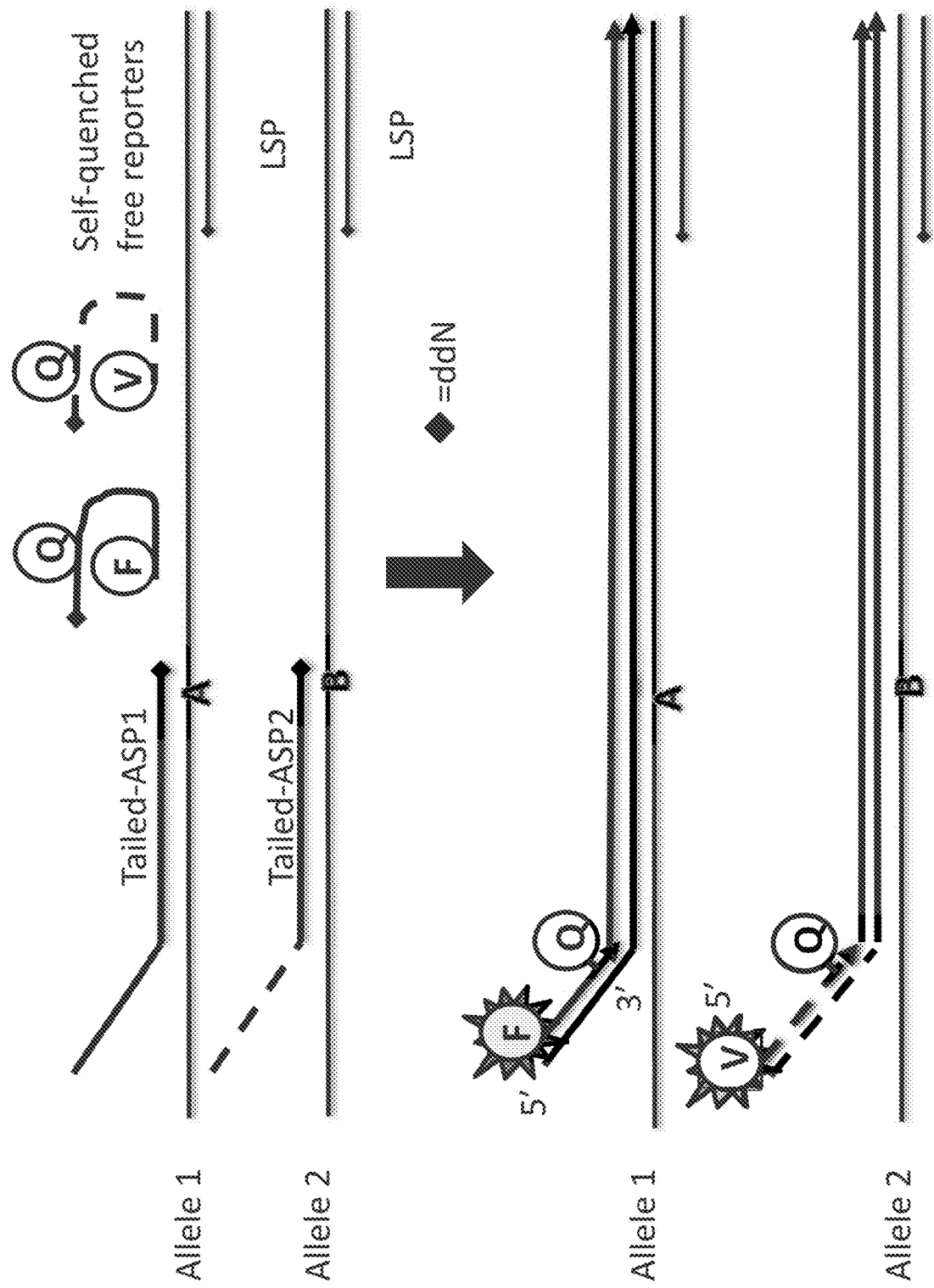
FIG. 8: A schematic for a UFP-based SNP assay including a pyrophosphorolysis or polyphosphorolysis step according to certain embodiments of the present teachings. An assay consists of a pair of allele-specific primers each including a universal tail and a 3'-ddN (ASP1 and ASP2), a shared locus-specific reverse primer (LSP), and a pair of universal FRET-based reporter primers (UFPs) for each of the two alleles, each of which includes a fluorophore ("F" or "V") and a quencher ("Q"). The UFPs may have a linear or stem-loop conformation. The tailed ASP 1, tailed ASP2, LSP and universal FRET-based detector probes in the schematic each have a diamond designation at their respective 3' ends, and therefore are indicated as being not extendable without a pyrophosphorolysis or polyphosphorolysis activation step.

One exemplary, but not limiting assay utilizing APP or PAP is shown in FIG. 8. A schematic for a universal FRET-based detector probe SNP assay comprising a pyrophosphorolysis or polyphosphorolysis step is shown. The assay includes a pair of allele-specific primers each comprising a universal tail and a 3'-ddN (ASP1 and ASP2), a shared locus-specific reverse primer (LSP), and a pair of FRET-based detector probes, one for each of the two alleles, each of the pair of universal FRET-based detector probes includes a fluorophore ("F" or "V") and a quencher ("Q"). The universal FRET-based detector probes may have a linear or stem-loop conformation. Each of ASP1, ASP2, LSP, and the universal FRET-based detector probes, as indicated in FIG. 8 having no arrow designation, are not extendable without APP or PAP. The diamond designation indicates its ability to be activated by APP or PAP. In other embodiments, the pair of universal FRET-based detector probes each have a 3"ddN and are not extendable without APP or PAP and may be used in any combination with any of ASP1, ASP2, or LSP which may be extendable or nonexpendable (i.e. have a 3' ddN, which are extendable with APP or PAP).

According to certain embodiments, allele-specific pyrophosphorolysis-activated polymerization or allele-specific activation by polyphosphorolysis with allele-specific primers with a universal tail or primers having other nucleotide alterations, followed by melting curve analysis, provides an assay that may be applied to the analysis of most, and in many instances all, SNPs, not just a subset of SNPs. The resolution of a SNP assay may be greatly increased by adjusting allele specificity to the length and sequence of a desired PCR amplicon.

According to certain embodiments, an HRM assay may be used in a quantitative way, e.g., for allele-quantification of SNPs, because the melt curves of the two allele-specific amplicons are clearly separated. According to certain embodiments, the high specificity of pyrophosphorolysis-activated polymerization (PAP) or activation by polyphosphorolysis (APP) may be used to greatly reduce the risk of non-specific PCR amplification and to increase specificity as well as sensitivity of HRM assays.

According to certain embodiments, HRM-based sequence analysis is used as a powerful technology for SNP genotyping and mutation scanning Allele-specific pyrophosphorolysis-activated polymerization or polyphosphorolysis-activated polymerization with universal tailed primers or primers having other nucleotide alterations followed by HRM analysis according to certain embodiments of the present teachings, converts an HRM platform into a robust and quantitative mutation screening platform capable of analyzing any SNP. An increased allele-specific resolution between PCR amplicons allows quantitative genotyping applications like allele quantitation or allele specific gene expression analysis. The present robust assay platform described herein may be used in assays for clinical research as well as for diagnostic applications.

In some embodiments, the methods are performed before or in conjunction with a sequencing reaction. The term "sequencing" is used in a broad sense herein and refers to any technique known in the art that allows the order of at least some consecutive nucleotides in at least part of a polynucleotide, for example but not limited to a target nucleic acid or an amplicon, to be identified. Some non-limiting examples of sequencing techniques include Sanger's dideoxy terminator method and the chemical cleavage method of Maxam and Gilbert, including variations of those methods; sequencing by hybridization; sequencing by synthesis; and restriction mapping. Some sequencing methods comprise electrophoresis, including capillary electrophoresis and gel electrophoresis; sequencing by hybridization including microarray hybridization; mass spectrometry; single molecule detection; and ion/proton detection. In some embodiments, sequencing comprises direct sequencing, duplex sequencing, cycle sequencing, single base extension sequencing (SBE), solid-phase sequencing, or combinations thereof. In some embodiments, sequencing comprises detecting the sequencing product using an instrument, for example but not limited to an ABI Prism® 377 DNA Sequencer, an ABI Prism® 310, 3100, 3100-Avant, 3730 or 3730×1 Genetic Analyzer, an ABI Prism® 3700 DNA Analyzer, an Ion PGM™ sequencer, or an Ion Proton™ sequencer (all available from Life Technologies Corp., Carlsbad, Calif.), or a mass spectrometer. In some embodiments, sequencing comprises incorporating a dNTP, including a dATP, a dCTP, a dGTP, a dTTP, a dUTP, a dITP, or combinations thereof, and including dideoxyribonucleotide analogs of dNTPs, into an amplification product.

In certain embodiments of the methods, compositions and kits disclosed herein, one or more nucleic acid polymerase may be used. The nucleic acid polymerases that may be employed in the disclosed nucleic acid amplification reactions may be any that function to carry out the desired reaction including, for example, a prokaryotic, fungal, viral, bacteriophage, plant, and/or eukaryotic nucleic acid polymerase. As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'-to-3' direction. Since DNA polymerase can only add a nucleotide onto a pre-existing 3'-OH group, to begin a DNA synthesis reaction, the DNA polymerase needs a primer to which it can add the first nucleotide. Suitable primers may comprise oligonucleotides of RNA or DNA, or chimeras thereof (e.g., RNA/DNA chimerical primers). The DNA polymerases may be a naturally occurring DNA polymerases or a variant of natural enzyme having the above-mentioned activity. For example, it may include a DNA polymerase having a strand displacement activity, a DNA polymerase lacking 5'-to-3' exonuclease activity, a DNA polymerase having a reverse transcriptase activity, a DNA polymerase having an endonuclease activity, or a DNA polymerase having a pyrophosphorolysis activated polymerase or polyphosphorolysis-activated polymerase activity.

Suitable nucleic acid polymerases may also comprise holoenzymes, functional portions of the holoenzymes, chimeric polymerase, or any modified polymerase that can effectuate the synthesis of a nucleic acid molecule. Within this disclosure, a DNA polymerase may also include a polymerase, terminal transferase, reverse transcriptase, telomerase, and/or polynucleotide phosphorylase. Non-limiting examples of polymerases may include, for example, T7 DNA polymerase, eukaryotic mitochondrial DNA Polymerase γ, prokaryotic DNA polymerase I, II, III, IV, and/or V; eukaryotic polymerase α, β, γ, δ, ε, η, ζ, ι, and/or κ; $E.$ $coli$ DNA polymerase I; $E.$ $coli$ DNA polymerase III alpha and/or epsilon subunits; $E.$ $coli$ polymerase IV, $E.$ $coli$ polymerase V; $T.$ $aquaticus$ DNA polymerase I; $B.$ $stearothermophilus$ DNA polymerase I; Euryarchaeota polymerases; terminal deoxynucleotidyl transferase (TdT); $S.$ $cerevisiae$ polymerase 4; translesion synthesis polymerases; reverse transcriptase; and/or telomerase. Non-limiting examples of suitable thermostable DNA polymerases that may be used include, but are not limited to, $Thermus$ $thermophilus$ (Tth) DNA polymerase, $Thermus$ $aquaticus$ (Taq) DNA polymerase, $Thermotoga$ $neopolitana$ (Tne) DNA polymerase, $Thermotoga$ $maritima$ (Tma) DNA polymerase, $Thermococcus$ $litoralis$ (Tli or VENT™) DNA polymerase, $Pyrococcus$ $furiosus$ (Pfu) DNA polymerase, DEEPVENT™ DNA polymerase, $Pyrococcus$ $woosii$ (Pwo) DNA polymerase, $Bacillus$ $sterothermophilus$ (Bst) DNA polymerase, $Bacillus$ $caldophilus$ (Bca) DNA polymerase, Sulfobus acidocaldarius (Sac) DNA polymerase, $Thermoplasma$ $acidophilum$ (Tac) DNA polymerase, $Thermus$ $flavus$ (Tfl/Tub) DNA polymerase, $Thermus$ $ruber$ (Tru) DNA polymerase, $Thermus$ $brockianus$ (e.g., DYNAZYME™) DNA polymerase, $Methanobacterium$ $thermoautotrophicum$ (Mth) DNA polymerase, mycobacterium DNA polymerase (Mtb, Mlep), and mutants, and variants and derivatives thereof. RNA polymerases such as T3, T5 and SP6 and mutants, variants and derivatives thereof may also be used in accordance with the present teachings. Generally, any type I DNA polymerase may be used in accordance with the present teachings although other DNA polymerases may be used including, but not limited to, type III or family A, B, C etc. DNA polymerases. In addition, any genetically engineered DNA polymerases, any having reduced or insignificant 3'-to-5' exonuclease activity (e.g., SuperScript™ DNA polymerase), and/or genetically engineered DNA polymerases (e.g., those having the active site mutation F667Y or the equivalent of F667Y (e.g., in Tth), AmpliTaq®FS, ThermoSequenase™), AmpliTaq® Gold, Platinum® Taq DNA Polymerase, Terminator I, Terminator II, Therminator III, Therminator Gamma (all available from New England Biolabs, Beverly, Mass.), and/or any derivatives and fragments thereof, may be used in accordance with the present teachings. Other nucleic acid polymerases may also be suitable as would be understood by one of skill in the art.

Polymerases used in accordance with the present teachings may be any enzyme that can synthesize a nucleic acid molecule from a nucleic acid template, typically in the 5'-to-3' direction. The nucleic acid polymerases used in the methods disclosed herein may be mesophilic or thermophilic. Exemplary mesophilic DNA polymerases include T7 DNA polymerase, T5 DNA polymerase, Klenow fragment DNA polymerase, DNA polymerase III and the like. Exemplary thermostable DNA polymerases that may be used in the methods of the present teachings include Taq, Tne, Tma, Pfu, Tfl, Tth, Stoffel fragment, VENT™ and DEEPVENT™ DNA polymerases, and mutants, variants and derivatives thereof (U.S. Pat. Nos. 5,436,149; 4,889,818; 4,965,188; 5,079,352; 5,614,365; 5,374,553; 5,270,179; 5,047,342; and 5,512,462; PCT Publication Nos. WO 92/06188, WO 92/06200, and WO 96/10640; Barnes, $Gene$ 112:29-35 (1992); Lawyer, et al., $PCR$ $Meth.$ $Appl.$ 2:275-287 (1993); Flaman, et al., $Nucl.$ $Acids$ $Res.$ 22:3259-3260 (1994)). Examples of DNA polymerases substantially lacking in 3'-exonuclease activity include, but are not limited to, Taq, Tne (exo⁻), Tma (exo⁻), Pfu (exo⁻), Pwo (exo⁻) and Tth DNA polymerases, and mutants, variants and derivatives thereof. These polymerases may be used in any suitable combination with the pyrophosphorolysis enzyme or the polyphosphorolysis enzyme as described herein.

DNA polymerases for use in the methods disclosed herein may be obtained commercially, for example, from Life Technologies Corp. (Carlsbad, Calif.), Pharmacia (Piscataway, N.J.), Sigma (St. Louis, Mo.) and Boehringer Mannheim (Indianapolis, Ind.).

Enzymes for use in the compositions, reaction mixtures, methods, compositions and kits provided herein may also include any enzyme having reverse transcriptase activity.

Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, et al., *Science* 239:487-491 (1988); U.S. Pat. Nos. 4,889,818 and 4,965,188), Tne DNA polymerase (PCT Publication No. WO 96/10640), Tma DNA polymerase (U.S. Pat. No. 5,374,553) and mutants, fragments, variants or derivatives thereof (see, e.g., commonly owned, co-pending U.S. patent application Ser. Nos. 08/706,702 and 08/706,706, both filed Sep. 9, 1996, which are incorporated by reference herein in their entireties). As will be understood by one of ordinary skill in the art, modified reverse transcriptases and DNA polymerase having reverse transcriptase activity may be obtained by recombinant or genetic engineering techniques that are well-known in the art. Mutant reverse transcriptases or polymerases may, for example, be obtained by mutating the gene or genes encoding the reverse transcriptase or polymerase of interest by site-directed or random mutagenesis. Such mutations may include point mutations, deletion mutations and insertional mutations. In some embodiments, one or more point mutations (e.g., substitution of one or more amino acids with one or more different amino acids) are used to construct mutant reverse transcriptases or polymerases for use in the present teachings. Fragments of reverse transcriptases or polymerases may also be obtained by deletion mutation by recombinant techniques that are well-known in the art, or by enzymatic digestion of the reverse transcriptase(s) or polymerase(s) of interest using any of a number of well-known proteolytic enzymes.

In some embodiments, enzymes for use in the methods provided herein include those that are reduced or substantially reduced in RNase H activity. Such enzymes that are reduced or substantially reduced in RNase H activity may be obtained by mutating the RNase H domain within the reverse transcriptase of interest, for example, by one or more point mutations, one or more deletion mutations, or one or more insertion mutations as described above. An enzyme "substantially reduced in RNase H activity" refers to an enzyme that has less than about 30%, less than about 25%, less than about 20%, less than about 15%, less than about 10%, less than about 7.5%, or less than about 5%, or less than about 5% or less than about 2%, of the RNase H activity of the corresponding wild type or RNase H$^+$ enzyme such as wild type Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, et al., *Nucl. Acids Res.* 16:265 (1988), in Gerard, et al., *FOCUS* 14:91 (1992), and in U.S. Pat. No. 5,668,005, the disclosures of all of which are fully incorporated herein by reference.

Polypeptides having reverse transcriptase activity for use in the methods provided herein may be obtained commercially, for example, from Life Technologies Corp. (Carlsbad, Calif.), Pharmacia (Piscataway, N.J.), Sigma (Saint Louis, Mo.) or Boehringer Mannheim Biochemicals (Indianapolis, Ind.). Alternatively, polypeptides having reverse transcriptase activity may be isolated from their natural viral or bacterial sources according to standard procedures for isolating and purifying natural proteins that are well-known to one of ordinary skill in the art (see, e.g., Houts, et al., *J. Virol.* 29:517 (1979)). In addition, the polypeptides having reverse transcriptase activity may be prepared by recombinant DNA techniques that are familiar to one of ordinary skill in the art (see, e.g., Kotewicz, et al., *Nucl. Acids Res.* 16:265 (1988); Soltis and Skalka, *Proc. Natl. Acad. Sci. USA* 85:3372-3376 (1988)).

Exemplary polypeptides having reverse transcriptase activity for use in the methods provided herein include M-MLV reverse transcriptase, RSV reverse transcriptase, AMV reverse transcriptase, Rous Associated Virus (RAV) reverse transcriptase, Myeloblastosis Associated Virus (MAV) reverse transcriptase and Human Immunodeficiency Virus (HIV) reverse transcriptase, and others described in PCT Publication No. WO 98/47921 and derivatives, variants, fragments or mutants thereof, and combinations thereof. In a further embodiment, the reverse transcriptases are reduced or substantially reduced in RNase H activity, and may be selected from the group consisting of M-MLV H$^-$ reverse transcriptase, RSV H$^-$ reverse transcriptase, AMV H$^-$ reverse transcriptase, RAV H$^-$ reverse transcriptase, MAV H$^-$ reverse transcriptase and HIV H$^-$ reverse transcriptase, and derivatives, variants, fragments or mutants thereof, and combinations thereof. Reverse transcriptases of particular interest include AMV RT and M-MLV RT, and optionally AMV RT and M-MLV RT having reduced or substantially reduced RNase H activity (e.g., AMV RT alpha H$^-$/BH$^+$ and M-MLV RT H$^-$). Reverse transcriptases for use in the present teachings include SuperScript™, SuperScript™II, ThermoScript™ and ThermoScript™ II available from Life Technologies Corp. See generally, PCT Publication No. WO 98/47921, U.S. Pat. Nos. 5,244,797 and 5,668,005, the entire contents of each of which are herein incorporated by reference.

In another aspect, the present disclosure provides reaction mixtures for polymerizing and/or amplifying a nucleic acid sequence of interest (e.g., a target sequence). In some embodiments, the reaction mixture may further comprise a detectable label. The methods may also include one or more steps for detecting the detectable label to quantitate the amplified nucleic acid. As used herein, the term "detectable label" refers to any of a variety of signaling molecules indicative of amplification. For example, SYBR® Green and other DNA-binding dyes are detectable labels. Such detectable labels may comprise or may be, for example, nucleic acid intercalating agents or non-intercalating agents. As used herein, an intercalating agent is an agent or moiety capable of non-covalent insertion between stacked base pairs of a double-stranded nucleic acid molecule. A non-intercalating agent is one that does not insert into the double-stranded nucleic acid molecule. The nucleic acid binding agent may produce a detectable signal directly or indirectly. The signal may be detectable directly using, for example, fluorescence and/or absorbance, or indirectly using, for example, any moiety or ligand that is detectably affected by proximity to double-stranded nucleic acid is suitable such as a substituted label moiety or binding ligand attached to the nucleic acid binding agent. It is typically necessary for the nucleic acid binding agent to produce a detectable signal when bound to a double-stranded nucleic acid that is distinguishable from the signal produced when that same agent is in solution or bound to a single-stranded nucleic acid. For example, intercalating agents such as ethidium bromide fluoresce more intensely when intercalated into double-stranded DNA than when bound to single-stranded DNA, RNA, or in solution (see, e.g., U.S. Pat. Nos. 5,994,056; 6,171,785; and/or 6,814,934). Similarly, actinomycin D fluoresces in the red portion of the UV/VIS spectrum when bound to single-stranded nucleic acids, and fluoresces in the green portion of the UV/VIS spectrum when bound to double-stranded nucleic acids. And in another example, the photoreactive psoralen 4-aminomethyl-4-5',8-trimethylpsoralen (AMT) has been reported to exhibit decreased absorption at long wavelengths and fluorescence upon intercalation into double-stranded DNA (Johnson et al. *Photochem. & Photobiol.*, 33:785-791 (1981). For example, U.S. Pat. No. 4,257,774 describes the direct binding of fluorescent intercalators to DNA (e.g., ethidium salts, daunomycin, mepacrine and acridine orange, 4',6-diamidino-α-phenylindole). Non-intercalating agents (e.g., minor groove binders as described herein such as Hoechst 33258, distamycin, netropsin) may also be suitable for use. For example, Hoechst 33258 (Searle, et al. *Nucl. Acids Res.* 18(13):3753-3762 (1990)) exhibits altered fluorescence with an increasing amount of target. Minor groove binders are described in more detail elsewhere herein.

Other DNA binding dyes are available to one of skill in the art and may be used alone or in combination with other agents and/or components of an assay system. Exemplary DNA binding dyes may include, for example, acridines (e.g., acridine orange, acriflavine), actinomycin D (Jain, et al. *J. Mol. Biol.* 68:21 (1972)), anthramycin, BOBO™-1, BOBO™-3, BO-PRO™-1, cbromomycin, DAPI (Kapuseinski, et al. *Nucl. Acids Res.* 6(112): 3519 (1979)), daunomycin, distamycin (e.g., distamycin D), dyes described in U.S. Pat. No. 7,387,887, ellipticine, ethidium salts (e.g., ethidium bromide), fluorcoumanin, fluorescent intercalators as described in U.S. Pat. No. 4,257,774, GelStar® (Cambrex Bio Science Rockland Inc., Rockland, Me.), Hoechst 33258 (Searle and Embrey, *Nucl. Acids Res.* 18:3753-3762 (1990)), Hoechst 33342, homidium, JO-PRO™-1, LIZ® dyes, LO-PRO™-1, mepacrine, mithramycin, NED™ dyes, netropsin, 4',6-diamidino-α-phenylindole, proflavine, POPO™-1, POPO™-3, PO-PRO™-1, propidium iodide, ruthenium polypyridyls, S5, SYBR® Gold, SYBR® Green I (U.S. Pat. Nos. 5,436,134 and 5,658,751), SYBR® Green II, SYBR® GreenER™, SYTOX® blue, SYTOX® green, SYTO® 43, SYTO® 44, SYTO® 45, SYTOX® Blue, TO-PRO®-1, SYTO® 11, SYTO® 13, SYTO® 15, SYTO® 16, SYTO® 20, SYTO® 23, thiazole orange (Aldrich Chemical Co., Milwaukee, Wis.), TOTO™-3, YO-PRO®-1, and YOYO®-3 (Life Technologies Corp., Carlsbad, Calif.), among others. SYBR® Green I (see, e.g., U.S. Pat. Nos. 5,436,134; 5,658,751; and/or 6,569,927), for example, has been used to monitor a PCR reactions. Other DNA binding dyes may also be suitable as would be understood by one of skill in the art.

For use as described herein, one or more detectable labels and/or quenching agents may be attached to one or more primers and/or probes (e.g., detectable label). The detectable label may emit a signal when free or when bound to one of the target nucleic acids. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any of several detectable labels may be used to label the primers and probes used in the methods described herein. As mentioned above, in some embodiments the detectable label may be attached to a probe, which may be incorporated into a primer, or may otherwise bind to amplified target nucleic acid (e.g., a detectable nucleic acid binding agent such as an intercalating or non-intercalating dye). When using more than one detectable label, each should differ in their spectral properties such that the labels may be distinguished from each other, or such that together the detectable labels emit a signal that is not emitted by either detectable label alone. Exemplary detectable labels include, for instance, a fluorescent dye or fluorophore (e.g., a chemical group that can be excited by light to emit fluorescence or phosphorescence), "acceptor dyes" capable of quenching a fluorescent signal from a fluorescent donor dye, and the like. Suitable detectable labels may include, for example, fluoresceins (e.g., 5-carboxy-2,7-dichlorofluorescein; 5-Carboxyfluorescein (5-FAM™); 5-Hydroxy Tryptamine (5-HAT); 6-JOE™; 6-carboxyfluorescein (6-FAM™); FITC; 6-carboxy-1,4-dichloro-2',7'-dichlorofluorescein (TET™); 6-carboxy-1,4-dichloro-2',4',5',7'-tetrachlorofluorescein (HEX™); 6-carboxy-4',5'-dichloro-2',7'-dimethoxyfluorescein (JOE™); Alexa Fluor® fluorophores (e.g., 350, 405, 430, 488, 500, 514, 532, 546, 555, 568, 594, 610, 633, 635, 647, 660, 680, 700, 750); BODIPY® fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP, EGFP), blue fluorescent protein (e.g., BFP, EBFP, EBFP2, Azurite, mKalamal), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY® FL/BODIPY® FL, Fluorescein/QSY7 and QSY9), LysoTracker® and LysoSensor™ (e.g., LysoTracker® Blue DND-22, LysoTracker® Blue-White DPX, LysoTracker® Yellow HCK-123, LysoTracker® Green DND-26, LysoTracker® Red DND-99, LysoSensor™ Blue DND-167, LysoSensor™ Green DND-189, LysoSensor™ Green DND-153, LysoSensor™ Yellow/Blue DND-160, LysoSensor™ Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA™), 5 GLD, 6-Carboxyrhodamine 6G, Lissamine, Lissamine Rhodamine B, Phallicidine, Phalloidine, Red, Rhod-2, ROX™ (6-carboxy-X-rhodamine), 5-ROX™ (carboxy-X-rhodamine), Sulphorhodamine B can C, Sulphorhodamine G Extra, TAMRA™ (6-carboxytetramethylrhodamine), Tetramethylrhodamine (TRITC), WT), Texas Red®, Texas Red®-X, VIC® and other labels described in, e.g., U.S. Patent Application Publication No. 2009/0197254 (incorporated herein by reference in its entirety), among others as would be known to those of skill in the art. Other detectable labels may also be used (see, e.g., U.S. Patent Application Publication No. 2009/0197254 (incorporated herein by reference in its entirety)), as would be known to those of skill in the art. Any of these systems and detectable labels, as well as many others, may be used to detect amplified target nucleic acids.

Some detectable labels may be sequence-based, for example 5'-nuclease probes. Such probes may comprise one or more detectable labels. Various detectable labels are known in the art, for example (TaqMan® probes described herein (See also U.S. Pat. No. 5,538,848 (incorporated herein by reference in its entirety)) various stem-loop molecular beacons (See, e.g., U.S. Pat. Nos. 6,103,476 and 5,925,517 and Tyagi and Kramer, *Nature Biotechnology* 14:303-308 (1996)), stemless or linear beacons (See, e.g., PCT Publication No. WO 99/21881; U.S. Pat. No. 6,485, 901), PNA Molecular Beacons™ (See, e.g., U.S. Pat. Nos. 6,355,421 and 6,593,091), linear PNA beacons (See, e.g., Kubista et al., *SPIE* 4264:53-58 (2001)), non-FRET probes (See, e.g., U.S. Pat. No. 6,150,097), Sunrise®/Amplifluor® probes (U.S. Pat. No. 6,548,250), stem-loop and duplex Scorpions™ probes (Solinas et al., *Nucleic Acids Research* 29:E96 (2001) and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes (Svanvik, et al. *Anal Biochem* 281:26-35 (2001)), self-assembled nanoparticle probes, ferrocene-modified probes described, for example, in U.S. Pat. No. 6,485,901; Mhlanga et al., *Methods* 25:463-471 (2001); Whitcombe et al., *Nature Biotechnology.* 17:804-807 (1999); Isacsson et al., *Molecular Cell Probes.* 14:321-328 (2000); Svanvik et al., *Anal Biochem.* 281:26-35 (2000); Wolffs et al., *Biotechniques* 766:769-771 (2001); Tsourkas et al., *Nucleic Acids Research.* 30:4208-4215 (2002); Riccelli et al., *Nucleic Acids Research* 30:4088-4093 (2002); Zhang et al., *Acta Biochimica et Biophysica Sinica (Shanghai).* 34:329-332 (2002); Maxwell et al., *J. Am. Chem. Soc.* 124:9606-9612 (2002); Broude et al., *Trends Biotechnol.* 20:249-56 (2002); Huang et al., *Chem. Res. Toxicol.* 15:118-126 (2002); and Yu et al., *J. Am. Chem. Soc.* 14:11155-11161 (2001); QuantiProbes® (www.qiagen.com), HyBeacons® (French, et al. *Mol. Cell. Probes* 15:363-374 (2001)), displacement probes (Li, et al. *Nucl. Acids Res.* 30:e5 (2002)), HybProbes (Cardullo, et al. *Proc. Natl. Acad. Sci. USA* 85:8790-8794 (1988)), MGB Alert (www.nanogen.com), Q-PNA (Fiandaca, et al. *Genome Res.* 11:609-611 (2001)), Plexor® (www.Promega.com), LUX™ primers (Nazarenko, et al. *Nucleic Acids Res.* 30:e37 (2002)), DzyNA primers (Todd, et al. *Clin. Chem.* 46:625-630 (2000)). Detectable labels may also comprise non-detectable quencher moieties that quench the fluorescence of the detectable label, including, for example, black hole quenchers (Biosearch), Iowa Black® quenchers (IDT), QSY quenchers (Life Technologies Corp.), and Dabsyl and Dabcyl sulfonate/carboxylate Quenchers (Epoch). Detectable labels may also comprise two probes, wherein for example a fluorophore is on one probe, and a quencher is on the other, wherein hybridization of the two probes together on a target quenches the signal, or wherein hybridization on a target alters the signal signature via a change in fluorescence. Exemplary systems may also include FRET, salicylate/DTPA ligand systems (see, e.g., Oser et al. *Angew. Chem. Int. Engl.* 29(10):1167 (1990)), displacement hybridization, homologous probes, and/or assays described in European Patent No. EP 070685 and/or U.S. Pat. No. 6,238,927. Detectable labels can also comprise sulfonate derivatives of fluorescein dyes with $SO_3$ instead of the carboxylate group, phosphoramidite forms of fluorescein, phosphoramidite forms of Cy5 (available for example from GE Healthcare). All references cited above are hereby incorporated herein by reference in their entirety.

The compositions and methods described herein may be useful for detecting and/or quantifying a variety of target nucleic acids from a test sample. A target nucleic acid is any nucleic acid for which an assay system is designed to identify or detect as present (or not), and/or quantify in a test sample. Such nucleic acids may include, for example, those of infectious agents (e.g., virus, bacteria, parasite, and the like), a disease process such as cancer, diabetes, or the like, or to measure an immune response. Exemplary "test samples" include various types of samples, such as biological samples. Exemplary biological samples include, for instance, a bodily fluid (e.g., blood, saliva, spinal fluid), a tissue sample, a food (e.g., meat) or beverage (e.g., milk) product, or the like. Expressed nucleic acids may include, for example, genes for which expression (or lack thereof) is associated with medical conditions such as infectious disease (e.g., bacterial, viral, fungal, protozoal infections) or cancer. The methods described herein may also be used to detect contaminants (e.g., bacteria, virus, fungus, and/or protozoan) in pharmaceutical, food, or beverage products. The methods described herein may be also be used to detect rare alleles in the presence of wild type alleles (e.g., one mutant allele in the presence of $10^6$-$10^9$ wild type alleles). The methods are useful to, for example, detect minimal residual disease (e.g., rare remaining cancer cells during remission, especially mutations in the p53 gene or other tumor suppressor genes previously identified within the tumors), and/or measure mutation load (e.g., the frequency of specific somatic mutations present in normal tissues, such as blood or urine).

The detection of the signal may be using any reagents or instruments that detect a change in fluorescence from a fluorophore. For example, detection may be performed using any spectrophotometric thermal cycler. Examples of spectrophotometric thermal cyclers include, but are not limited to, Applied Biosystems (AB) PRISM® 7000, AB 7300 real-time PCR system, AB 7500 real-time PCR system, AB PRISM® 7900HT, Bio-Rad ICycler IQ™, Cepheid Smart-Cycler® II, Corbett Research Rotor-Gene 3000, Idaho Technologies R.A.P.I.D.™, MJ Research Chromo 4™, Roche Applied Science LightCycler®, Roche Applied Science LightCycler®2.0, Stratagene Mx3000P™, and Stratagene Mx4000™. It should be noted that new instruments are being developed at a rapid rate and any like instruments may be used for the methods.

According to another embodiment of the present teachings, the methods disclosed herein may be used in diagnostic and/or prognostic methods for identifying diseases and/or in determining patient response to treatment with certain drugs, medications or methods of therapy. An exemplary condition that can be associated with polymorphisms is cancer. Thus, the present teachings provide a method of diagnosing susceptibility to a cancer, prognosis of outcome for treatment of cancer, or the stage and/or identity of the cancer based on the genotype identified in the sample.

The prognostic methods of the present teachings are useful for determining if a patient is at risk for recurrence. Cancer recurrence is a concern relating to a variety of types of cancer. For example, of patients undergoing complete surgical removal of colon cancer, 25-40% of patients with stage II colon carcinoma and about 50% of patients with stage III colon carcinoma experience cancer recurrence. One explanation for cancer recurrence is that patients with relatively early stage disease, for example, stage II or stage III, already have small amounts of cancer spread outside of the affected organ that were not removed by surgery. These cancer cells, referred to as micrometastases, cannot typically be detected with currently available tests.

The prognostic methods disclosed herein can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The prognostic methods according to certain embodiments also are useful for determining a proper course of treatment for a patient having cancer. A course of treatment refers to the therapeutic measures taken for a patient after diagnosis or after treatment for cancer. For example, a determination of the likelihood for cancer recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

Exemplary cancers that may be evaluated using a method as disclosed herein include, but are not limited to hematopoietic neoplasms, Adult T-cell leukemia/lymphoma, Lymphoid Neoplasms, Anaplastic large cell lymphoma, Myeloid Neoplasms, Histiocytoses, Hodgkin Diseases (HD), Precursor B lymphoblastic leukemia/lymphoma (ALL), Acute myelogenous leukemia (AML), Precursor T lymphoblastic leukemia/lymphoma (ALL), Myelodysplastic syndromes, Chronic Myeloproliferative disorders, Chronic lymphocytic leukemia/small lymphocytic lymphoma (SLL), Chronic Myelogenous Leukemia (CML), Lymphoplasmacytic lymphoma, Polycythemia Vera, Mantle cell lymphoma, Essential Thrombocytosis, Follicular lymphoma, Myelofibrosis with Myeloid Metaplasia, Marginal zone lymphoma, Hairy cell leukemia, Hemangioma, Plasmacytoma/plasma cell myeloma, Lymphangioma, Glomangioma, Diffuse large B-cell lymphoma, Kaposi Sarcoma, Hemanioendothelioma, Burkitt lymphoma, Angiosarcoma, T-cell chronic lymphocytic leukemia, Hemangiopericytoma, Large granular lymphocytic leukemia, head & neck cancers, Basal Cell Carcinoma, Mycosis fungoids and sezary syndrome, Squamous Cell Carcinoma, Ceruminoma, Peripheral T-cell lymphoma, Osteoma, Nonchromaffin Paraganglioma, Angioimmunoblastic T-cell lymphoma, Acoustic Neurinoma, Adenoid Cystic Carcinoma, Angiocentric lymphoma, Mucoepidermoid Carcinoma, NK/T-cell lymphoma, Malignant Mixed Tumors, Intestinal T-cell lymphoma, Adenocarcinoma, Malignant Mesothelioma, Fibrosarcoma, Sarcomotoid Type lung cancer, Osteosarcoma, Epithelial Type lung cancer, Chondrosarcoma, Melanoma, cancer of the gastrointestinal tract, olfactory Neuroblastoma, Squamous Cell Carcinoma, Isolated Plasmocytoma, Adenocarcinoma, Inverted Papillomas, Carcinoid, Undifferentiated Carcinoma, Malignant Melanoma, Mucoepidermoid Carcinoma, Adenocarcinoma, Acinic Cell Carcinoma, Gastric Carcinoma, Malignant Mixed Tumor, Gastric Lymphoma, Gastric Stromal Cell Tumors, Amenoblastoma, Lymphoma, Odontoma, Intestinal Stromal Cell tumors, thymus cancers, Malignant Thymoma, Carcinids, Type I (Invasive thymoma), Malignant Mesethelioma, Type II (Thymic carcinoma), Non-mucin producing adenocarcinoma, Squamous cell carcinoma, Lymph epithelioma, cancers of the liver and biliary tract, Squamous Cell Carcinoma, Hepatocellular Carcinoma, Adenocarcinoma, Cholangiocarcinoma, Hepatoblastoma, papillary cancer, Angiosarcoma, solid Bronchioalveolar cancer, Fibrolameller Carcinoma, Small Cell Carcinoma, Carcinoma of the Gallbladder, Intermediate Cell carcinaoma, Large Cell Carcinoma, Squamous Cell Carcinoma, Undifferentiated cancer, cancer of the pancreas, cancer of the female genital tract, Squamous Cell Carcinoma, Cystadenocarcinoma, Basal Cell Carcinoma, Insulinoma, Melanoma, Gastrinoma, Fibrosarcoma, Glucagonamoa, Intraepithelial Carcinoma, Adenocarcinoma Embryonal, cancer of the kidney, Rhabdomysarcoma, Renal Cell Carcinoma, Large Cell Carcinoma, Nephroblastoma (Wilm's tumor), Neuroendocrine or Oat Cell carcinoma, cancer of the lower urinary tract, Adenosquamous Carcinoma, Urothelial Tumors, Undifferentiated Carcinoma, Squamous Cell Carcinoma, Carcinoma of the female genital tract, Mixed Carcinoma, Adenoacanthoma, Sarcoma, Small Cell Carcinoma, Carcinosarcoma, Leiomyosarcoma, Endometrial Stromal Sarcoma, cancer of the male genital tract, Serous Cystadenocarcinoma, Mucinous Cystadenocarcinoma, Sarcinoma, Endometrioid Tumors, Speretocytic Sarcinoma, Embryonal Carcinoma, Celioblastoma, Choriocarcinoma, Teratoma, Clear Cell Carcinoma, Leydig Cell Tumor, Unclassified Carcinoma, Sertoli Cell Tumor, Granulosa-Theca Cell Tumor, Sertoli-Leydig Cell Tumor, Disgerminoma, Undifferentiated Prostatic Carcinoma, Teratoma, Ductal Transitional carcinoma, breast cancer, Phyllodes Tumor, cancer of the bones joints and soft tissue, Paget's Disease, Multiple Myeloma, In situ Carcinoma, Malignant Lymphoma, Invasive Carcinoma, Chondrosarcoma, Mesenchymal Chondrosarcoma, cancer of the endocrine system, Osteosarcoma, Adenoma, Ewing Tumor, endocrine Carcinoma, Malignant Giant Cell Tumor, Meninginoma, Adamantinoma, Craniopharlingioma, Malignant Fibrous Histiocytoma, Papillary Carcinoma, Histiocytoma, Follicular Carcinoma, Desmoplastic Fibroma, Medullary Carcinoma, Fibrosarcoma, Anoplastic Carcinoma, Chordoma, Adenoma, Hemangioendothelioma, Memangispericytoma, Pheochromocytoma, Liposarcoma, Neuroblastoma, Paraganglioma, Histiocytoma, Pineal cancer, Rhabdomysarcoma, Pineoblastoma, Leiomyosarcoma, Pineocytoma, Angiosarcoma, skin cancer, cancer of the nervous system, ovarian cancer, prostate cancer, liver cancer, stomach cancer, Melanoma, Schwannoma, Squamous cell carcinoma, Neurofibroma, Basal cell carcinoma, Malignant Peripheral Nerve Sheath Tumor, Merkel cell carcinoma, Sheath Tumor, Extramamary Paget's Disease, Astrocytoma, Paget's Disease of the nipple, Fibrillary Astrocytoma, Glioblastoma Multiforme, Brain Stem Glioma, Cutaneous T-cell lymphoma, Pilocytic Astrocytoma, Xanthorstrocytoma, Histiocytosis, Oligodendroglioma, Ependymoma, Gangliocytoma, Cerebral Neuroblastoma, Central Neurocytoma, Dysembryoplastic Neuroepithelial Tumor, Medulloblastoma, Malignant Meningioma, Primary Brain Lymphoma, Primary Brain Germ Cell Tumor, cancers of the eye, Squamous Cell Carcinoma, Mucoepidermoid Carcinoma, Melanoma, Retinoblastoma, Glioma, Meningioma, cancer of the heart, Myxoma, Fibroma, Lipoma, Papillary Fibroelastoma, Rhasdoyoma, or Angiosarcoma among others.

Kits:

Kits for performing the methods described herein are also provided. As used herein, the term "kit" refers to a packaged set of related components, typically one or more compounds or compositions. The kit may comprise a pair of oligonucleotides for polymerizing and/or amplifying at least one target nucleic acid from a sample, one or more detergents, a nucleic acid polymerase, and/or corresponding one or more probes labeled with a detectable label. The kit may also include samples containing pre-defined target nucleic acids to be used in control reactions. The kit may also optionally include stock solutions, buffers, enzymes, detectable labels or reagents required for detection, tubes, membranes, and the like that may be used to complete the amplification reaction. In some embodiments, multiple primer sets are included. In one embodiment, the kit may include one or more of, for example, a buffer (e.g., Tris), one or more salts (e.g., KCl), glycerol, dNTPs (dA, dT, dG, dC, dU), recombinant BSA (bovine serum albumin), a dye (e.g., ROX™ passive reference dye), one or more detergents, polyethylene glycol (PEG), polyvinyl pyrrolidone (PVP), and/or gelatin (e.g., fish or bovine source). Other embodiments of particular systems and kits are also contemplated which would be understood by one of skill in the art.

In certain embodiments, kits are provided that may be used to carry out hybridization, extension and amplification reactions using the oligonucleotides provided herein. Preferred kits may comprise one or more containers, such as vials, tubes and the like, configured to contain the reagents used in the methods described herein and optionally may contain instructions or protocols for using such reagents. The kits described herein may comprise one or more components selected from the group consisting of one or more oligonucleotides described herein, including but not limited to, one or more allele-specific primer, one or more universal FRET-based reporter primer, and one or more locus specific primer; one or more nucleic acid polymerase, such as a thermostable polymerase; one or more reverse transcriptases, or any other DNA or RNA polymerase.

In some embodiments, the kit includes a first allele-specific primer, which is specific for a first allele, including a first 5'-universal tail which comprises a binding site for a first universal FRET-based reporter primer (UFP), where the first UFP includes a first fluorophore and at least a first quencher moiety; and a second allele-specific primer which is specific for a second allele, including a second 5'-universal tail which includes a binding site for a second UFP, where the second UFP includes a second fluorophore and at least a second quencher moiety; and where the first and second fluorophore may be the same or different. In some embodiments, the first fluorophore of the first UFP and the second fluorophore of the second UFP are located at the 5'-end of the first UFP and the second UFP respectively, and the at least first quencher moiety and the at least second quencher moiety are located at an internal nucleotide of the first UFP and the second UFP respectively. In some embodiments, the kits may further include a locus-specific primer. In certain embodiments, the kits may include one or more pyrophosphorolysis enzymes. In certain embodiments, the kits may include one or more polyphosphorolysis enzymes. In various embodiments, the kit includes one or more polyphosphorolyzing agents. In various embodiments, the 3'-end of at least one of the first or second allele-specific primers or locus-specific primer includes a blocking agent where the blocked end is configured to be activated by pyrophosphorolysis or polyphosphorolysis. In various embodiments, the 3'-end of at least one of the first or second UFPs includes a blocking agent such that the blocked end is configured to be activated by pyrophosphorolysis or polyphosphorolysis. In certain embodiments, the blocking agent is a dideoxynucleotide (ddN). In some embodiments, the first and second UFPs are in a linear conformation. In other embodiments, the first and second UFPs are in a stem-loop conformation. In yet other embodiments, the first UFP is in a stem-loop conformation and the second UFP is in a linear conformation. In certain embodiments, the kits described herein further include a universal FRET-based detector probe. In certain embodiments, the kits described herein further include one or more buffers or buffering salts; one or more nucleotides; one or more dideoxynucleotides (ddN); one or more target/template molecules (which may also be used for determining reaction performance, i.e., control reactions); and other reagents for analysis or further manipulation of the products or intermediates produced by the methods described herein. Such additional components may include components used for cloning and/or sequencing and components or equipment needed for the detection or quantification of the nucleic acid molecule of interest.

In certain embodiments, a kit is provided for analyzing, quantitating or detecting one or more alleles or polymorphisms in a target nucleic acid, where the kit includes a first allele-specific primer, which is specific for a first allele, including a first 5'-universal tail which includes a binding site for a first universal FRET-based detector probe, where the first universal FRET-based detector probe includes a first fluorophore and at least a first quencher moiety; and a second allele-specific primer which is specific for a second allele, including a second 5'-universal tail which includes a binding site for a second universal FRET-based detector probe, wherein the second universal FRET-based detector probe includes a second fluorophore and at least a second quencher moiety; wherein the first and second fluorophore are different and the at least first quencher moiety and the at least second quencher moiety are the same or different. In some embodiment, the first fluorophore and the second fluorophore are located at the 5'-end of the first universal FRET-based detector probe and the second universal FRET-based detector probe respectively. In some embodiments, the at least first quencher moiety of the first universal FRET-based detector probe is attached to a nucleotide at the 3' terminus or within 10 nucleotides of the 3' terminus and the at least second quencher moiety of the second universal FRET-based detector probe is attached to a nucleotide at the 3' terminus or within 10 nucleotides of the 3' terminus. In other embodiments, the kits may include a locus specific primer, where the LSP may include any combination of characteristics as described here. The kits may include one or more nucleic acid polymerases. In other embodiments, the kits may include a pyrophosphorolysis enzyme. In yet other embodiments, the kits may include a pyrophosphorolysis enzyme. In some embodiments, the first allele-specific primer and/or the second allele-specific primer and/or the locus-specific primer includes a 3' end including a blocking agent where the blocked end is configured to be activated by pyrophosphorolysis or polyphosphorolysis. In some embodiments, the 3' end of first UFP and/or second UFP includes a blocking agent such that the blocked end is configured to be activated by pyrophosphorolysis or polyphosphorolysis. In various embodiments, the blocking agent is a dideoxynucleotide (ddN). In certain embodiments, the first and second universal FRET-based detector probes are in a linear conformation. In other embodiments, the first and second universal FRET-based detector probes are in a stem-loop conformation. In yet other embodiments, the first universal FRET-based detector probe is in a stem-loop conformation and the second universal FRET-based detector probe is in a linear conformation In some embodiments, the kit includes a first allele-specific primer, which is specific for a first allele, including a first 5'-universal tail which comprises a binding site for a first universal FRET-based reporter primer (UFP), where the first UFP includes a first fluorophore; and a second allele-specific primer which is specific for a second allele, including a second 5'-universal tail which includes a binding site for a second UFP, where the second UFP includes a second fluorophore; and where the first and second fluorophore may be the same or different. In some embodiments, the first fluorophore of the first UFP and the second fluorophore of the second UFP are located at the 5'-end of the first UFP and the second UFP respectively. In various embodiments, the kit includes a locus specific primer. In certain embodiments, the kits include a double stranded intercalator dye. In some embodiments, the first and second UFPs are in a linear conformation. In other embodiments, the first and second UFPs are in a stem-loop conformation. In yet other embodiments, the first UFP is in a stem-loop conformation and the second UFP is in a linear conformation.

In certain embodiments, any of the kits described herein further comprise one or more buffers or buffering salts; one or more nucleotides; one or more dideoxynucleotides (ddN); one or more target/template molecules (which may also be used for determining reaction performance, i.e., control reactions); and other reagents for analysis or further manipulation of the products or intermediates produced by the methods described herein. Such additional components may include components used for cloning and/or sequencing and components or equipment needed for the detection or quantification of the nucleic acid molecule of interest.

In certain embodiments, kits are further provided for use in the synthesis of a nucleic acid molecule, said kit comprising one or more oligonucleotides disclosed herein, including one or more universal FRET-based reporter primers and/or one or more allele-specific primers. In certain embodiments, kits are provided for use in amplification of a nucleic acid molecule, said kit comprising one or more oligonucleotides disclosed herein, including one or more universal FRET-based reporter primers and/or one or more allele-specific primers. In certain embodiments, kits are provided for the detection or measurement of nucleic acid synthesis or amplification products comprising said kit comprising one or more oligonucleotides disclosed herein, including one or more universal FRET-based reporter primers and/or one or more allele-specific primers.

While the present teachings have been described in terms of these exemplary embodiments, the skilled artisan will readily understand that numerous variations and modifications of these exemplary embodiments are possible without undue experimentation. All such variations and modifications are within the scope of the current teachings. Aspects of the present teachings may be further understood in light of the following examples, which should not be construed as limiting the scope of the teachings in any way.

EXAMPLES

Example 1

Figure 3A:
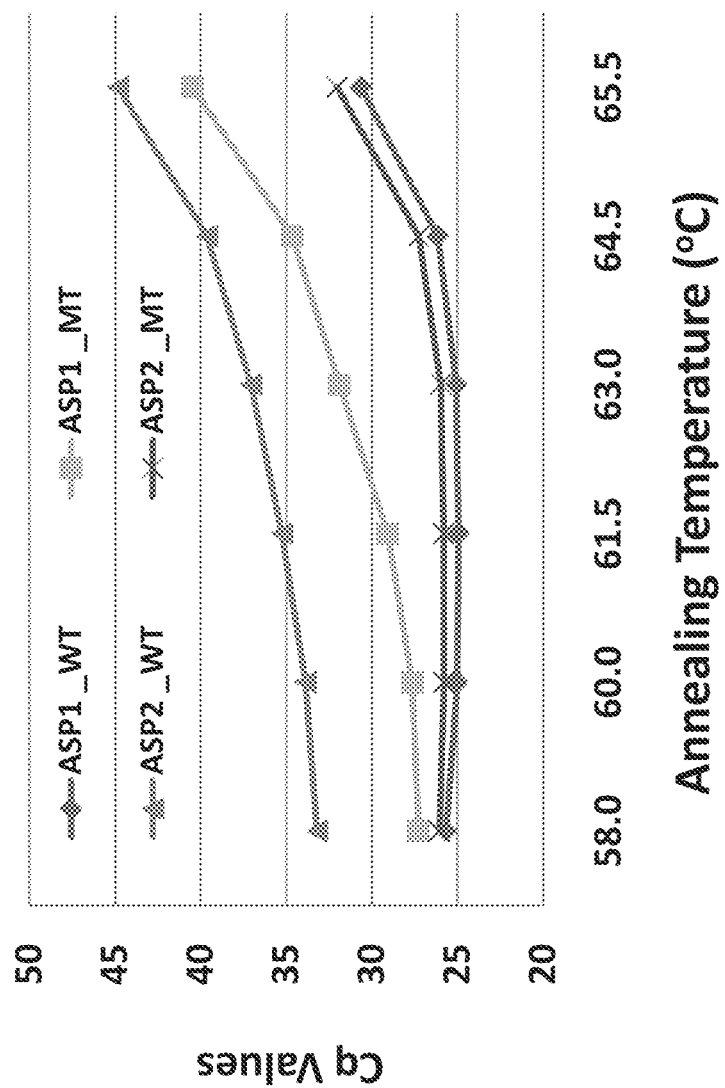
FIGS. 3A through B: Primer-based allele discrimination. Primer-based allele discrimination was demonstrated in an allele-specific BRAF assay, wherein ASP 1 was designed for the wild-type (WT) allele and ASP2 was designed for the mutant (MT) allele. Plasmid templates were used for on-target and off-target sequences.
Figure 3B:
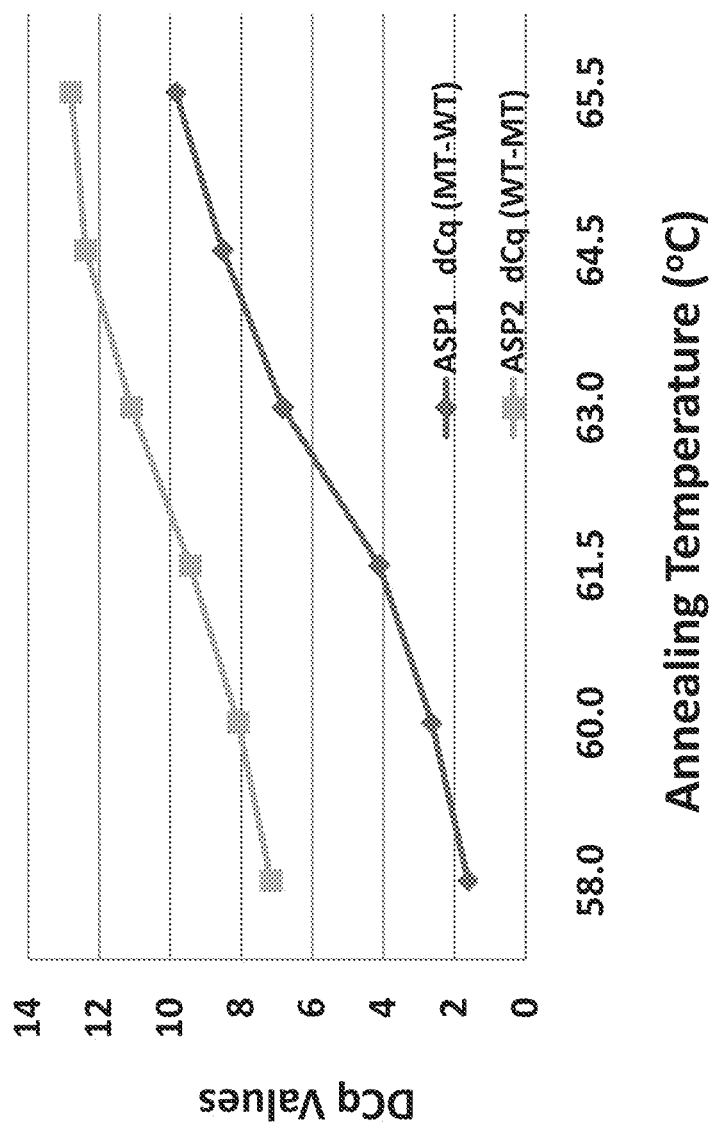

Primer-Based Allele Discrimination (see FIG. 3)

Primer-based allele discrimination was evaluated by measuring the $C_t$ values of on-target and off-target for allele 1 and allele 2. Allele1-specific primer (ASP1) and allele2-specific primer (ASP2) were designed with a SNP placed at 3'-end of the ASPs. Locus-specific primer (LSP) was used as a reserve primer that works with both ASP1 and ASP2. Allele-specific plasmids were used as for templates in PCR reaction and a TaqMan® probe was used for signal detection. Primer concentration for ASP1 and ASP2 was 300 nM and LSP was 900 nM in each reaction. Standard TaqMan® PCR conditions were used for 45 cycles and different annealing temperatures were tested ranging from 58° C.-65.5° C.

Example 2

Analysis of the UFP (see FIGS. 4A-B and 5A-B)

Figure 4A:
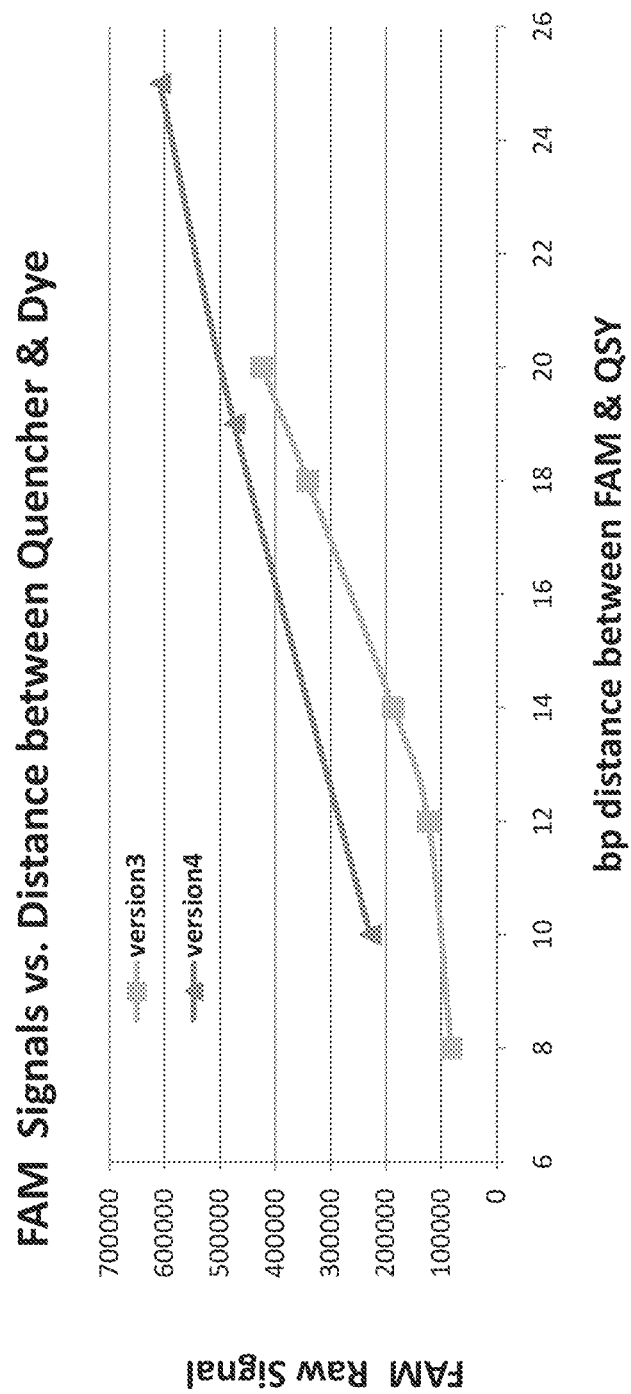
FIGS. 4A through B: Universal FRET-based Reporter Primers (UFPs): analysis of the distance between the fluorophore (FAM) and quencher (QSY7).
Figure 4B:
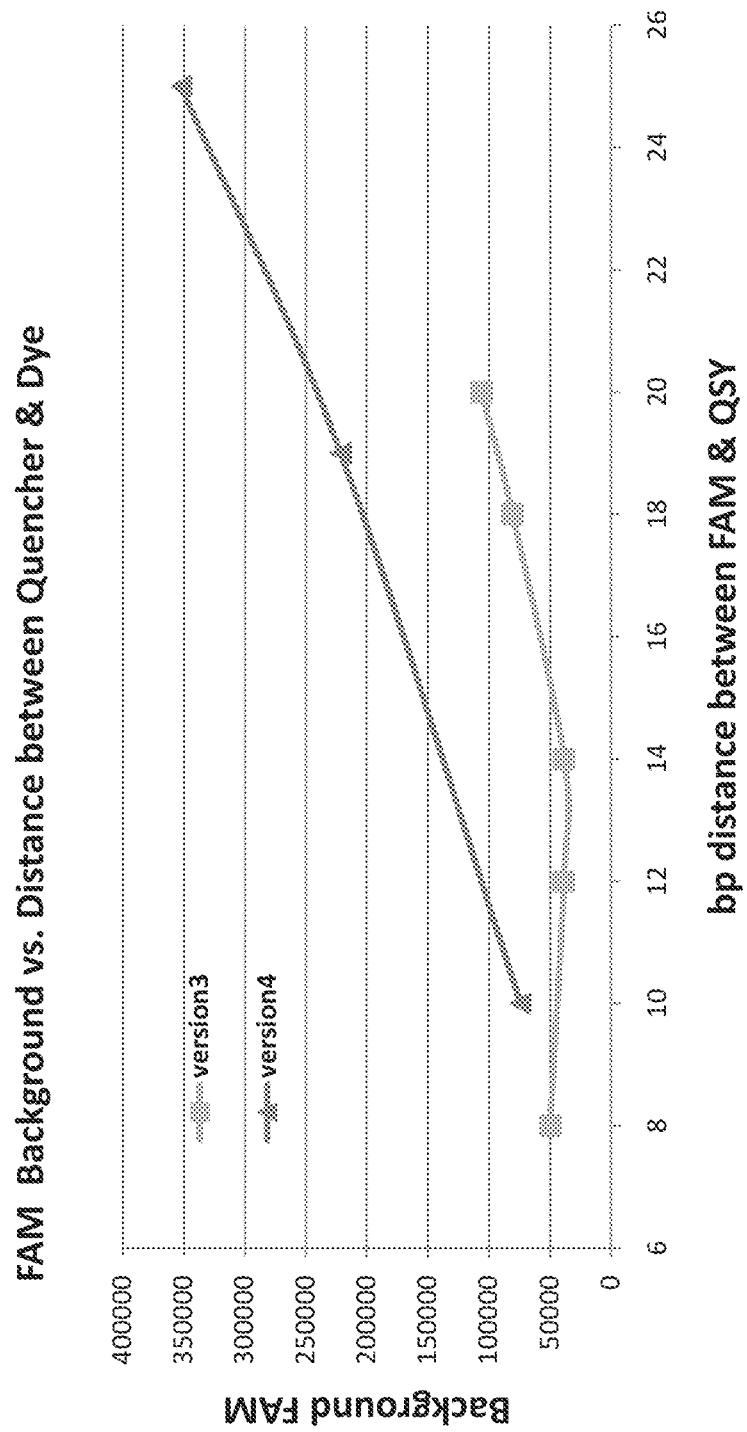

The UFPs used in this example contain a fluorophore (either FAM™ or VIC®) at its 5'-end and an internal quencher moiety (QSY®7) linked to selected nucleotides (either dT or dC) through an amino linker. The allele-specific primer tail sequence, which was identical to that of the universal FRET-based reporter primer (UFP), was added to the 5'-end of the allele-specific primer. Different versions of UFPs were designed and the distance between the fluorophore at the 5'-end of the UFP and its internal quencher were studied for their effects on both signal and background. Version 3 and Version 4 differ in length of the sequence that makes up the UFP and sequence of the tail of the allele specific primer. Version 4 is a longer sequence than Version 3 and provides higher Tm for the hybridized UFP/allele-specific primer tail pair. As can be seen in FIG. 4A, as the distance between the fluorophore and the quencher increased, the signal intensity also increased; however the background noise also increased, as shown in FIG. 4B.

Figure 5A:
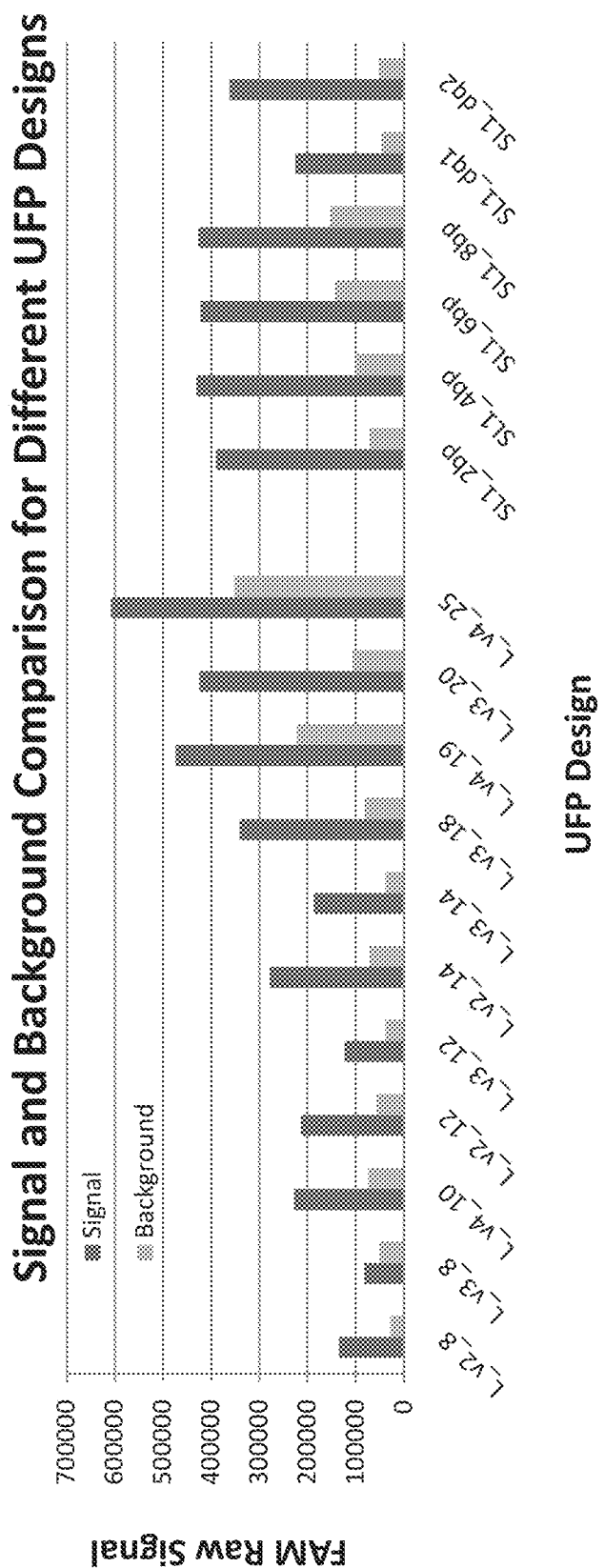
FIGS. 5A through B: Universal FRET-based Reporter Primers (UFPs): analysis of linear (L) and stem-loop (SL) UFPs.
Figure 5B:
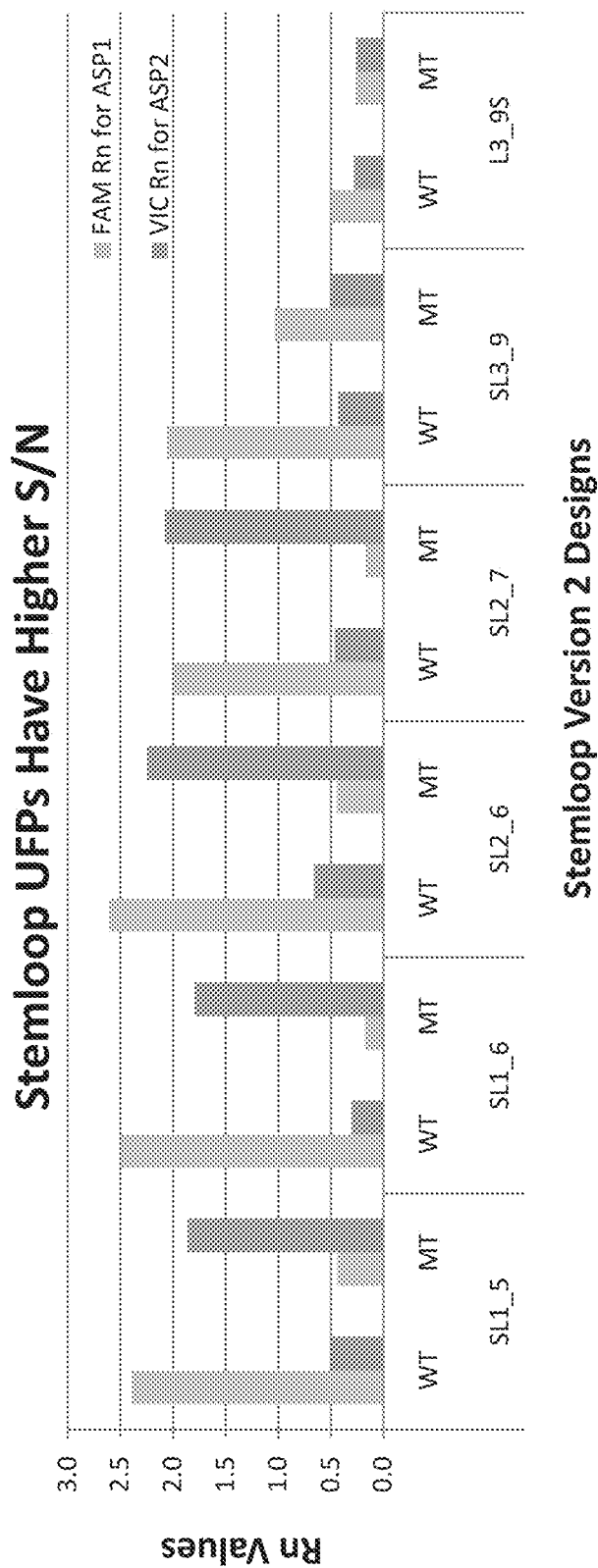

Different versions of linear (L) and stem-loop (SL) UFPs were designed and compared for both their signals and background (see, FIG. 5A). Three different stem-loop versions are shown here, SL1, SL2 and SL3. The distance between fluorophore at the 5'-end of the UFP and its internal quencher was studied. To maximize the signal to noise ratio (S/N), the length of the stem in the stem-loop structure of UFP was studied (see, FIG. 5B). For example, SL1_5 was a version 1 stem-loop design with 5 bp of stem length. Additionally, SL1-dq1 and SL1-dq2 represent a version 1 stem-loop design having a double quencher labeling, using different attachment points for the two quencher moieties. The UFP for ASP1 was labeled with FAM™ and the UFP for ASP2 was labeled with VIC®. On-target and off-target signals for allele 1 (FAM™) and allele 2(VIC®) were compared. Two pairs of them (SL1_6 and SL2_7) were selected as candidates, because they gave even lower background, thus higher S/N and more balanced FAM™ and VIC® signals in the duplex setting, in which both ASP1 and ASP2 as well as both on-target (WT) and off-target (MT) templates are run in same well.

Example 3

Assay Design (see FIGS. 6A-6H)

Figure 6A:
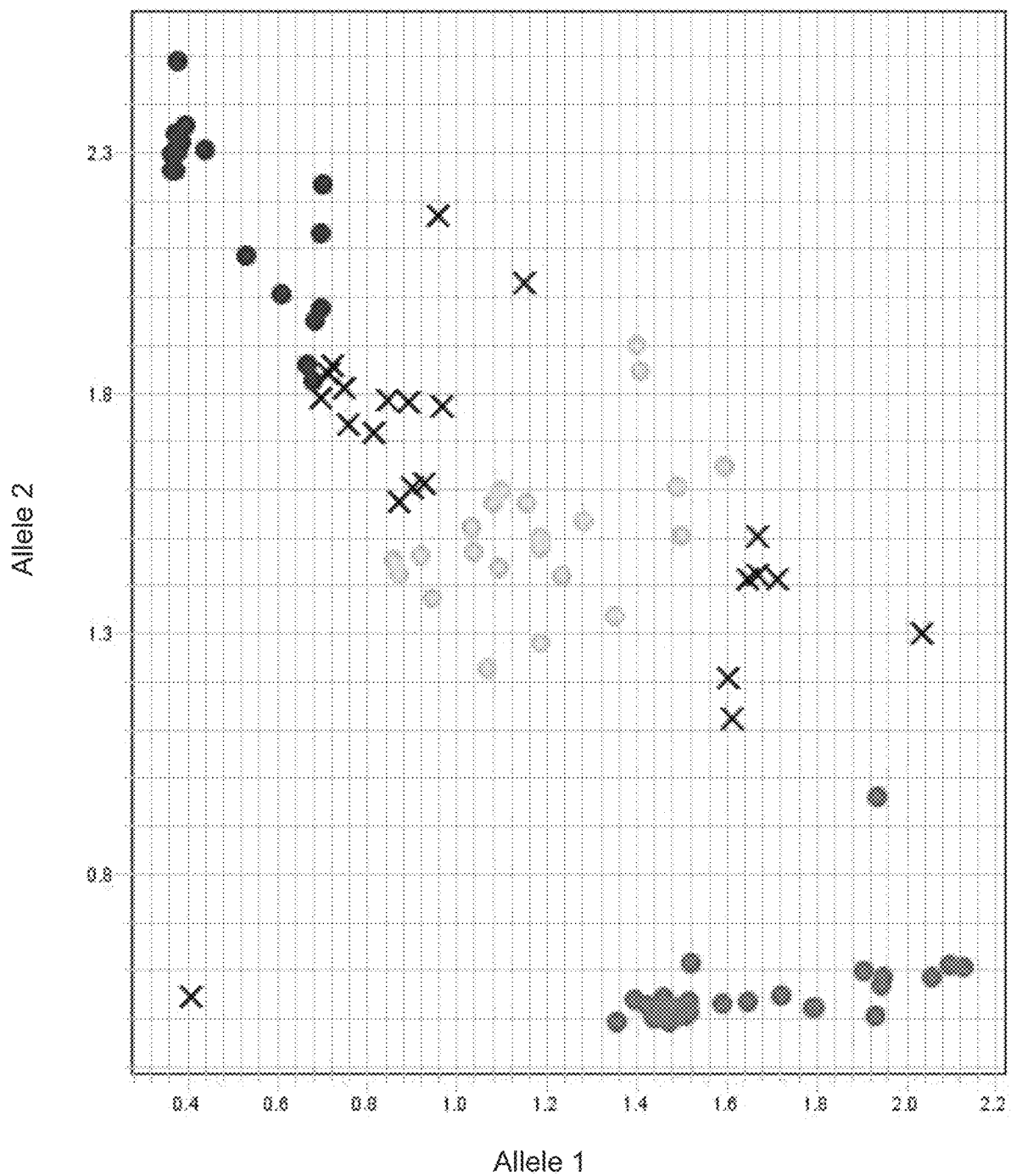
FIGS. 6A through 6H: Cluster plot analysis of two UFP designs using a panel of 92 gDNAs according to methods of certain embodiments of the present teachings.
Figure 6B:
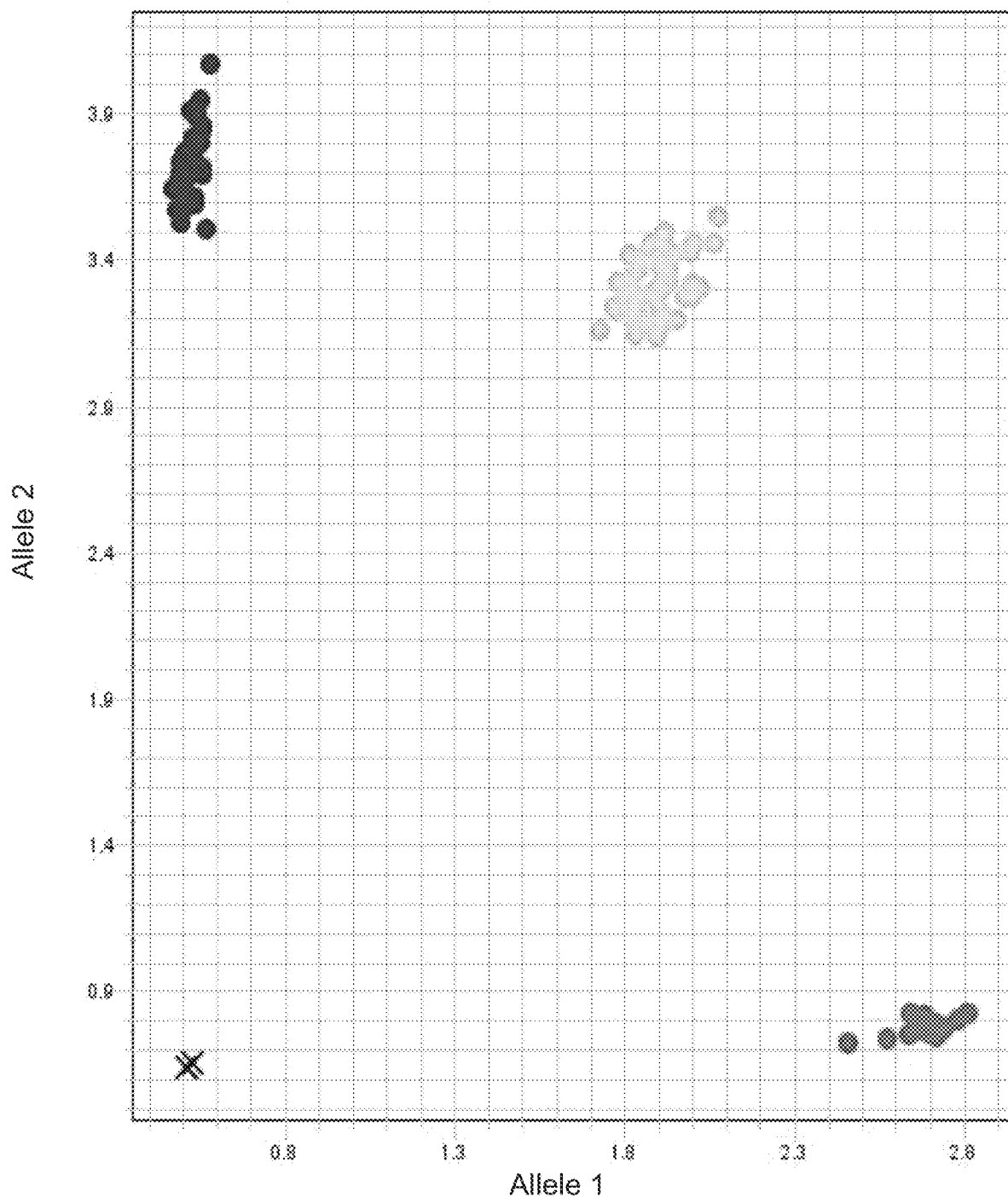
Figure 6C:
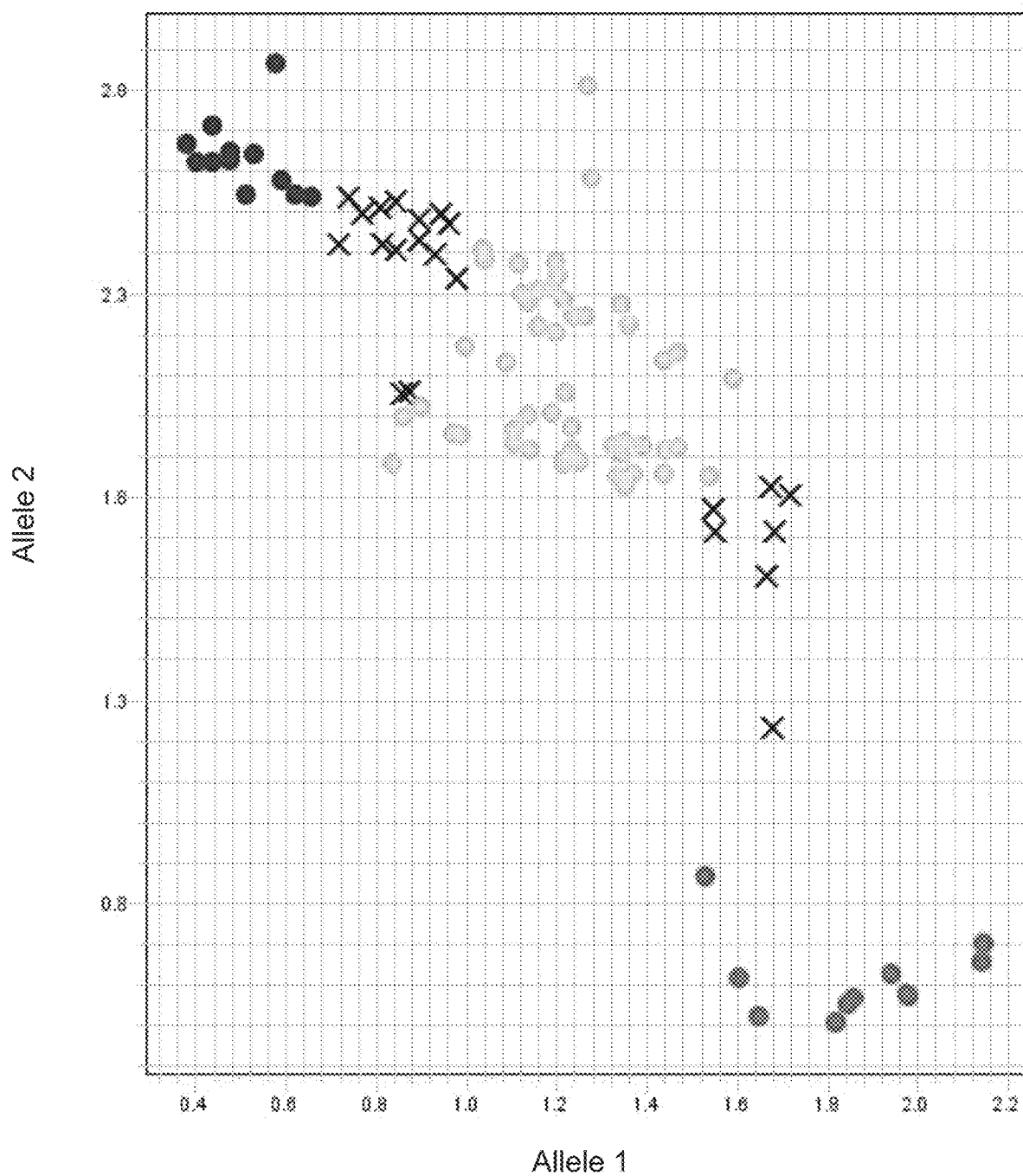
Figure 6D:
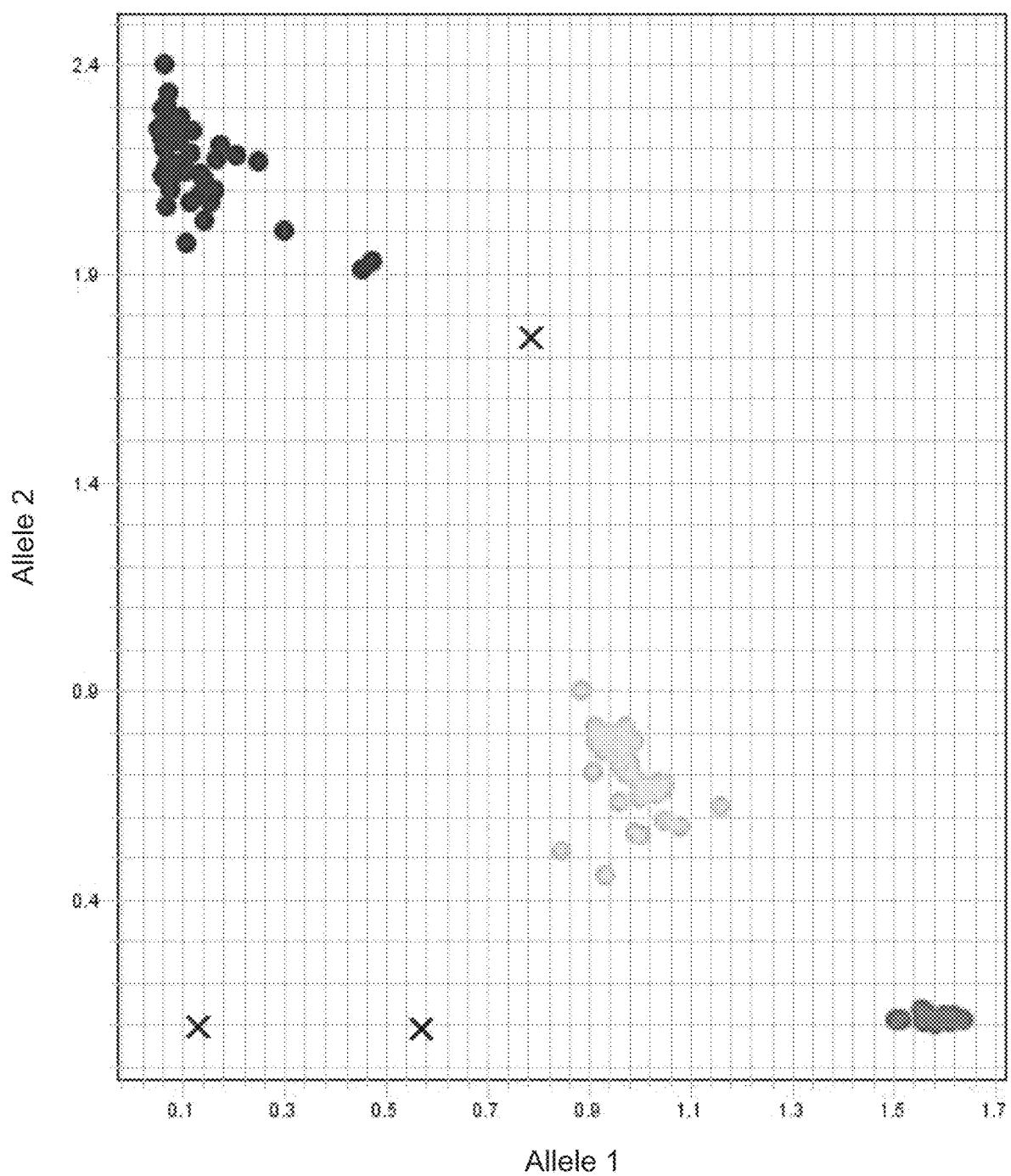
Figure 6E:
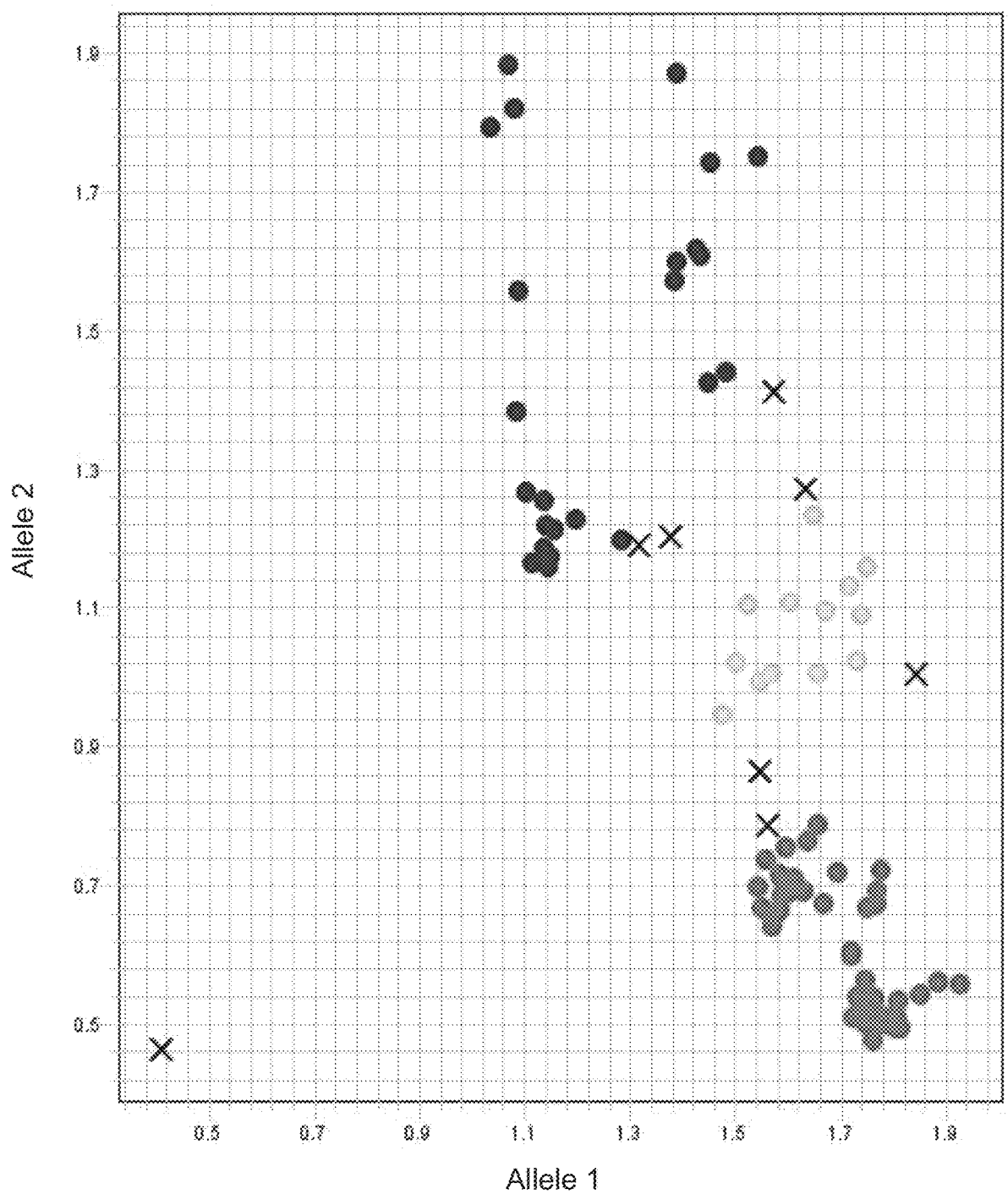
Figure 6F:
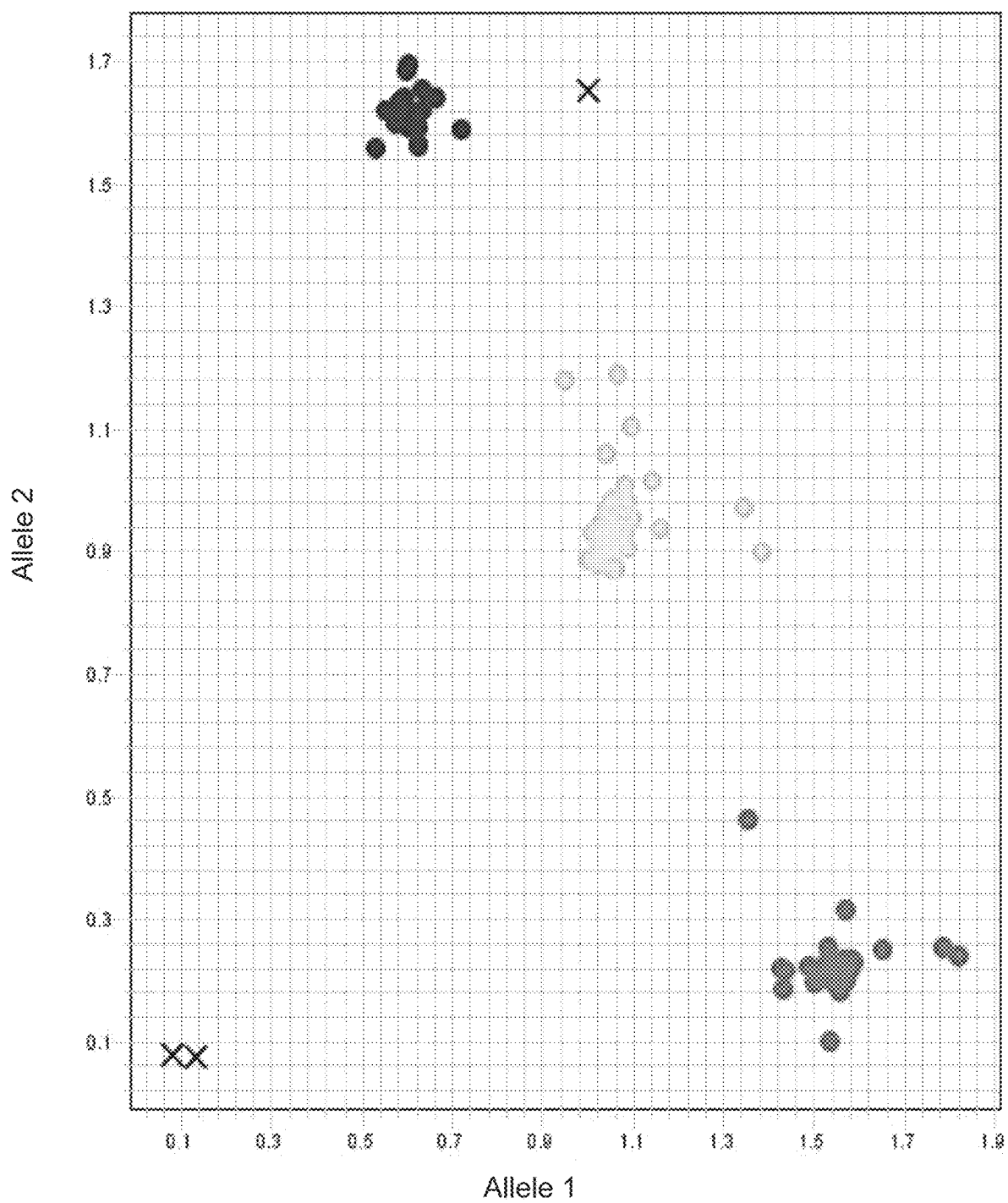
Figure 6G:
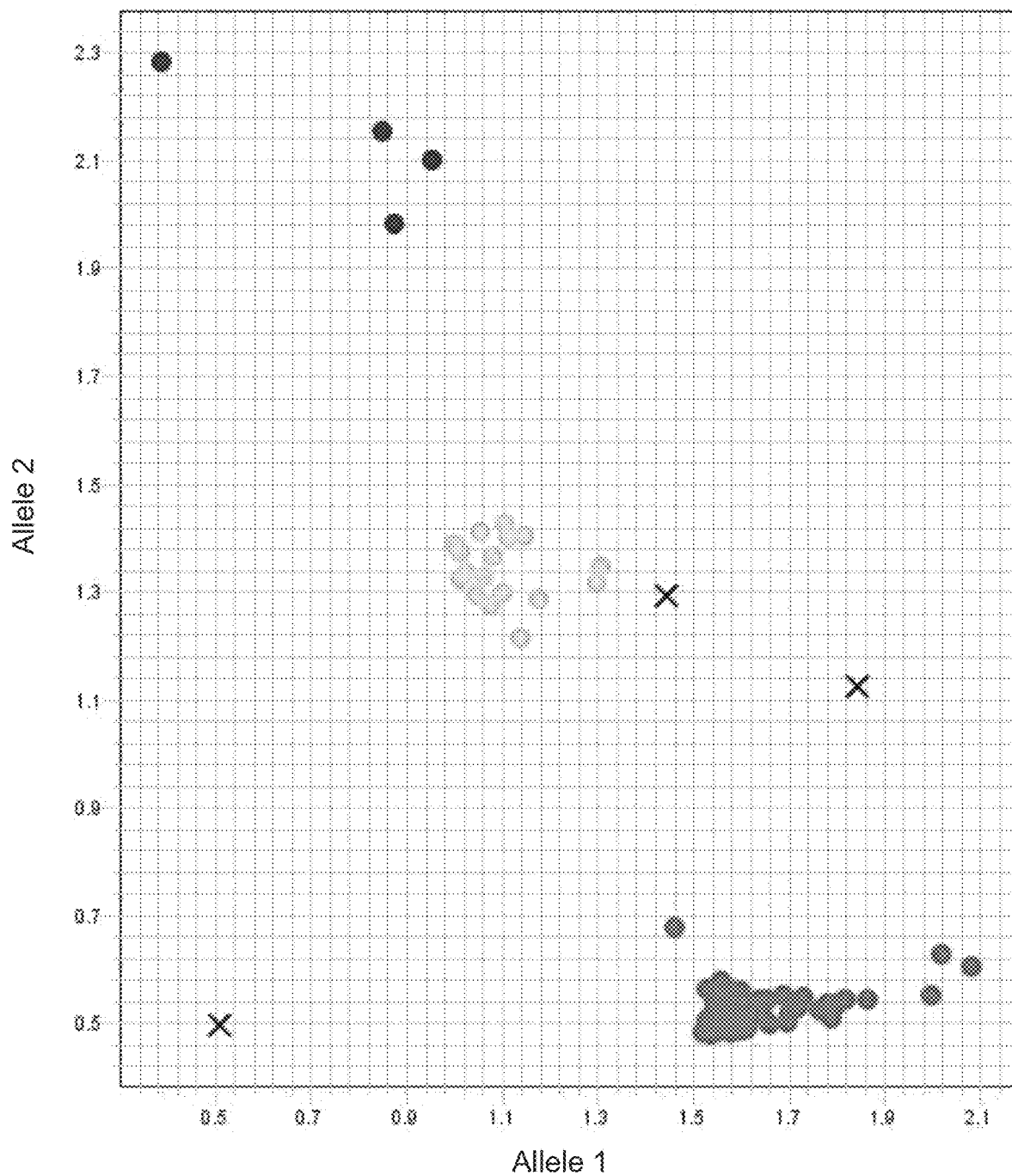
Figure 6H:
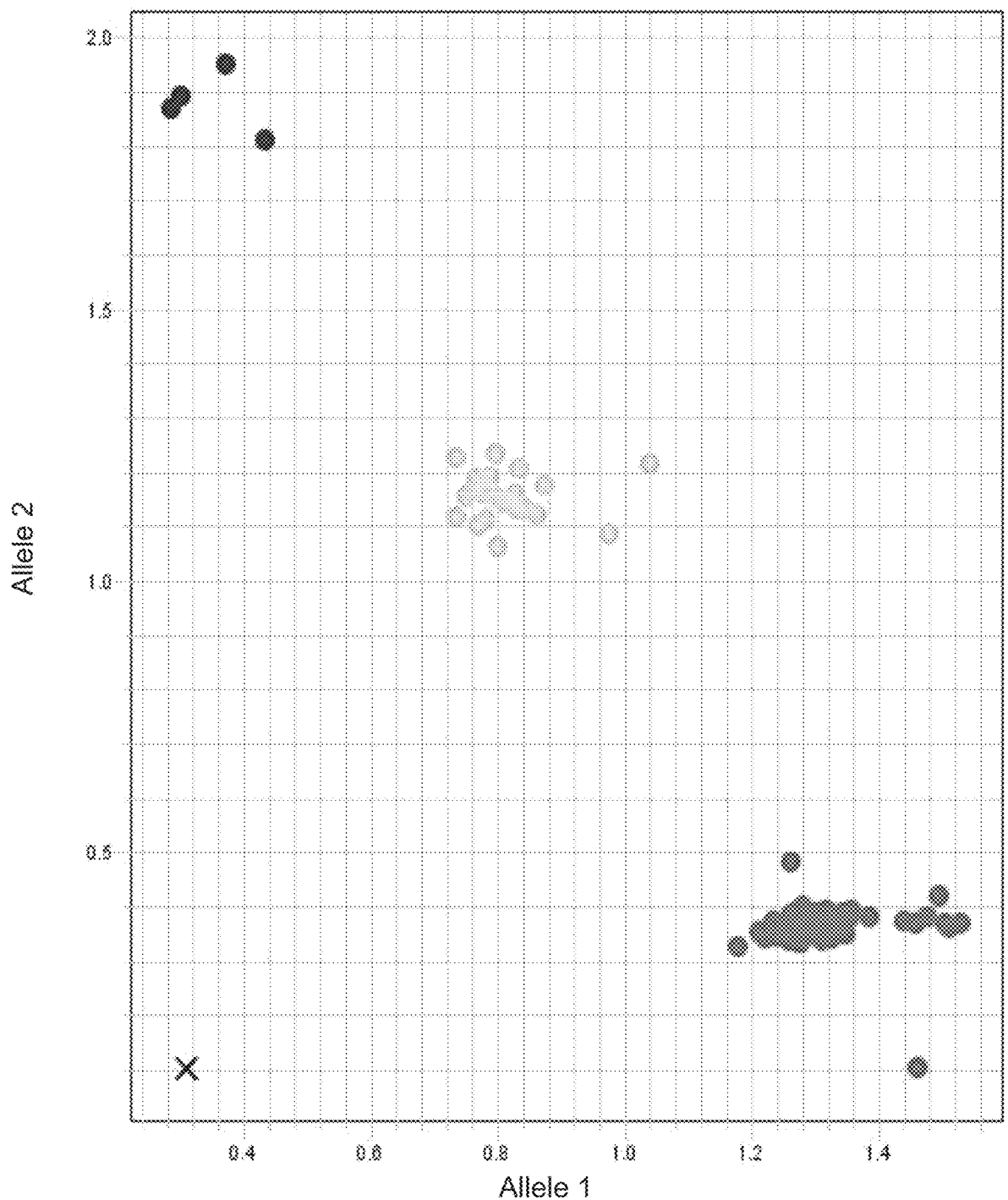

UFP chemistry-based genotyping assays were tested with a panel of 92 gDNAs (3 ng/well) with 25 nM for each UFP and 300 nM for each ASP, 900 nM for the LSP in each reaction. The UFP for ASP1 was labeled with FAM™ and the UFP for ASP2 was labeled with VIC®. The cycling conditions were: [95° C., 10 min], [(92° C., 15 sec(58°) C., 1 min)]$_{x5}$ cycles, [(92° C., 15 sec(60°) C., 1 min)]×45 cycles. The allelic discrimination plots shown in FIGS. 6A-6H show distribution of the homozygous allele 1(lower right hand corner of the plot); homozygous allele 2 (upper left corner of the plot); heterozygous (located midway or diagonally from each of the homozygous signals); and no template control (NTC) (shown as x near bottom left corner of the plot). This distribution arises from the differential labeling for allele 1 and 2, and resultant mixed signal from heterozygotes. Any sample wells which cannot be distinguished as having one of these three conditions are represented as "x". Assay performance was improved as assay design parameters were modified. This is demonstrated in the comparisons in each of FIGS. 6A-H. The results from four different SNPs are evaluated, including hCV1117072 (FIGS. 6And B); hCV2017662 (FIGS. 6C and D); hCV1115414 (FIGS. 6E and F); and hCV25473309 (FIGS. 6G and H). In each of FIGS. 6A, 6C, 6E, and 6G, design1 of the ASP is used. In each of FIGS. 6B, 6D, 6F, and 6H, design2 of the ASP is used. The allelic discrimination plots show Design2 provides much better allelic discrimination, as there are much reduced numbers of uncalled sample wells and tighter clustering of the observed signals in FIG. 6B as compared to FIG. 6A; FIG. 6D as compared to FIG. 6C; FIG. 6F as compared to FIG. 6E; and FIG. 6H as compared to FIG. 6G.

Example 4

Comparison with TaqMan® Genotyping Assays
(See FIGS. 7A-7H)

Figure 7A:
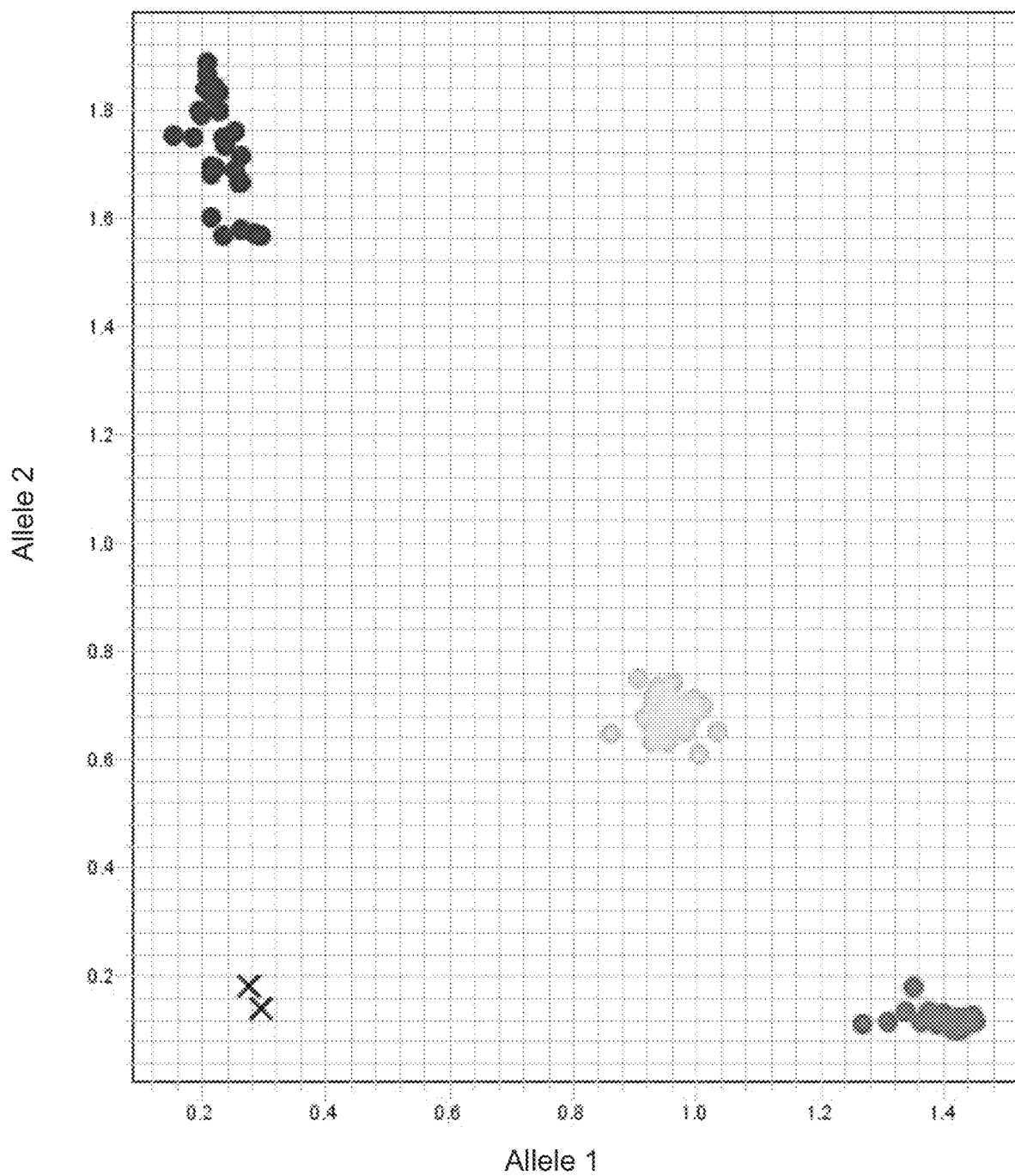
FIGS. 7A through 7H: Performance comparison between certain of the UFP-based genotyping assays described herein and standard TaqMan® SNP assays. Allele discrimination plots from universal reporter-based genotyping assays were compared to TaqMan® SNP assays. The NTC (non-template control) and background signals of the universal reporter-based genotyping assays were lower than those of TaqMan® SNP assays.
Figure 7B:
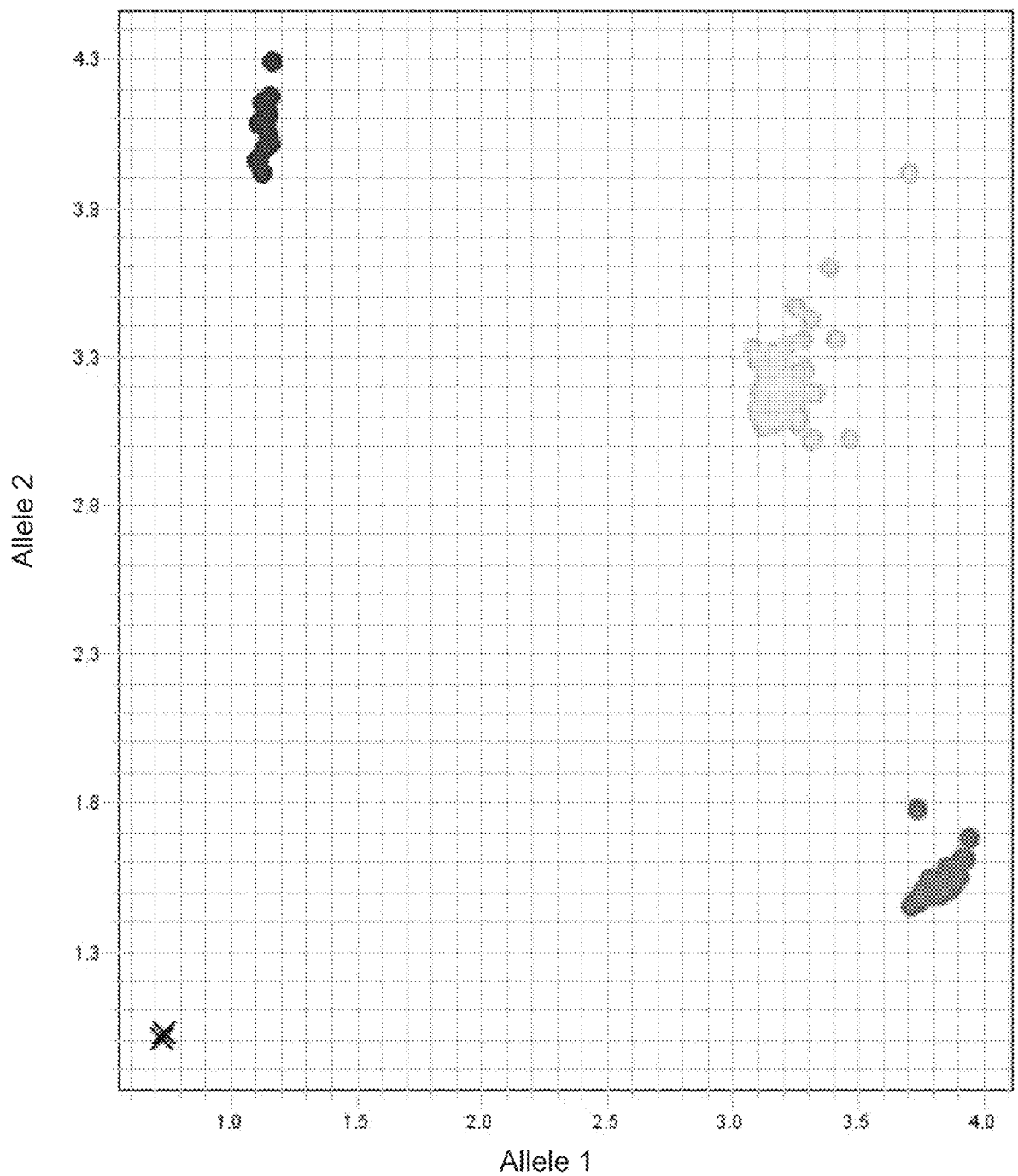
Figure 7C:
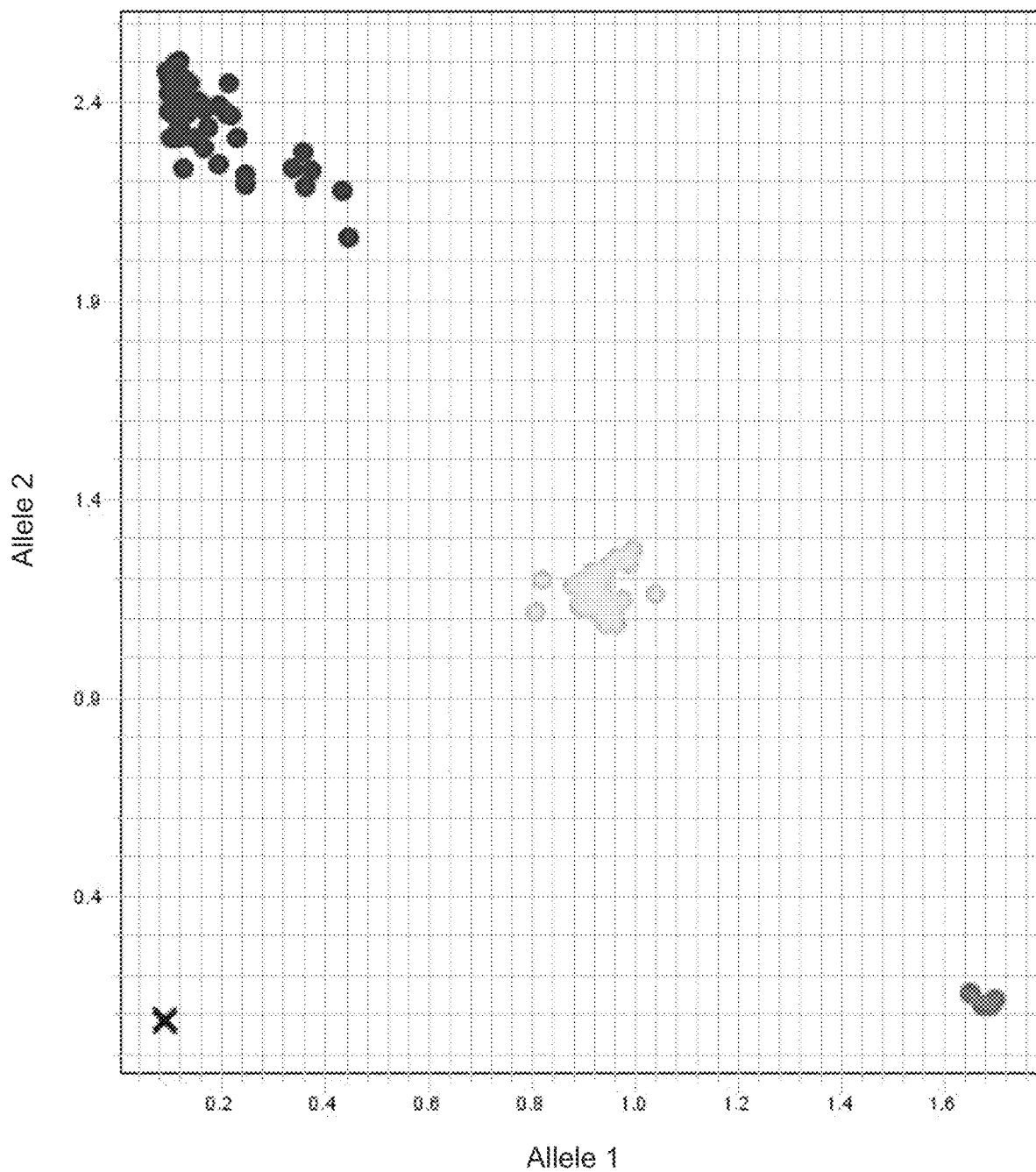
Figure 7D:
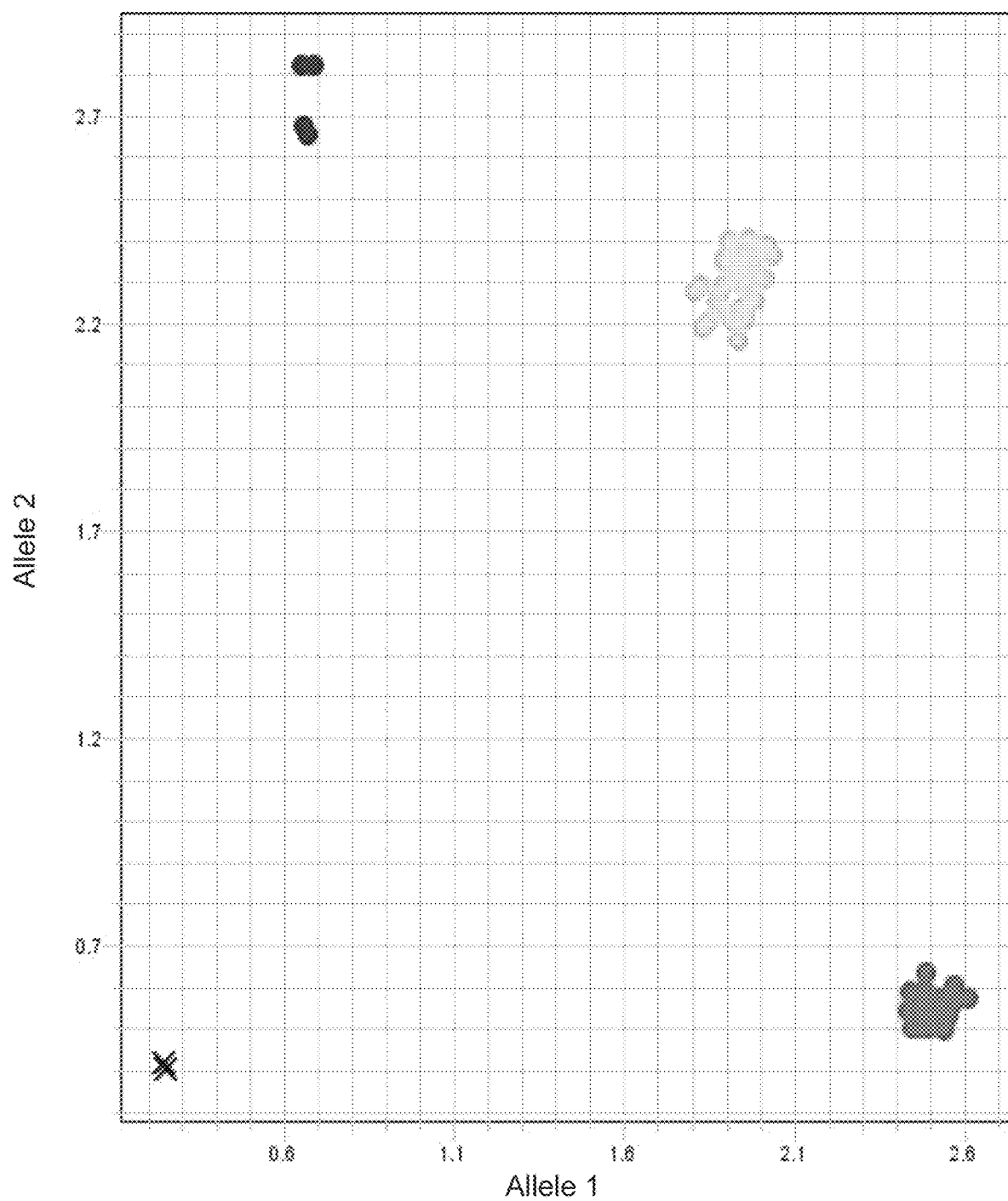
Figure 7E:
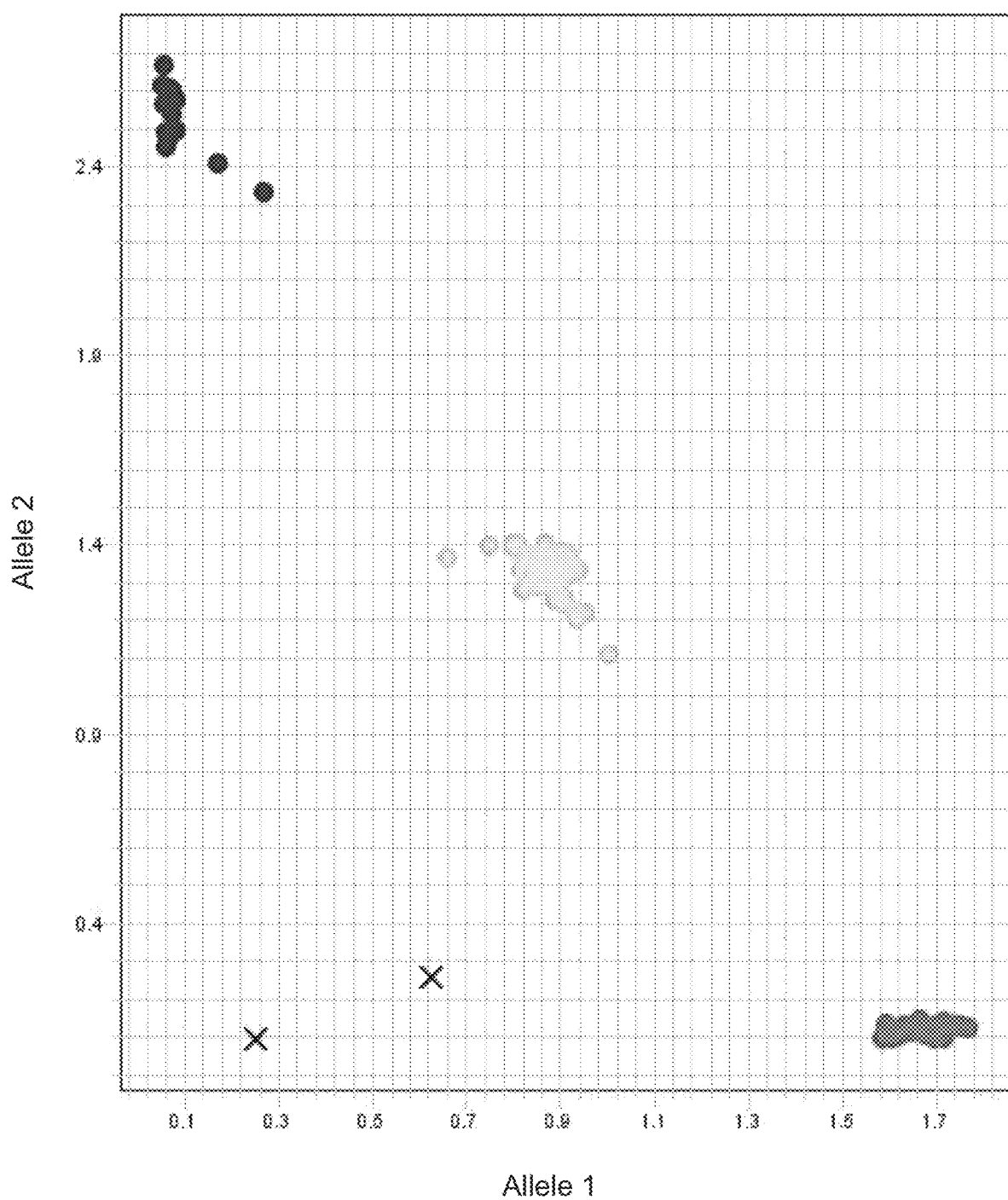
Figure 7F:
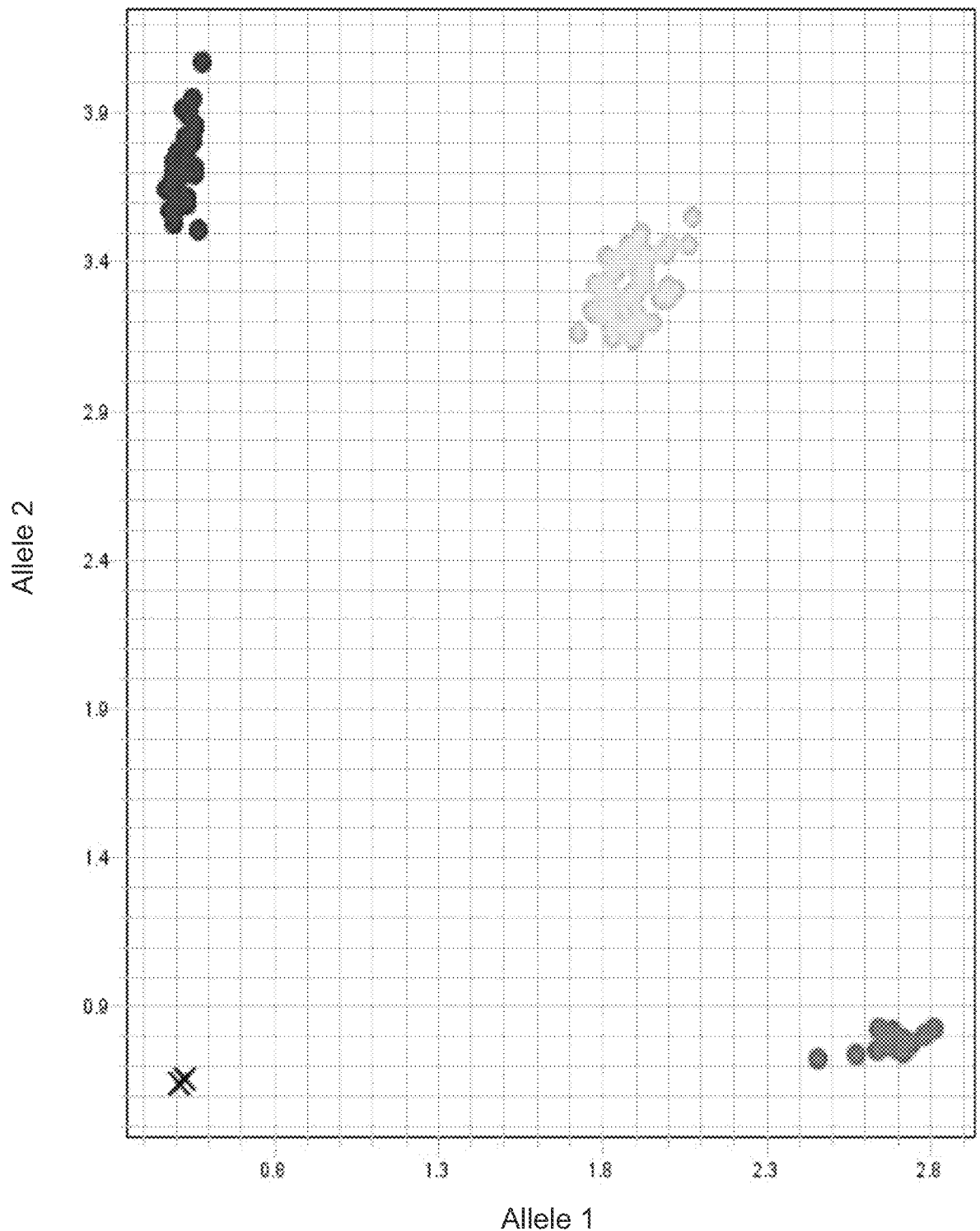
Figure 7G:
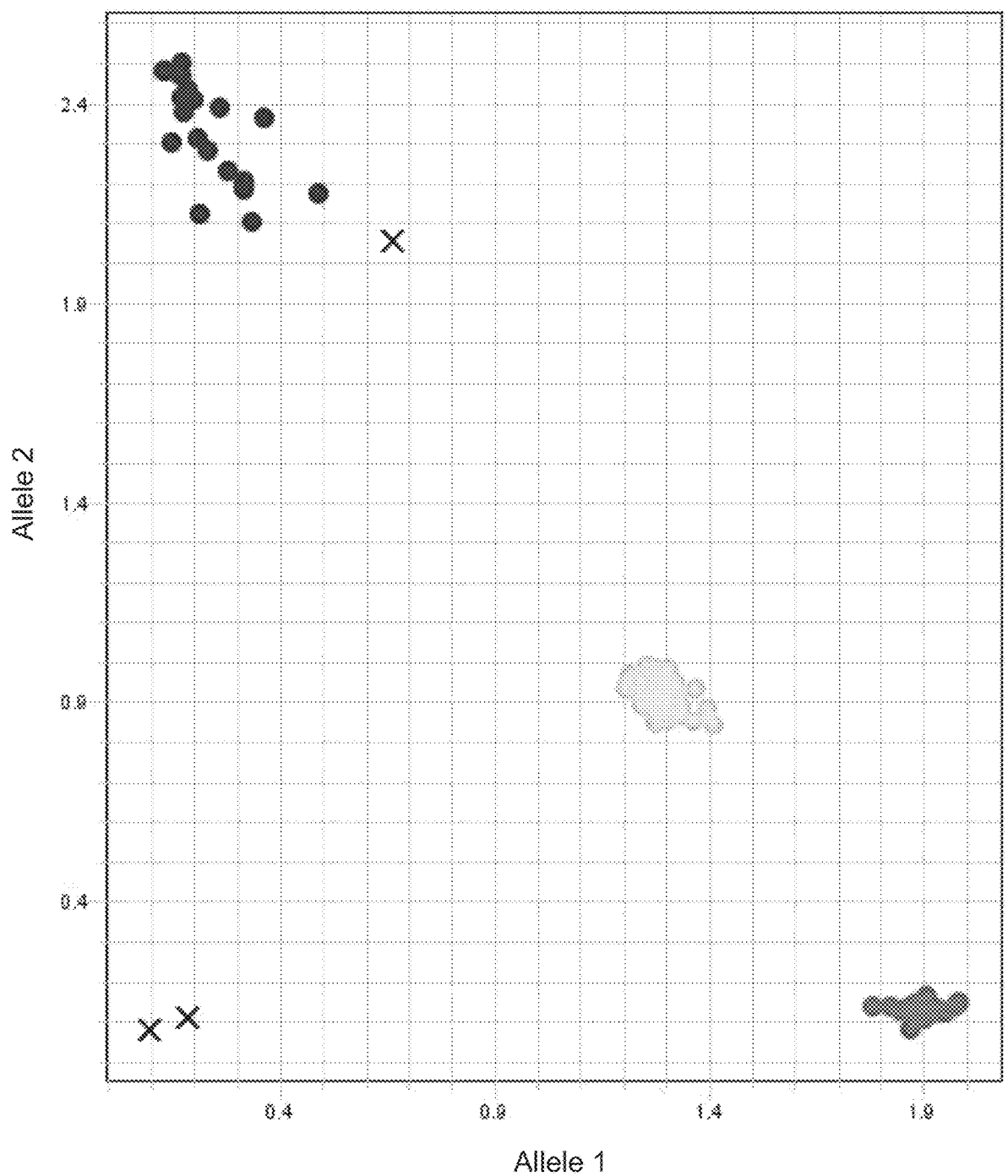
Figure 7H:
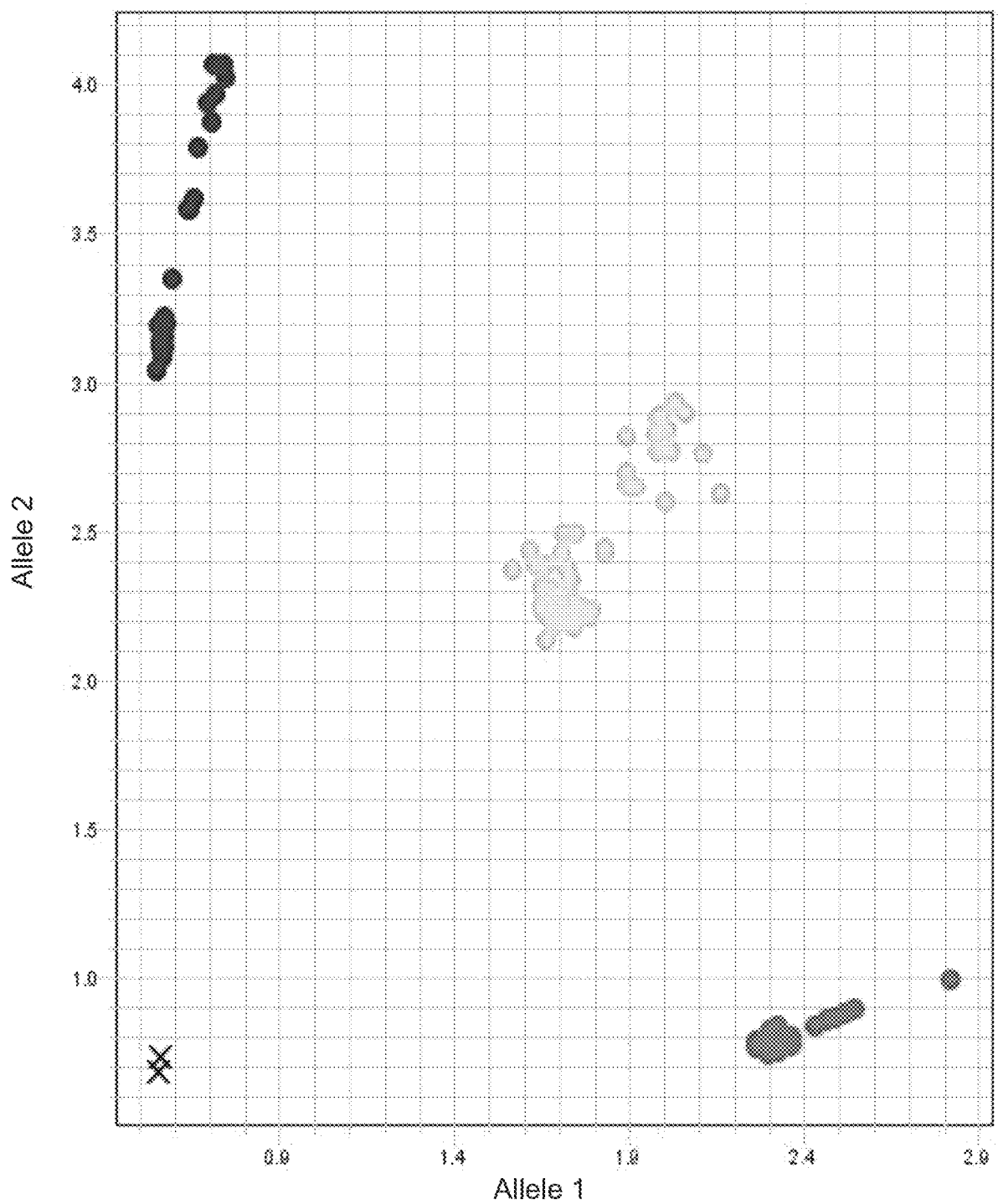

Performance of allele discrimination was compared by using UFP-based genotyping assays and TaqMan® SNP assays. The targets were selected based on TaqMan® SNP assays that gave three distinct clusters, and include hCV1113699, hCV2623923, hCV1117072, and hCV1150692. UFP-based genotyping assays were performed using ASPs, UFPs and LSP as described above. TaqMan® genotyping assays were run under the manufacturer's recommended conditions [(92° C., 15 sec(60°) C., 1 min)] except for running 40 cycles. FIG. 7A shows the allelic discrimination plot for the hCV 1113699 SNP assay using the UFP-based genotyping assay and FIG. 7B shows the allelic discrimination plot for the hCV1113699 TaqMan® SNP assay. FIG. 7C shows the allelic discrimination plot for the hCV2623923 SNP assay using the UFP-based genotyping assay and FIG. 7D shows the allelic discrimination plot for the hCV2623923 TaqMan® SNP assay. FIG. 7E shows the allelic discrimination plot for the hCV 1117072 SNP assay using the UFP-based genotyping assay and FIG. 7F shows the allelic discrimination plot for the hCV 1117072 TaqMan® SNP assay. Finally, FIG. 7G shows the allelic discrimination plot for the hCV 1150692 SNP assay using the UFP-based genotyping assay and FIG. 7H shows the allelic discrimination plot for the hCV 1150692 TaqMan® SNP assay. Although overall signals of UFP-based genotyping assays were slightly weaker, NTC and background signal was also lower, therefore the S/N ratio was not lower. The cluster separation was similar or gave slightly better angles, thus demonstrating that the UFP-based genotyping assays can provide as sensitive and accurate results as commercially available TaqMan® technology. The cluster tightness and display may be improved by further assay design and assay chemistry optimization to provide even better discriminatory power.

We claim:

1. A method for determining the genotype of a target nucleic acid molecule, the method comprising:
   a) providing a mixture which includes:
      one or more target nucleic acid molecules;
      a first allele-specific primer, which is specific for a first allele, containing a first 5'-universal tail which includes a first binding sequence;
      a first universal FRET-based reporter primer (UFP), wherein the first UFP includes a first fluorophore, a first quencher moiety, and a sequence between the first fluorophore and the first quencher moiety in a single, single-stranded molecule, said sequence being identical to the first binding sequence;
      a second allele-specific primer which is specific for a second allele, containing a second 5'-universal tail which includes a second binding sequence;
      a second UFP, wherein the second UFP includes a second fluorophore, a second quencher moiety, and a sequence between the second fluorophore and the second quencher moiety in a single, single-stranded molecule, said sequence being identical to the second binding sequence, wherein the first and second fluorophore are different and the first quencher moiety and the second quencher moiety are the same or different; and
      a locus specific primer;
   b) amplifying the target nucleic acids in the mixture using a spectrophotometric thermal cycler, the step of amplifying the target nucleic acids including extension of the 3' end of the first UFP and/or extension of the 3' end of the second UFP;
   c) measuring the intensities of the first fluorophore from the first UFP and the second fluorophore from the second UFP using the spectrophotometric thermal cycler, wherein said first and second UFPs comprise the first quencher moiety and the second quencher moiety, respectively; and
   d) analyzing nucleic acid genotypes based on the intensities of the first and second fluorophores.

2. The method of claim 1, wherein the first fluorophore and the second fluorophore are located at the 5'-end of the first UFP and the second UFP, respectively, and the first quencher moiety and the second quencher moiety are located at an internal nucleotide of the first UFP and the second UFP, respectively.

3. The method of claim 1, wherein the 3'-end of at least one of the allele-specific primers and/or locus-specific primer includes a blocking agent such that the blocked end is configured to be activated by pyrophosphorolysis.

4. The method of claim 3, wherein the blocking agent is a dideoxynucleotide (ddN).

5. The method of claim 1, wherein the first UFP is an extendable UFP and it is replaced with a first non-extendable universal FRET-based detector probe, wherein the first universal FRET-based detector probe includes at least a first quencher moiety and a first fluorophore; and the second UFP is an extendable UFP and it is replaced with a second non-extendable universal FRET-based detector probe, wherein the second universal FRET-based detector probe includes at least a second quencher moiety and a second fluorophore; wherein the first and second fluorophores are different, and the first quencher moiety and the second quencher moiety are the same or different.

6. A method for determining the genotype of a target nucleic acid molecule, the method comprising:
   a) providing a mixture which includes:
      one or more target nucleic acid molecules;
      a first allele-specific primer, which is specific for a first allele, containing a first 5'-universal tail which includes a binding site for a first UFP;
      a first UFP, wherein the first UFP includes a first fluorophore, a first quencher moiety, and a sequence between the first fluorophore and the first quencher moiety in a single molecule, said sequence binding to the binding site in the first allele-specific primer;
      a second allele-specific primer which is specific for a second allele, comprising a second 5'-universal tail which includes a binding site for a second UFP;
      a second UFP, wherein the second UFP includes a second fluorophore, a second quencher moiety, and a sequence between the second fluorophore and the second quencher moiety in a single molecule, said sequence binding to the binding site in the second allele-specific primer; wherein the first and second fluorophore are different and are not directly excited by an excitation light;

a locus specific primer; and a double-stranded nucleic acid intercalator dye; wherein the double-stranded nucleic acid intercalator dye is configured to be directly excited by the excitation light and its fluorescence excites the first and/or the second fluorophores;

b) amplifying the target nucleic acids in the mixture;

c) exposing the mixture to the excitation light and measuring the intensities of the first and the second fluorophores from the first and second UFPs, wherein said first and second UFPs comprise the first quencher moiety and the second quencher moiety, respectively; and d) analyzing nucleic acid genotypes based on the intensities of the first and second fluorophores.

7. The method of claim 6, wherein the first fluorophore and the second fluorophore are located at the 5'-end of the first UFP and second UFP, respectively.

8. The method of claim 6, wherein the 3'-end of at least one of the allele-specific primers and/or locus-specific primer includes a blocking agent such that the blocked end is configured to be activated by pyrophosphorolysis.

9. The method of claim 8, wherein the blocking agent is a dideoxynucleotide (ddN).

10. The method of claim 1, wherein steps (b) and (c) occur simultaneously.

11. The method of claim 6, wherein steps (b) and (c) occur simultaneously.

12. The method of claim 3, wherein the mixture further includes a pyrophosphorolysis enzyme.

13. The method of claim 8, wherein the mixture further includes a pyrophosphorolysis enzyme.

14. The method of claim 1, wherein the first UFP and/or the second UFP is in a linear conformation under non-denaturing conditions.

15. The method of claim 6, wherein the first UFP and/or the second UFP is in a linear conformation under non-denaturing conditions.

16. The method of claim 1, wherein the concentration of the locus specific primer is at least 3X higher than the concentration of the first allele specific primer and/or the second allele specific primer.

17. The method of claim 6, wherein the concentration of the locus specific primer is at least 3X higher than the concentration of the first allele specific primer and/or the second allele specific primer.

18. The method of claim 1, wherein the first UFP and the second UFP do not bind to said one or more target nucleic acid molecules.

19. The method of claim 6, wherein the first UFP and the second UFP do not bind to said one or more target nucleic acid molecules.

20. A method for determining the genotype of a target nucleic acid molecule, the method comprising:

a) providing a mixture which includes:

one or more target nucleic acid molecules;

a first allele-specific primer, which is specific for a first allele, comprising a first 5'-universal tail which includes a first binding sequence;

a first UFP, wherein the first UFP includes a first fluorophore, a first quencher moiety, and a sequence between the first fluorophore and the first quencher moiety in a single, single-stranded molecule, said sequence being identical to the first binding sequence;

a second allele-specific primer which is specific for a second allele, comprising a second 5'-universal tail which includes a second binding sequence;

a second UFP, wherein the second UFP includes a second fluorophore, a second quencher moiety, and a sequence between the second fluorophore and the second quencher moiety in a single molecule, said sequence being identical to the second biding sequence, wherein the first and second fluorophore are different and are not directly excited by an excitation light;

a locus specific primer; and a double-stranded nucleic acid intercalator dye, wherein the double-stranded nucleic acid intercalator dye is configured to be directly excited by the excitation light and its fluorescence exciting the first and/or the second fluorophores;

b) amplifying the target nucleic acids in the mixture, the step of amplifying the target nucleic acids including extension of the 3' end of the first UFP and/or extension of the 3' end of the second UFP;

c) exposing the mixture to the excitation light and measuring the intensities of the first and the second fluorophores from the first and second UFPs, wherein said first and second UFPs comprise the first quencher moiety and the second quencher moiety, respectively; and d) analyzing nucleic acid genotypes based on the intensities of the first and second fluorophores.

* * * * *